United States Patent [19]

Ernest et al.

[11] 4,070,477
[45] Jan. 24, 1978

[54] 2-PENEM COMPOUNDS

[75] Inventors: Ivan Ernest, Birsfelden; Jacques Gosteli, Basel, both of Switzerland; Robert Burns Woodward, Cambridge, Mass.

[73] Assignee: Ciba-Geigy Corporation, Ardsley, N.Y.

[21] Appl. No.: 746,979

[22] Filed: Dec. 2, 1976

[30] Foreign Application Priority Data

Dec. 8, 1975   Switzerland .................. 15914/75
June 28, 1976  Switzerland .................. 8252/76

[51] Int. Cl.² .................. A61K 31/43; A61K 31/425; C07D 499/02; C07D 499/44
[52] U.S. Cl. .................. 424/271; 260/239.1; 260/296 B; 260/306.7 C; 424/263; 424/270; 260/239 A
[58] Field of Search .................. 260/239.1, 306.7 C, 260/296 B; 424/271, 270, 263

[56] References Cited

U.S. PATENT DOCUMENTS 3,778,432  12/1973  Pines .................. 260/243 C

Primary Examiner—Gerald A. Schwartz
Attorney, Agent, or Firm—John J. Maitner

[57] ABSTRACT

The invention relates to 6-amino-2-penem-3-carboxylic acid compounds of the formula

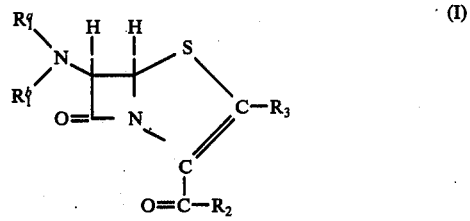

in which $R_1{}^a$ denotes hydrogen or an amino protective group $R_1{}^A$ and $R_1{}^b$ represents hydrogen or an acyl radical Ac, or in which $R_1{}^a$ and $R_1{}^b$ conjointly form a bivalent amino protective group, $R_2$ denotes hydroxyl or a radical $R_2{}^A$ which, together with the carbonyl grouping —C(=O)—, forms a protected carboxyl group, and $R_3$ represents hydrogen or an organic radical which is linked via a carbon atom to the ring carbon atom, and 1-oxides thereof, as well as salts of such compounds having salt-forming groups, which compounds possess antibiotic properties, processes for the manufacture of such compounds, and also pharmaceutical formulations containing compounds of the formula I with pharmacological properties, and the use thereof, either as antibiotics, preferably in the form of pharmaceutical formulations, or as intermediate products.

12 Claims, No Drawings

2-PENEM COMPOUNDS

Since the discovery of penicillin, numerous bicyclic thia-aza compounds which have a β-lactam structure and contain, as the bicyclic structural element, in the main the penam or the 3-cephem structure have been disclosed. In the penam and 3-cephem compounds a large multiplicity of, in particular, the substituents on the 6- or 7-amino group and the substituents in the 2- or 3-position have been modified. The sulphur has been replaced by other atoms, such as oxygen or carbon, and substituents, for example methoxy, have been introduced into the 6α-position or 7α-position. A review of earlier work is given by E. H. Flynn, "Cephalosporins and Penicillins", Academic Press, New York and London, 1972. The most recent developments have been described by J. Cs. Jaszberenyi et al., Progr. Med. Chem., volume 12, 1975, 395–477, and P. G. Sammes, Chem. Rev. 1976, volume 76, No. 1, 113–155.

The occurrence of new pathogenic germs whch have become resistant to the antibiotics used hitherto, and the known allergy phenomena, compel research continuously to seek new active compounds. The value of these compounds will be considered to be the greater the greater the extent to which the compounds differ, in respect of structure, from the ring systems, and their modifications, known hitherto, since this will increase the possibility that the new compounds will possess the said disadvantages to a lesser extent, or not at all. However, there is always a danger that deviations from the penam or 3-cephem ring system will lead to a loss of the antibiotic activity.

The object on which the present invention is based is to manufacture bicyclic thia-aza compounds which contain a β-lactam ring, possess a novel ring system and are active both against normal germs and against resistant germs and which in some cases do not possess the other disadvantages of the former antibiotics having a β-lactam structure.

The manufacture, according to the invention, of the novel ring system, and the new intermediate products required for this, open up in addition new fields for research for further compounds which can be utilised industrially.

The novel ring system has the formula

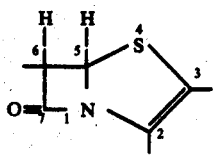

and systematically can be designated as 5R,6R-7-oxo-4-thia-1-azabicyclo[3.2.0]hept-2-ene. For the sake of simplicity, it is termed "2-penem" in the text which follows and the following numbering, which is customary in penicillin chemistry and derives from penam, is used:

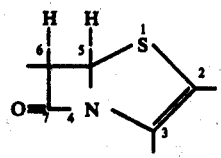

The present invention relates to bicyclic unsaturated thia-aza compounds which contain this ring system and especially to 6-amino-2-penem-3-carboxylic acid compounds of the formula

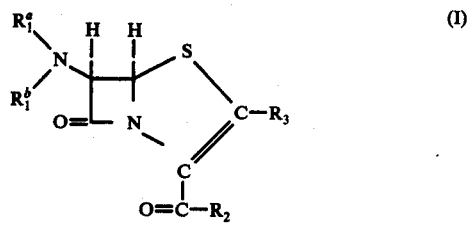

in which $R_1^a$ denotes hydrogen or an amino protective group $R_1^A$ and $R_1^b$ represents hydrogen or an acyl radical Ac, or in which $R_1^a$ and $R_1^b$ conjointly form a bivalent amino protective group, $R_2$ denotes hydroxyl or a radical $R_2^A$ which, together with the carbonyl grouping —C(=O)—, forms a protected carboxyl group, and $R_3$ represents hydrogen or an organic radical which is linked via a carbon atom to the ring carbon atom, and 1-oxides thereof, as well as salts of such compounds having salt-forming groups, processes for the manufacture of such compounds, and also pharmaceutical formulations containing compounds of the formula I with pharmacological properties, and the use of the new compounds, either as pharmacological active compounds, preferably in the form of pharmaceutical formulations, or as intermediate products.

An amino protective group $R_1^A$ is a group which can be replaced by hydrogen, above all an acyl group Ac, and also a triarylmethyl group, as well as an organic silyl group or stannyl group.

An acyl group Ac, which can also denote the radical $R_1^b$, is, above all, the acyl radical of an organic carboxylic acid, preferably with up to 18, and above all with up to 10, carbon atoms, especially the acyl radical of an optionally substituted aliphatic, cycloaliphatic, cycloaliphatic-aliphatic, aromatic, araliphatic, heterocyclic or heterocyclic-aliphatic carboxylic acid and in particular represents an acyl radical of an organic carboxylic acid, preferably with up to 18, and above all with up to 10, carbon atoms, contained in an N-acyl derivative, which is naturally occurring, or can be prepared biosynthetically, semi-synthetically or entirely synthetically and is preferably pharmacologically active, of a 6-amino-penam-3-carboxylic acid compound or a 7-amino-3-cephem-4-carboxylic acid compound.

An acyl radical Ac of this type is, above all, a group of the formula

in which (1) $R_a$ represents an optionally substituted carbocyclic aryl radical, for example corresponding phenyl, an optionally substituted, preferably unsaturated, cycloaliphatic hydrocarbon radical, for example corresponding cyclohexadienyl or cyclohexenyl, or an optionally substituted heterocyclic aryl radical, for example corresponding thienyl or furyl, $R_b$ represents hydrogen and $R_c$ represents hydrogen or optionally substituted, and especially protected, hydroxyl, amino, carboxyl or sulpho, or in which (2) $R_a$ denotes cyano, etherified hydroxyl or mercapto, such as optionally substituted phenoxy, phenylthio or pyridylthio, or an optionally substituted, unsaturated heterocyclic radical which is linked via a ring nitrogen atom, for example corresponding tetrazolyl, and $R_b$ and $R_c$ denote hydrogen, or in which (3) $R_a$ denotes an optionally substituted carbocyclic aryl radical, for example corresponding phenyl, or an optionally substituted heterocyclic aryl radical, for example corresponding thienyl or furyl, and $R_b$ and $R_c$ together denote preferably O-substituted hydroxyimino in the syn-configuration.

Cyclohexadienyl is in particular 1,4-cyclohexadienyl, whilst cyclohexenyl is above all 1-cyclohexenyl.

Thienyl is preferably 2-thienyl and also 3-thienyl and furyl in particular denotes 2-furyl, whilst pyridylthio represents, for example, 4-pyridylthio and tetrazolyl represents, for example, 1-tetrazolyl.

Substituents of a phenyl or phenoxy group $R_a$ can be in any position and are, inter alia, aliphatic hydrocarbon radicals, such as optionally substituted, for example protected, aminomethyl, optionally functionally modified, such as etherified or esterified, hydroxyl or optionally substituted, and especially protected, amino, such as acylamino, or nitro, which can be, for example, in the 2-position of the phenoxy group.

Substitutents of a cyclohexadienyl or cyclohexenyl group and of a thienyl or furyl group $R_a$ are, for example, optionally substituted lower alkyl, such as optionally substituted, for example, protected, aminomethyl, and such a substituent, especially optionally substituted aminomethyl, is above all in the 2-position of a 1,4-cyclohexadienyl radical or 1-cyclohexenyl radical or in the 5-position of a 2-thienyl radical or 2-furyl radical.

Optionally protected aminomethyl is, above all, aminomethyl which is optionally substituted by lower alkyl, for example methylaminomethyl, in which amino is optionally protected, whilst etherified hydroxyl can be, for example, lower alkoxy, such as methoxy, and esterified hydroxyl can be, for example, lower alkanoyloxy, such as acetyloxy, aroyloxy, for example benzoyloxy, carbamoyloxy or halogen, for example chlorine, and optionally substituted amino can be, for example, amino substituted by lower alkyl, for example methylamino, or lower alkylsulphonylamino, for example methylsulphonylamino.

Protected hydroxyl, amino, carboxyl or sulpho groups in acyl radicals of the formula IA are those which are customary in penicillin and cephalosporin chemistry and which can easily be converted into free hydroxyl, amino, carboxyl or sulpho groups without this resulting in the 2-penem structure being destroyed or in other undesired side reactions taking place. Those protective groups which can be split off under neutral or basic conditions are preferred.

Amino groups can be protected, for example, by acyl radicals and an acyl radical is, above all, an acyl radical of a half-ester of carbonic acid which can be split off by reduction, for example on treatment with a chemical reducing agent or with catalytically activated hydrogen, or by solvolysis, for example by treatment with a suitable acid, and also by means of irradiation, such as a lower alkoxycarbonyl radical which, preferably on the first carbon atom of the esterifying group, is multibranched and/or substituted by aryl, for example phenyl or biphenylyl, which is optionally substituted, such as by lower alkoxy, for example methoxy, and/or nitro, or by arylcarbonyl, especially benzoyl, for example tert.-butoxycarbonyl, tert.-pentyloxycarbonyl, diphenylmethoxycarbonyl, 1-(4-biphenylyl)-1-methyl-ethoxycarbonyl, benzyloxycarbonyl, 4-nitrobenzyloxycarbonyl, 2-nitro-4,5-dimethoxy-benzyloxycarbonyl or phenacyloxycarbonyl, or a lower alkoxycarbonyl radical which is substituted, on the second carbon atom of the esterifying group, by halogen, for example 2,2,2-trichloroethoxycarbonyl or 2-iodoethoxycarbonyl (or a radical which can be converted into the latter, such as 2-chloro- or 2-bromoethoxycarbonyl), and also polycyclic cycloalkoxycarbonyl, for example adamantyloxycarbonyl.

An amino group can also be protected by an arylmethyl radical, such as a polyarylmethyl radical, for example by trityl, a 2-carbonyl-vinyl grouping, such as a 1-lower alkoxycarbonyl-1-propen-2-yl group, for example 1-methoxycarbonyl-1-propen-2-yl, an arylthio or aryl-lower alkylthio group, for example 2-nitrophenylthio or pentachlorophenylthio, and also tritylthio, or an arylsulphonyl group, and also by an organic silyl or stannyl group, such as a silyl or stannyl group which is substituted by lower alkyl, halogeno-lower alkyl, cycloalkyl, phenyl or phenyl-lower alkyl, or optionally functionally modified groups, such as lower alkoxy, for example methoxy, or halogen, for example chlorine, above all tri-lower alkylsilyl, for example trimethylsilyl, halogeno-lower alkoxy-lower alkylsilyl, for example chloromethoxymethylsilyl, or tri-lower alkylstannyl, for example tri-n-butylstannyl.

Hydroxyl protective groups are, for example, acyl radicals, especially one of the acyl radicals of carbonic acid half-esters mentioned in connection with a protected amino group, or organic silyl or stannyl radicals, and also 2-oxa- or 2-thia-aliphatic or -cycloaliphatic hydrocarbon radicals which can be split off easily, above all 1-lower alkoxy-lower alkyl or 1-lower alkylthio-lower alkyl, for example 1-methoxyethyl, 1-ethoxy-ethyl, 1-methylthio-ethyl or 1-ethylthioethyl, or 2-oxa- or 2-thia-cyclo-lower alkyl with 5–7 ring atoms, for example 2-tetrahydrofuryl or 2-tetrahydropyranyl or corresponding thia analogues, as well as optionally substituted α-phenyl-lower alkyl radicals which can be split off easily, such as optionally substituted benzyl or diphenylmethyl, possible substituents of the phenyl radicals being, for example, halogen, such as chlorine, lower alkoxy, such as methoxy, and/or nitro.

A protected carboxyl group or sulpho group is, above all, a carboxyl or sulpho group esterified with an aliphatic, cycloaliphatic, cycloaliphatic-aliphatic, aromatic or araliphatic alcohol, such as a lower alkanol, or with a silyl or stannyl radical, such as tri-lower alkylsilyl. In a carboxyl or sulpho group, the hydroxyl group can be etherified, for example like the hydroxyl group in an esterified carboxyl group of the formula —C(=O)—$R_2$.

O-Substituted hydroxyimino is, in particular, lower alkoxyimino, for example methoxyimino or ethoxyimino, and also phenoxyimino or phenyl-lower alkoxyimino, for example benzyloxyimino, and such groups are preferably in the syn-form.

An amino group protected by an amino protective group $R_1^4$ can also be, for example, an amino group protected by the acyl radical of a carbonic acid half-ester, a 2-carbonyl-vinyl, arylthio or aryl-lower alkylthio or arylsulphonyl group, a triarylmethyl radical or an organic silyl or stannyl group, and such a protective group can be analogous to those in a correspondingly protected amino group in an acyl radical of the formula IA.

A bivalent amino protective group formed by the radicals $R_1^a$ and $R_1^b$ together is, in particular, the bivalent acyl radical of an organic dicarboxylic acid, preferably with up to 18 carbon atoms, above all the diacyl radical of an aliphatic or aromatic dicarboxylic acid, for example the acyl radical of a lower alkanedicarboxylic acid or lower alkenedicarboxylic acid, such as succinyl, or of an o-arylenedicarboxylic acid, such as phthaloyl, or is also the acyl radical of an α-aminoacetic acid which is preferably substituted in the α-position and contains, for example, an aromatic or heterocyclic radical, and in which the amino group is bonded to the nitrogen atom via a methylene radical which is preferably substituted and contains, for example, two lower alkyl groups, such as methyl groups, for example a 1-oxo-3-aza-1,4-butylene radical which is substituted, especially in the 2-position, and contains, for example, optionally substituted phenyl or thienyl and is optionally monosubstituted or disubstituted in the 4-position by lower alkyl, such as methyl, for example 4,4-dimethyl-2-phenyl-1-oxo-3-aza-1,4-butylene.

The radicals $R_1^a$ and $R_1^b$ can together also represent an organic ylidene radical, such as an aliphatic, cycloaliphatic, cycloaliphatic-aliphatic or araliphatic ylidene radical, preferably with up to 18 carbon atoms.

A protected carboxyl group of the formula —C(=O)—$R_2^A$ is, above all, an esterified carboxyl group, in which $R_2^A$ represents a hydroxyl group etherified by an organic radical or an organic silyl or stannyl group. Organic radicals, including those present as substituents in organic silyl or stannyl groups, are aliphatic, cycloaliphatic, cycloaliphatic-aliphatic, aromatic or araliphatic radicals, especially optionally substituted hydrocarbon radicals of this type, and also heterocyclic or heterocyclic-aliphatic radicals, preferably with up to 18 carbon atoms.

An etherified hydroxyl group $R_2^A$ forms, together with the carbonyl grouping, an esterified carboxyl group which can preferably be split easily, for example by reduction, such as by hydrogenolysis, or by solvolysis, such as by acidolysis or hydrolysis, and which can be split by oxidation or can easily be converted into another functionally modified carboxyl group, such as into another esterified carboxyl group or into a hydrazinocarbonyl group. Such a group $R_2^A$ is, for example, 2-halogeno-lower alkoxy, in which halogen preferably has an atomic weight of more than 19, for example 2,2,2-trichloroethoxy or 2-iodoethoxy, and also 2-chloroethoxy or 2-bromoethoxy which can easily be converted into 2-iodoethoxy, or 2-lower alkylsulphonyl-lower alkoxy, for example 2-methylsulphonylethoxy. The group $R_2^A$ is also a methoxy group which is polysubstituted by optionally substituted hydrocarbon radicals, especially saturated aliphatic or aromatic hydrocarbon radicals, such as lower alkyl, for example methyl, and/or phenyl, or is monosubstituted by an unsaturated aliphatic hydrocarbon radical, such as lower alkenyl, for example 1-lower alkenyl, such as vinyl, by a carbocyclic aryl group which contains electron-donating substituents, or by a heterocyclic group of aromatic character which contains oxygen or sulphur as a ring member, such as tert.-lower alkoxy, for example tert.-butoxy or tert.-pentyloxy, optionally substituted diphenylmethoxy, for example diphenylmethoxy or 4,4'-dimethoxy-diphenylmethoxy, lower alkenyloxy, especially 2-lower alkenyloxy, for example allyloxy, lower alkoxy-phenyl-lower alkoxy, for example lower alkoxy-benzyloxy, such as methoxybenzyloxy (in which methoxy above all is in the 3-, 4- and/or 5-position), above all 3- or 4-methoxybenzyloxy, or 3,4-dimethoxybenzyloxy, or, above all, nitrobenzyloxy, for example 4-nitrobenzyloxy, 2-nitrobenzyloxy or 4,5-dimethoxy-2-nitrobenzyloxy, or furfuryloxy, such as 2-furfuryloxy. $R_2^A$ can also be 2-oxa- or 2thia-cycloalkoxy or -cycloalkenyloxy with 5–7 ring members, such as 2-tetrahydrofuryloxy, 2-tetrahydropyranyloxy or 2,3-dihydro-2-pyranyloxy, or a corresponding thia group, or arylcarbonylmethoxy, in which aryl in particular represents an optionally substituted phenyl group, for example phenacyloxy, or $R_2^A$, together with the —C(=O)— grouping forms an activated ester group and is, for example, nitrophenoxy, for example 4-nitrophenoxy or 2,3-dinitrophenoxy, or polyhalogenophenoxy, for example pentachlorophenoxy. However, $R_2^A$ can also be unbranched lower alkoxy, for example methoxy or ethoxy.

An organic silyloxy group or organic stannyloxy group $R_2^A$ is, particularly, a silyloxy or stannyloxy group which is substituted by 1 to 3 optionally substituted hydrocarbon radicals, preferably with up to 18 carbon atoms. It preferably contains, as substituents, aliphatic, cycloaliphatic, aromatic or araliphatic hydrocarbon radicals which are optionally substituted, for example substituted by lower alkoxy, such as methoxy, or by halogen, such as chlorine, such as lower alkyl, halogeno-lower alkyl, cycloalkyl, phenyl or phenyl-lower alkyl, and represents, above all, tri-lower alkylsilyloxy, for example trimethylsilyloxy, halogeno-lower alkoxy-lower alkylsilyloxy, for example chloromethoxy-methyl-silyloxy, or tri-lower alkylstannyloxy, for example tri-n-butylstannyloxy.

The group $R_2^A$ can also be an etherified hydroxyl group which, together with the carbonyl grouping —C(=O)—, forms an esterified carboxyl group which can be split under physiological conditions, above all an acyloxymethoxy group, in which acyl denotes, for example, the radical of an organic carboxylic acid, above all of an optionally substituted lower alkanecarboxylic acid, or in which acyloxymethyl forms the residue of a lactone. Hydroxyl groups etherified in this way are lower alkanoyloxy-methoxy, for example acetyloxymethyloxy or pivaloyloxymethoxy, amino-lower alkanoyloxymethoxy, especially α-amino-lower alkanoyloxymethoxy, for example glycyloxymethoxy, L-valyloxymethoxy and L-leucyloxymethoxy, and also phthalidyloxy.

Preferred groups $R_2^A$ are those which can be converted into a free hydroxyl group under neutral or alkaline conditions or also under physiological conditions.

A radical $R_2^A$ which, together with a —C(=O)— grouping, forms an optionally substituted hydrazinocarbonyl group is, for example, hydrazino or 2-lower alkylhydrazino, for example 2-methylhydrazino.

An organic radical $R_3$ which is bonded via a carbon atom to the ring carbon atom is, above all, an optionally substituted aliphatic, cycloaliphatic, cycloaliphatic-aliphatic, aromatic or araliphatic hydrocarbon radical, especially optionally substituted lower alkyl, cycloalkyl, cycloalkyl-lower alkyl, phenyl, naphthyl or phenyl-lower alkyl. Substituents of such radicals are, for example, optionally functionally modified, such as optionally etherified or esterified, hydroxyl or mercapto groups, for example hydroxyl, lower alkoxy, for example methoxy or ethoxy, lower alkanoyloxy, for example acetyloxy or propionyloxy, halogen, for example chlorine or bromine, or lower alkylmercapto, for example methylthio, or optionally functionally modified carboxyl groups, such as carboxyl, lower alkoxycarbonyl, for example methoxycarbonyl or ethoxycarbonyl, carbamoyl or cyano, and also nitro, or amino which is optionally monosubstituted or disubstituted, such as by lower alkyl, for example methyl or ethyl, or disubstituted by lower alkylene, for example 1,4-butylene or 1,5-pentylene.

A lower alkyl radical $R_3$ contains, for example, up to 7, and especially up to 4, carbon atoms and is, inter alia, methyl, ethyl, propyl, isopropyl, butyl, isobutyl, tert.-butyl or pentyl. Substituted lower alkyl is, above all, substituted methyl, such as hydroxymethyl, lower alkoxymethyl, for example methoxymethyl, lower alkanoyloxymethyl, for example acetyloxymethyl or propionyloxymethyl, or halogenomethyl, for example chloromethyl or bromomethyl, lower alkoxycarbonylmethyl, for example methoxycarbonylmethyl or ethoxycarbonylmethyl, or cyanomethyl.

A cycloalkyl radical $R_3$ has, for example, 3 to 7 carbon atoms and is, for example, cyclopropyl, cyclobutyl, cyclopentyl or cyclohexyl, whilst a cycloalkyl-lower alkyl radical $R_3$ contains, for example, 4 to 7 carbon atoms and represents, for example, cyclopropylmethyl, cyclobutylmethyl, cyclopentylmethyl or cyclohexylmethyl.

A phenyl or naphthyl radical, for example 1- or 2-naphthyl radical, $R_3$ or a phenyl-lower alkyl radical, for example a benzyl or 1- or 2-phenylethyl radical, $R_3$ can be substituted, preferably in the aromatic radical, for example by lower alkyl, such as methyl or ethyl, lower alkoxy, such as methoxy, or halogen, such as fluorine or chlorine, and also by nitro or amino.

A radical $R_3$ can also represent a heterocyclic or heterocyclic-aliphatic radical which is bonded via a carbon and is preferably of aromatic character, such as pyridyl, for example 2-, 3- or 4-pyridyl, thienyl, for example 2-thienyl, or furyl, for example 2-furyl, or can represent corresponding pyridyl-lower alkyl, thienyl-lower alkyl or furyl-lower alkyl radicals, especially pyridyl-methyl, thienyl-methyl or furylmethyl radicals.

Salts are, in particular, those of compounds of the formula I having an acid grouping, such as a carboxyl group, above all metal salts or ammonium salts, such as alkali metal salts and alkaline earth salts, for example sodium, potassium, magnesium or calcium salts, as well as ammonium salts with ammonia or suitable organic amines, possible amines for the salt formation being, above all, aliphatic, cycloaliphatic, cycloaliphatic-aliphatic and araliphatic primary, secondary or tertiary monoamines, diamines or polyamines, as well as heterocyclic bases, such as lower alkylamines, for example triethylamine, hydroxy-lower alkylamines, for example 2-hydroxyethylamine, di-(2-hydroxyethyl)-amine or tri-(2-hydroxyethyl)-amine, basic aliphatic esters or carboxylic acids, for example 2-diethylamino-ethyl 4-aminobenzoate, lower alkyleneamines, for example 1-ethyl-piperidine, cycloalkylamines, for example bicyclohexylamine, or benzylamines, for example N,N'-dibenzylethylenediamine, and also bases of the pyridine type, for example pyridine, collidine or quinoline. Compounds of the formula I which possess a basic group can also form acid addition salts, for example with inorganic acids, such as hydrochloric acid, sulphuric acid or phosphoric acid, or with suitable organic carboxylic acids or sulphonic acids, for example trifluoroacetic acid or p-toluenesulphonic acid. Compounds of the formula I having an acid group and a basic group can also be in the form of inner salts, that is to say in the form of a zwitter-ion. 1-Oxides of compounds of the formula I having salt-forming groups can also form salts, as described above. Salts which can be used pharmaceutically are preferred.

The compounds of the present invention display valuable pharmacological properties or can be used as intermediate products for the manufacture of such compounds. Compounds of the formula I in which, for example $R_1^a$ represents an acyl radical Ac occurring in pharmacologically active N-acyl derivatives of 6β-amino-penam-3-carboxylic acid compounds or 7β-amino-3-cephem-4-carboxylic acid compounds and $R_1^b$ represents hydrogen, or in which $R_1^a$ and $R_1^b$ together represent a 1-oxo-3-aza-1,4-butylene radical which is preferably substituted in the 2-position, for example by an aromatic or heterocyclic radical, and preferably substituted in the 4-position, for example by 2 lower alkyls, such as methyl, $R_3$ has the above-mentioned meaning and $R_2$ denotes hydroxyl or an etherified hydroxyl group $R_2^A$ which, together with the carbonyl group, forms an esterified carboxyl group which can be split easily, preferably under physiological conditions, and functional groups which may be present in an acyl radical Ac, such as amino, carboxyl, hydroxyl and/or sulpho, are usually in the free form, or salts, which can be used pharmacologically, of such compounds having salt-forming groups, inhibit, for example, the growth of Gram-positive germs, such as *Staphylococcus aureus* and *penicillin-resistant Staphylococcus aureus.*

Using compounds, according to the invention, of the formula I, inhibited zones about 16 to 19 mm in diameter are found in the disc-plate test for the two germs mentioned, using a 0.5% strength solution on filter paper (6 mm in diameter), whilst penicillin V tested analogously at the same time gives rise to inhibited zones of 36 to 38 mm in diameter in the case of normal germs and of only 9 to 13 mm in the case of resistant germs.

These new compounds, and especially the preferred compounds, or their salts which can be used pharmacologically, can thus be used, for example in the form of formulations having an antibiotic action, for the treatment of corresponding systemic infections and also as feedstuff additives, for preserving foodstuffs or as disinfectants.

1-Oxides of compounds of the formula I, in which $R_1^a$, $R_1^b$, $R_2$ and $R_3$ have the meanings indicated in the context of the formula I, or compounds of the formula I in which $R_3$ has the abovementioned meaning and the radicals $R_1^a$ and $R_1^b$ represent hydrogen, or $R_1^a$ denotes an amino protective group which differs from an acyl radical occurring in pharmacologically active N-acyl derivatives of 6β-amino-penam-3-carboxylic acid compounds or 7β-amino-3-cephem-4-carboxylic acid compounds and $R_1^b$ denotes hydrogen, or $R_1^a$ and $R_1^b$ together represent a bivalent amino protective group which differs from a 1-oxo-3-aza-1,4-butylene radical which is preferably substituted in the 2-position, for example by an aromatic or heterocyclic radical, and preferably substituted in the 4-position, for example by 2 lower alkyls, such as methyl, and $R_2$ represents hydroxyl, or $R_1^a$ and $R_1^b$ have the abovementioned meanings, $R_2$ represents a radical $R_2^A$ which, together with the —C(=O)— grouping forms a protected carboxyl group, which preferably can be split easily, a carboxyl group protected in this way differing from a carboxyl group which can be split physiologically, and $R_3$ has the abovementioned meanings, are valuable intermediate products which can be converted in a simple manner, for example as described below, into the abovementioned, pharmacologically active compounds.

The invention relates in particular to the 2-penem compounds of the formula I, in which $R_1{}^a$ denotes hydrogen or, preferably, an acyl radical contained in a fermentatively obtainable (that is to say naturally occurring) or biosynthetically, semi-synthetically or entirely synthetically obtainable, in particular pharmacologically active, such as highly active, N-acyl derivative of a 6β-amino-penam-3-carboxylic acid compound or 7β-amino-3-cephem-4-carboxylic acid compound, such as one of the abovementioned acyl radicals of the formula (IA), in which formula $R_a$, $R_b$ and $R_c$ above all have the meanings which have been singled out, and $R_1{}^b$ represents hydrogen, or in which $R_1{}^a$ and $R_1{}^b$ together represent a 1-oxo-3-aza-1,4-butylene radical which is preferably substituted in the 2-position, for example by an aromatic or heterocyclic radical, such as phenyl, and preferably substituted in the 4-position, for example by two lower alkyls, such as methyl, $R_2$ represents hydroxyl or represents a hydroxyl group etherified by an organic radical or an organic silyl or stannyl group or represents an optionally substituted hydrazino group $R_2{}^A$ and $R_3$ represents hydrogen, lower alkyl which is optionally substituted by etherified or esterified hydroxyl, such as lower alkoxy or lower alkanoyloxy, or phenyl or phenyl-lower alkyl which are optionally substituted by lower alkyl, lower alkoxy or halogen, and also by nitro or amino, as well as salts of such compounds having salt-forming groups.

Above all, in a 2-penem compound of the formula I or in a salt of such a compound having salt-forming groups, $R_1{}^a$ represents hydrogen or an acyl radical of the formula IA, in which (1) $R_a$ above all has the meanings which have been singled out and represents, for example, phenyl, thienyl, furyl, cyclohexadienyl or cyclohexenyl which are optionally substituted by hydroxyl, protected hydroxyl, lower alkoxy, lower alkanoyloxy, carbamoyloxy, halogen, lower alkylsulphonylamino or aminomethyl, $R_b$ represents hydrogen and $R_c$ represents hydrogen, optionally protected hydroxyl, optionally protected amino or optionally protected carboxyl or sulpho, or in which (2) $R_a$ represents cyano, 1-tetrazolyl, phenoxy which is optionally substituted, such as by phenyl, or 4-pyridylthio and $R_b$ and $R_c$ represent hydrogen, or in which (3) $R_a$ represents phenyl, thienyl or furyl and $R_b$ and $R_c$ together denote syn-lower alkoxyimino, $R_1{}^b$ represents hydrogen, $R_2$ denotes hydroxyl, optionally α-poly-branched lower alkoxy, for example methoxy or tert.-butoxy, or 2-halogeno-lower alkoxy, for example 2,2,2-trichloroethoxy, 2-iodoethoxy, or 2-chloroethoxy or 2-bromoethoxy which can easily be converted into 2-iodoethoxy, and also phenacyloxy, 1-phenyl-lower alkoxy with 1-3 phenyl radicals which are optionally substituted by lower alkoxy and/or nitro, for example 4-methoxybenzyloxy, 4-nitrobenzyloxy, 2-nitro-4,5-dimethoxy-benzyloxy, diphenylmethoxy, 4,4'-dimethoxydiphenylmethoxy or trityloxy, lower alkanoyloxymethoxy, for example acetyloxymethoxy or pivaloyloxymethoxy, α-amino-lower alkanoyloxymethoxy, for example glycyloxymethoxy, 2-phthalidyloxy, pentachlorophenoxy and also tri-lower alkylsilyloxy, for example trimethylsilyloxy, as well as lower alkenyloxy, especially 2-lower alkenyloxy, for example allyloxy, and $R_3$ represents hydrogen, lower alkyl, for example methyl or isopropyl, lower alkoxy-lower alkyl, for examply methoxymethyl, lower alkanoyloxymethyl, for example acetyloxymethyl, or phenyl or phenyl-lower alkyl which are optionally substituted by lower alkyl or halogen, and also by nitro or amino, for example benzyl.

The invention relates above all to 2-penem compounds of the formula I, in which $R_1{}^a$ represents hydrogen or, in particular, an acyl group of the formula IA, in which (1) $R_a$ denotes phenyl, hydroxyphenyl, for example 3- or 4-hydroxyphenyl, lower alkylsulphonylaminophenyl, for example 3-methylsulphonylamino-phenyl, aminomethylphenyl, for example 2-aminomethylphenyl, thienyl, for example 2- or 3-thienyl, aminomethylthienyl, for example 5-aminomethyl-2-thienyl, furyl, for example 2-furyl, aminomethylfuryl, for example 5-aminomethyl-2-furyl, 1,4-cyclohexadienyl, aminomethyl-1,4-cyclohexadienyl, for example 2-aminomethyl-1,4-cyclohexadienyl, 1-cyclohexenyl or aminomethyl-1-cyclohexenyl, for example 2-aminomethyl-1-cyclohexenyl, and, in the above radicals, hydroxyl and/or amino can be protected, for example by acyl, such as optionally halogenated lower alkoxycarbonyl, for example tert.-butoxycarbonyl or 2,2,2-trichloroethoxycarbonyl, $R_b$ represents hydrogen and $R_c$ represents hydrogen or amino, and also protected amino, such as acylamino, for example β-poly-branched lower alkoxycarbonylamino, such as tert.-butoxycarbonylamino, or 2-halogeno-lower alkoxycarbonylamino, for example 2,2,2-trichloroethoxycarbonylamino, 2-iodoethoxycarbonylamino or 2-bromoethoxycarbonylamino, or phenyl-lower alkoxycarbonylamino which is optionally substituted by lower alkoxy and/or nitro, for example 4-methoxybenzyloxycarbonylamino or diphenylmethoxycarbonylamino, or represents hydroxyl, as well as protected hydroxyl, such as acyloxy, for example β-poly-branched lower alkoxycarbonyloxy, such as tert.-butoxycarbonyloxy, or 2-halogen-lower alkoxycarbonyloxy, such as 2,2,2-trichloroethoxycarbonyloxy, 2-iodoethoxycarbonyloxy or 2-bromoethoxycarbonyloxy, or represents carboxyl or sulpho which are optionally esterified, for example with lower alkyl, or in which (2) $R_a$ represents cyano, 1-tetrazolyl, phenoxy or 4-pyridylthio and $R_b$ and $R_c$ represent hydrogen, or in which (3) $R_a$ represents phenyl, 2-thienyl or 2-furyl and $R_b$ and $R_c$ together denote syn-lower alkoxyimino, such as syn-methoxyimino, $R_1{}^b$ denotes hydrogen, $R_2$ above all represents hydroxyl and also represents methoxy, α-polybranched lower alkoxy, for example tert.-butoxy, 2-halogeno-lower alkoxy, for example 2,2,2-trichloroethoxy, 2-iodoethoxy or 2-bromoethoxy, or diphenylmethoxy which is optionally substituted, for example by lower alkoxy, such as methoxy, for example diphenylmethoxy or 4,4'-dimethoxydiphenylmethoxy, or 4-nitrobenzyloxy, pentachlorophenoxy and also tri-lower alkylsilyloxy, for example trimethylsilyloxy, as well as 2-lower alkenyloxy, for example allyloxy, and $R_3$ denotes hydrogen, lower alkyl with up to 4 carbon atoms, such as methyl or isopropyl, lower alkoxy-lower alkyl with up to 4 carbon atoms, for example methoxymethyl, or lower alkanoyloxy-lower alkyl with up to 4 carbon atoms, for example acetyloxymethyl, phenyl which is optionally substituted by nitro or amino, or benzyl, as well as salts, especially non-toxic salts which can be used pharmacologically, of such compounds having salt-forming groups, such as the alkali metal salts, for example sodium salts, or alkaline earth metal salts, for example calcium salts, or ammonium salts, including those with amines, of compounds of the formula I in which R$_2$ represents hydroxyl.

The invention relates above all to 6-acetylamino-2-R$_3$-2-penem-3-carboxylic acid compounds in which acetyl is substituted by the radicals R$_a$ and R$_b$ and (1) R$_a$ represents phenyl, 4-hydroxyphenyl or 1,4-cyclohexadienyl and R$_b$ represents hydrogen or amino which is optionally protected, for example as described above, or in which (2) R$_a$ represents phenoxy and R$_b$ represents hydrogen, and R$_3$ is hydrogen, methyl, methoxymethyl, acetyloxymethyl or phenyl, and also isopropyl, nitrophenyl or aminophenyl, and esters, especially lower alkyl esters, for example methyl or tert.-butyl esters, 2-lower alkenyl esters, for example allyl esters, nitrobenzyl esters, for example 4-nitrobenzyl esters, diphenylmethyl esters or pentachlorophenyl esters of such compounds, and the salts, especially the salts which can be used pharmacologically, of such compounds having salt-forming groups.

The new compounds can be manufactured by cyclising an ylide compound of the formula

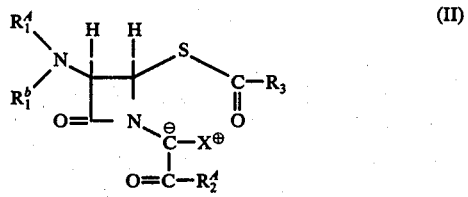

in which R$_1^A$, R$_1^B$, R$_2^A$ and R$_3$ have the abovementioned meanings and functional groups in these radicals are preferably in a protected form and in which X⊕ denotes either a trisubstituted phosphonio group or a di-esterified phosphono group together with a cation, and, if desired or necessary, in a resulting compound of the formula I, replacing the amino protective group R$_1^A$ by hydrogen and/or converting the protected carboxyl group of the formula —(=O)—R$_2^A$ into the free carboxyl group or into another protected carboxyl group and/or, if desired, converting a resulting compound of the formula I into the corresponding 1-oxide and, if desired, converting this into a compound of the formula I and/or, if desired, within the definition, converting a resulting compound of the formula I into another compound of the formula I and/or, if desired, converting a resulting compound having a salt-forming group into a salt or converting a resulting salt into the free compound or into another salt and/or, if desired, separating a resulting mixture of isomeric compounds into the individual isomers.

In a starting material of the formula II, the amino protective group R$_1^A$ preferably denotes an acyl group Ac, in which any free functional groups which may be present, for example amino, hydroxyl, carboxyl or sulpho groups, are protected in a manner which is in itself known, amino groups, for example, by the abovementioned acyl, trityl, silyl or stannyl radicals and also by substituted thio or sulphonyl radicals, and hydroxyl, carboxyl or sulpho groups by, for example, the abovementioned etherifying or esterifying groups, including silyl or stannyl groups, and R$_1^b$ preferably denotes hydrogen.

In a starting material of the formula II, R$_2^A$ preferably represents an etherified hydroxyl group which, with the —C(=O)— grouping forms an esterified carboxyl group which can be split easily, especially under mild conditions, and any functional groups which may be present in a carboxyl protective group R$_2^A$ can be protected in a manner which is in itself known, for example as indicated above. A group R$_2^A$ is, inter alia, lower alkoxy, especially α-poly-branched lower alkoxy, for example methoxy or tert.-butoxy, lower alkenyloxy, especially 2-lower alkenyloxy, for example allyloxy, or 2-halogeno-lower alkoxy, for example 2,2,2-trichloroethoxy, 2-bromoethoxy or 2-iodoethoxy, 2-lower alkylsulphonyl-lower alkoxy, for example 2-methylsulphonylethoxy, or an optionally substituted 1-phenyl-lower alkoxy group, such as a 1-phenyllower alkoxy group containing lower alkoxy, for example methoxy, or nitro, such as benzyloxy or diphenylmethoxy which are optionally substituted, for example as indicated, for example benzyloxy, 4-methoxybenzyloxy, 4-nitrobenzyloxy, diphenylmethoxy or 4,4'-dimethoxy-diphenylmethoxy, pentachlorophenoxy and also an organic silyloxy or stannyloxy group, such as tri-lower alkyl-silyloxy, for example trimethylsilyloxy.

In a starting material of the formula II, R$_3$ is, in particular, one of the preferred optionally substituted hydrocarbon radicals and functional groups are usually present in a protected form, amino, for example, also being present in the form of the nitro group.

The group X⊕ in a starting material of the formula II is one of the phosphonio or phosphono groups customary in Wittig condensation reactions, especially a triarylphosphonio group, for example a triphenylphosphonio group, or a tri-lower alkylphosphonio group, for example a tributylphosphonio group, or a phosphono group di-esterified by lower alkyl, for example ethyl, and in the case of the phosphono group, the symbol X⊕ additionally comprises the cation of a strong base, especially a suitable metal ion, such as an alkali metal ion, for example a lithium, sodium or potassium ion. Preferred groups X⊕ are, on the one hand, triphenylphosphonio and, on the other hand, diethylphosphono together with an alkali metal ion, for example a sodium ion.

In phosphonium compounds of the formula II, which in the isomeric ylene form are also termed phosphorane compounds, the negative charge is neutralised by the positively charged phosphonium group. In phosphono compounds of the formula II, which in their isomeric form can also be termed phosphonate compounds, the negative charge is neutralised by the cation of a strong base and, depending on the mode of manufacture of the phosphono starting material, this can be, for example, an alkali metal ion, for example a sodium, lithium or potassium ion. The phosphonate starting materials are therefore employed in the reaction as salts.

The formula II represents the starting material in the form in which cyclisation takes place. Usually, the corresponding phosphoranylidene compound of the formula

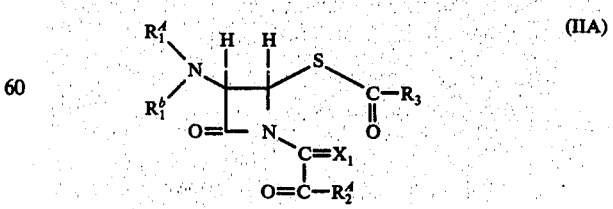

in which X$_1$ represents a trisubstituted phosphoranylidene radical, especially a triaryl-phosphoranylidene radical, for example a triphenyl-phosphoranylidene radical, or a tri-lower alkyl-phosphoranylidene radical, for example a tri-n-butylphosphoranylidene radical, or the corresponding phosphono compound of the formula

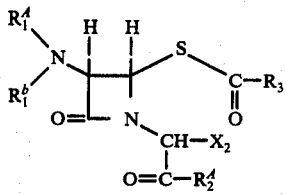

(IIB)

in which $X_2$ represents a phosphono group, especially a dialkylphosphono group, for example a diethylphosphono group, is employed and a phosphono starting material of the formula IIB is converted into the form suitable for cyclisation, that is to say into the compound of the formula II, by treatment with a suitable basic reagent, such as an inorganic base, for example an alkali metal carbonate, such as sodium carbonate or potassium carbonate, or an organic base, such as a tri-lower alkylamine, for example triethylamine, or a cyclic base of the amidine type, such as a corresponding diazabicycloalkene compound, for example 1,5-diaza-bicyclo[5.4.0]-undec-5-ene.

Preferred starting materials are the phosphoranylidene compounds of the formula IIA.

Cyclisation can take place spontaneously, that is to say during the manufacture of the starting materials, or by warming, for example in a temperature range of from about 30° C to about 120° C and preferably of from about 50° C to about 100° C.

The reaction is preferably carried out in the presence of a suitable inert solvent, such as in an aliphatic, cyclo-aliphatic or aromatic hydrocarbon, for example hexane, cyclohexane, benzene or toluene, a halogenated hydrocarbon, for example methylene chloride, an ether, for example diethyl ether, a lower alkylene glycol di-lower alkyl ether, for example dimethoxyethane or diethylene glycol dimethyl ether, a cyclic ether, for example dioxane or tetrahydrofurane, a carboxylic acid amide, for example dimethylformamide, a di-lower alkylsulphoxide, for example dimethylsulphoxide, or a lower alkanol, for example methanol, ethanol or tert.-butanol, or in a mixture thereof, and, if necessary, in an inert gas atmosphere, for example an argon atmosphere or a nitrogen atmosphere.

In a compound which is obtainable according to the invention it is possible, for example, to split off an amino protective group $R_1^A$ or $R_1^b$, especially an acyl group which can be split off, in a manner which is in itself known, for example to split off an α-poly-branched lower alkoxycarbonyl group, such as tert.-butoxycarbonyl, by treatment with trifluoroacetic acid and a 2-halogeno-lower alkoxycarbonyl group, such as 2,2,2-trichloroethoxycarbonyl or 2-iodoethoxycarbonyl, or a phenacyloxycarbonyl group by treatment with a suitable reducing metal or a corresponding metal compound, for example zinc or a chromium-II compound, such as chromium-II chloride or chromium-II acetate, advantageously in the presence of an agent which, together with the metal or the metal compound, generates nascent hydrogen, preferably in the presence of aqueous acetic acid, and a o-nitrophenoxyacetyl group by reduction of the nitro group, for example to the amino group by means of hydrogen and a palladium catalyst or to the hydroxylamino group by means of sodium borohydride, with subsequent cyclisation and spontaneous hydrolysis to the corresponding benzoxazin-2-one.

Furthermore, it is possible, in a resulting compound of the formula I, in which a carboxyl group of the formula $-C(=O)-R_2$ preferably represents a carboxyl group which is protected, for example by esterification, including by silylation, for example by reaction with a suitable organic halogenosilicon or halogeno-tin-IV compound, such as trimethylchlorosilane or tri-n-butyl-tin chloride, to split off an acyl group $R_1^A$ or $R_1^b$, in which any free functional groups which may be present are preferably in a protected form, by treatment with an imidehalide-forming agent, reaction of the resulting intermediate product with an alcohol and splitting of the imino-ether formed, it being possible for a protected carboxyl group, for example a carboxyl group protected by an organic silyl radical, already to be liberated in the course of the reaction.

Imide-halide-forming agents in which halogen is bonded to an electrophilic central atom are, above all, acid halides, such as acid bromides and especially acid chlorides. The acid halides are, above all, acid halides of inorganic acids, above all of phosphorus-containing acids, such as phosphorus oxyhalides and especially phosphorus pentahalides, for example phosphorus oxychloride and above all phosphorus pentachloride.

The reaction with one of the imide-halide-forming agents mentioned is carried out in the presence of a suitable base, especially of an organic base and above all of a tertiary amine, for example a secondary or tertiary aliphatic monoamine or diamine, such as a di-lower alkylamine or tri-lower alkylamine, for example diisopropylamine, triethylamine or N,N-diisopropyl-N-ethylamine, or of a dicycloalkylamine, for example dicyclohexylamine, of a monocyclic or bicyclic monoamine or diamine, of a tertiary aromatic amine or, above all, of a tertiary heterocyclic, monocyclic or bicyclic base, especially pyridine, preferably in the presence of a solvent, such as an optionally halogenated, for example chlorinated, aliphatic or aromatic hydrocarbon, for example methylene chloride. It is possible to use approximately equimolar amounts of the imide-halide-forming agent and of the base; however, the latter can also be present in more than or less than the equimolar amount. The reaction with the imidehalide-forming agent is preferably carried out with cooling, for example at temperatures of from about −50° C to about +10° C.

The intermediate product, which is usually further processed without isolation, is reacted, according to the process, with an alcohol, preferably in the presence of one of the above-mentioned bases, to give the imino-ether. Examples of suitable alcohols are aliphatic as well as araliphatic alcohols, above all lower alkanols which are optionally substituted, such as halogenated, for example chlorinated, or contain additional hydroxyl groups, for example ethanol, n-propanol or n-butanol, especially methanol. Usually an excess, for example an up to about 100-fold excess, of the alcohol, is used and the reaction is preferably carried out with cooling, for example at temperatures of from about −50° C to about 10° C.

The imino-ether product can advantageously be subjected to splitting without isolation. Splitting of the iminoether can be achieved by treatment with a suitable hydroxy compound, preferably by means of hydrolysis, and also by alcoholysis, and the latter can take place directly following the formation of the imino-ether, if an excess of the alcohol is used. Preferably, water or an alcohol, especially a lower alkanol, for example methanol, or an aqueous mixture of an organic solvent, such as an alcohol, is used. The reaction is usually carried out in an acid medium, for example at a pH value of about 1 to about 5, which can, if necessary, be obtained by adding a basic agent, such as an aqueous alkali metal hydroxide, for example sodium hydroxide or potassium hydroxide, or an acid, for example a mineral acid, or an organic acid, such as hydrochloric acid, sulphuric acid, phosphoric acid, fluoboric acid, trifluoroacetic acid or p-toluenesulphonic acid.

The three-stage process described above for splitting off an acyl group is advantageously carried out without isolation of the intermediate products, usually in the presence of an organic solvent which is inert with respect to the reactants, such as an optionally halogenated hydrocarbon, for example methylene chloride, and/or in an inert gas atmosphere, such as a nitrogen atmosphere.

If the intermediate product obtainable on treatment with the imide-halide-forming agent is reacted, instead of with an alcohol, with a salt, such as an alkali metal salt of a carboxylic acid, especially of a sterically hindered carboxylic acid, a compound of the formula I in which both the radicals $R_1^a$ and $R_1^b$ represent acyl groups is obtained.

In a compound of the formula I in which both of the radicals $R_1^A$ and $R_1^b$ represent acyl groups, one of these groups, preferably the sterically less hindered group, can be removed selectively, for example by hydrolysis or aminolysis.

In a compound of the formula I in which $R_1^A$ and $R_1^b$, together with the nitrogen atom, represent a phthalimido group, the latter can be converted into the free amino group, for example by hydrazinolysis, that is to say on treatment of such a compound with hydrazine.

A formyl group $R_1^A$ in a compound of the formula I, obtainable according to the invention, can also be split off by treatment with an acid agent, for example p-toluenesulphonic acid or hydrochloric acid, a weakly basic agent, for example dilute ammonia, or a decarbonylating agent, for example tris(triphenylphosphine)-rhodium chloride.

A triarylmethyl group $R_1^A$, such as the trityl group $R_1^A$, in a compound of the formula I, obtainable according to the invention, can be split off, for example, by treatment with an acid agent, such as a mineral acid, for example hydrochloric acid, or by hydrogenolysis, for example by treatment with hydrogen in the presence of a catalyst.

In a compound of the formula I which is obtainable according to the invention and has a protected, especially an esterified, carboxyl group of the formula —C(=O)—$R_2^A$, the latter can be converted into the free carboxyl group in a manner which is in itself known, for example in accordance with the nature of the group $R_2^A$. Thus, a carboxyl group esterified by a suitable 2-halogeno-lower alkyl group, an arylcarbonylmethyl group or a 4-nitrobenzyl group can be converted into the free carboxyl group, for example by treatment with a chemical reducing agent, such as a metal, for example zinc, or a reducing metal salt, such as a chromium-II salt, for example chromium-II chloride, usually in the presence of a hydrogen donor, which, together with the metal, is able to produce nascent hydrogen, such as an acid, above all acetic acid, as well as formic acid, or, in particular, of an alcohol, water preferably being added, and a carboxyl group esterified by an arylcarbonylmethyl group can also be converted into the free carboxyl group by treatment with a nucleophilic, preferably salt-forming, reagent, such as sodium thiophenolate or sodium iodide, and a carboxyl group esterified by 4-nitrobenzyl can also be converted into the free carboxyl group by treatment with an alkali metal dithionite, for example sodium dithionite. A carboxyl group esterified by a 2-lower alkylsulphonyl-lower alkyl group can be split, and liberated, for example by treatment with a basic agent and a carboxyl group esterified by a suitable arylmethyl grouping can be split, and liberated, for example by irradiation, preferably with ultraviolet light, for example below 290 mu, when the arylmethyl group represents, for example, a benzyl radical which is optionally substituted in the 3-, 4- and/or 5- position, for example by lower alkoxy and/or nitro groups, or with ultraviolet light of longer wave-length, for example above 290 mu, when the arylmethyl group denotes, for example, a benzyl radical which is substituted in the 2-position by a nitro group, and also a carboxyl group esterified by a suitably substituted methyl group, such as tert.-butyl or diphenylmethyl, can also be split, and liberated, for example, by treatment with a suitable acid agent, such as formic acid or trifluoroacetic acid, optionally with the addition of a nucleophilic compound, such as phenol or anisole, and an esterified carboxyl group which can be split hydrogenolytically, for example 4-benzyloxycarbonyl or 4-nitrobenzylcarbonyl, can be split, and liberated, by hydrogenolysis, for example by treatment with hydrogen in the presence of a noble metal catalyst, for example a palladium catalyst. Moreover, a carboxyl group which is esterified by a lower alkenyl group, such as by 2-lower alkenyl, especially allyl, and has the formula —C(=O)—$R_2^A$ can be converted into a formylmethoxycarbonyl group by oxidation, for example by treatment with ozone, followed by a reducing agent, such as an agent which forms the epoxy grouping, for example dimethylsulphide, and the carboxyl group can be liberated from the formylmethoxycarbonyl group by treatment with a base, such as a secondary amine, for example dimethylamine, or a 2-lower alkenyloxycarbonyl group, for example allyloxycarbonyl, can be isomerised, inter alia by treatment with tris-triphenylphosphine-rhodium chloride, palladium-on-charcoal or an alkali metal lower alkanolate, for example potassium tert.-butylate, in dimethylsulphoxide to give a 1-lower alkenyloxycarbonyl group and the latter can be split hydrolytically under weakly acid or weakly basic conditions. A pentachlorophenoxycarbonyl group can be converted into a free carboxyl group under mild conditions, for example by dilute sodium carbonate or sodium bicarbonate solution or by an organic base in the presence of water.

A carboxyl group protected, for example, by silylation or stannylation can be liberated in the customary manner by solvolysis, for example by treatment with water or an alcohol.

Resulting compounds of the formula I can be converted into other compounds of the formula I in a manner which is in itself known.

In a compound of the formula I in which $R_1^a$ and $R_1^b$ represent hydrogen, the free amino group can be substituted according to methods which are in themselves known, and above all can be acylated by treatment with acids, such as a carboxylic acid, or reactive derivatives thereof.

If a free acid in which any functional groups which may be present, such as an amino group which may be present, are preferably protected, is employed for the acylation, suitable condensing agents, such as carbodiimides, for example N,N'-diethyl-, N,N'-dipropyl-, N,N'-diisopropyl-, N,N'-dicyclohexyl- or N-ethyl-N'-3-dimethylaminopropyl-carbodiimide, suitable carbonyl compounds, for example carbonyldiimidazole, or isoxazolinium salts, for example N-ethyl-5-phenyl-isoxazolinium 3'-sulphonate and N-tert.-butyl-5-methyl-isoxazolinium perchlorate, or a suitable acylamino compound, for example 2-ethoxy-1-ethoxycarbonyl-1,2-dihydroquinoline, are customarily used. The condensation reaction is preferably carried out in an anhydrous reaction medium, for example in methylene chloride, dimethylformamide or acetonitrile.

An amide-forming functional derivative of an acid, in which groups which may be present, such as an amino group which may be present, are preferably protected, is, above all, an anhydride of such an acid, including, and preferably, a mixed anhydride. Mixed anhydrides are, for example, those with inorganic acids, especially with hydrogen halide acids, that is to say the corresponding acid halides, for example acid chlorides or acid bromides, and also with hydrazoic acid, that is to say the corresponding acid azides, with a phosphorus-containing acid, for example phosphoric acid or phosphorus acid, with a sulphur-containing acid, for example sulphuric acid, or with hydrocyanic acid. Further mixed anhydrides are, for example, those with organic acids, such as organic carboxylic acids, such as with lower alkanecarboxylic acids which are optionally substituted, for example by halogen, such as fluorine or chlorine, for example pivalic acid or trichloroacetic acid, or with half-esters, especially lower alkyl half-esters, of carbonic acid, such as the ethyl or isobutyl half-ester of carbonic acid, or with organic, especially aliphatic or aromatic, sulphonic acids, for example p-toluenesulphonic acid.

It is also possible to use, as acylating agents, inner anhydrides, such as ketenes, for example diketenes, isocyanates (that is to say inner anhydrides of carbamic acid compounds) or inner anhydrides of carboxylic acid compounds having carboxyl-substituted hydroxyl or amino groups, such as mandelic acid O-carboxanhydride or the anhydride of 1-N-carboxyamino-cyclohexanecarboxylic acid.

Further acid derivatives which are suitable for the reaction with the free amino group are activated esters, in which any functional groups which may be present are usually protected, such as esters with vinylogous alcohols (that is to say enols), such as vinylogous lower alkenols, or aryl esters, such as phenyl esters which are preferably substituted, for example by nitro or halogen, such as chlorine, for example pentachlorophenyl, 4-nitrophenyl or 2,4-dinitrophenyl esters, heteroaromatic esters, such as benztriazole esters, or diacylimino esters, such as succinylimino esters or phthalylimino esters.

Further acylation derivatives are, for example, substituted formimino derivatives, such as substituted N,N-dimethylchloroformimino derivatives of acids, or N-substituted N,N-diacylamines, such as a N,N-diacylated aniline.

The acylation with an acid derivative, such as an anhydride, and especially with an acid halide, can be carried out in the presence of an acid-binding agent, for example of an organic base, such as an organic amine, for example a suitable amine, such as a tri-lower alkylamine, for example triethylamine, a N,N-di-lower alkylaniline, for example N,N-dimethylaniline, or a base of the pyridine type, for example pyridine, of an inorganic base, for example an alkali metal hydroxide, carbonate or bicarbonate or an alkaline earth metal hydroxide, carbonate or bicarbonate, for example sodium hydroxide, carbonate or bicarbonate, potassium hydroxide, carbonate or bicarbonate or calcium hydroxide, carbonate or bicarbonate, or of an oxirane, for example a lower 1,2-alkylene oxide, such as ethylene oxide or propylene oxide.

The above acylation can be carried out in an aqueous or, preferably, non-aqueous solvent or solvent mixture, for example in a carboxylic acid amide, such as a N,N-di-lower alkylamide, for example dimethylformamide, a halogenated hydrocarbon, for example methylene chloride, carbon tetrachloride or chlorobenzene, a ketone, for example acetone, an ester, for example ethyl acetate, or a nitrile, for example acetonitrile, or mixtures thereof, and, if necessary, at lowered or elevated temperature and/or in an inert gas atmosphere, for example a nitrogen atmosphere.

In the above N-acylation reactions, it is possible to start from compounds of the formula I in which $R_2$ has the indicated meaning, and compounds having a free carboxyl group of the formula —C(=O)—$R_2$, in which $R_2$ represents hydroxyl, can also be used in the form of salts, for example ammonium salts, such as with triethylamine, or in the form of a compound which has a carboxyl group protected by reaction with a suitable organic phosphorus halide compound, such as with a lower alkylphosphorus dihalide or lower alkoxy-phosphorus dihalide, such as methyl-phosphorus dichloride, ethyl-phosphorus dibromide or methoxy-phosphorus dichloride; in the resulting acylation product, the protected carboxyl group can be liberated in a manner which is in itself known, for example as described above, including by hydrolysis or alcoholysis.

An acyl group can also be introduced by acylating a compound of the formula I, in which $R_1^a$ and $R_1^b$ together represent an ylidene radical (which can also be introduced subsequently, for example by treatment of a compound in which $R_1^a$ and $R_1^b$ represent hydrogen with an aldehyde, such as an aliphatic, aromatic or araliphatic aldehyde), for example according to the methods indicated above, and the acylation product can be hydrolysed, preferably in a neutral or weakly acid medium.

An acyl group can also be introduced stepwise. Thus, for example, it is possible to introduce into a compound of the formula I, having a free amino group in the 6-position, a halogeno-lower alkanoyl group, for example a bromoacetyl group, or, for example by treatment with a carbonic acid dihalide, such as phosgene, a halogenocarbonyl group, for example a chlorocarbonyl group, and to react a N-(halogeno-lower alkanoyl)-amino compound or N-(halogenocarbonyl)-amino compound, which is thus obtainable, with suitable exchange reagents, such as basic compounds, for example tetrazole, thio compounds, for example 2-mercapto-1-methylimidazole, or metal salts, for example sodium azide, or alcohols, such as lower alkanols, for example tert.-butanol, and thus to obtain substituted N-lower alkanoylamino or N-hydroxycarbonylamino compounds.

In both reactants, free functional groups can temporarily be protected during the acylation reaction in a manner which is in itself known and can be liberated, after the acylation, by means of methods which are in themselves known, for example as described above.

The acylation can also be effected by replacement of an already existing acyl group by another, preferably sterically hindered, acyl group, for example according to the process described above, by manufacturing the imide-halide compound, treating this with a salt of an acid and splitting off hydrolytically one of the acyl groups present in the product thus obtainable, usually the sterically less hindered acyl group.

It is furthermore possible, for example, to react a compound of the formula I in which $R_1{}^a$ represents a glycyl group which is preferably substituted in the $\alpha$-position, such as phenylglycyl, and $R_1{}^b$ represents hydrogen with an aldehyde, for example formaldehyde, or a ketone, such as a lower alkanone, for example acetone, and thus to obtain compounds of the formula I in which $R_1{}^a$ and $R_1{}^b$, together with the nitrogen atom, represent a 5-oxo-1,3-diaza-cyclopentyl radical which is preferably substituted in the 4-position and optionally substituted in the 2-position.

In a compound of the formula I in which $R_1{}^a$ and $R_1{}^b$ represent hydrogen, the free amino group can also be protected by introducing a triarylmethyl group, for example by treatment with a reactive ester of a triarylmethanol, such as trityl chloride, preferably in the presence of a basic agent, such as pyridine.

An amino group can also be protected by introducing a silyl and stannyl group. Such groups are introduced in a manner which is in itself known, for example by treatment with a suitable silylating agent, such as with a dihalogeno-di-lower alkyl-silane, lower alkoxy-lower alkyl-dihalogeno-silane or tri-lower alkyl-silyl halide, for example dichlorodimethylsilane, methoxy-methyl-dichlorosilane, trimethylsilyl chloride or dimethyl-tert.-butyl-silyl chloride, such silyl halide compounds preferably being used in the presence of a base, for example pyridine, or by treatment with an optionally N-mono-lower alkylated, N,N-di-lower alkylated, N-tri-lower alkylsilylated or N-lower alkyl-N-tri-lower alkyl-silylated N-(trilower alkylsilyl)-amine (see, for example, British Pat. No. 1,073,530), or with a silylated carboxylic acid amide, such as a bis-tri-lower alkylsilyl-acetamide, for example bis-trimethylsilyl-acetamide, or trifluorosilylacetamide, and also by treatment with a suitable stannylating agent, such as a bis-(trilower alkyl-tin) oxide, for example bis-(tri-n-butyl-tin) oxide, a tri-lower alkyl-tin hydroxide, for example triethyl-tin hydroxide, a tri-lower alkyl-lower alkoxy-tin compound, a tetra-lower alkoxy-tin compound or a tetra-lower alkyl-tin compound, and also with a tri-lower alkyl-tin halide, for example tri-n-butyl-tin chloride (see, for example, Netherlands Published Specification 67/11,107).

In a compound of the formula I which is obtainable according to the process and contains a free carboxyl group of the formula —C(=O)—$R_2$, such a group can be converted into a protected carboxyl group in a manner which is in itself known. Thus, esters are obtained, for example by treatment with a suitable diazo compound, such as a diazo-lower alkane, for example diazomethane or diazobutane, or a phenyl-diazo-lower alkane, for example diphenyldiazomethane, if necessary in the presence of a Lewis acid, such as, for example boron trifluoride, or by reaction with an alcohol suitable for the esterification process, in the presence of an esterifying agent, such as a carbodiimide, for example dicyclohexylcarbodiimide, as well as carbonyldiimidazole, and also with a N,N'-disubstituted O- or S-substituted isourea or isothiourea, in which a O-substituent and S-substituent are, for example, lower alkyl, especially tert.-butyl, phenyl-lower alkyl or cycloalkyl, and N-substituents or N'-substituents are, for example, lower alkyl, especially isopropyl, cycloalkyl or phenyl, or according to any other known and suitable esterification process, such as reaction of a salt of the acid with a reactive ester of an alcohol and of a strong inorganic acid, and also of a strong organic sulphonic acid. Furthermore, acid halides, such as acid chlorides (manufactured, for example, by treatment with oxalyl chloride), activated esters (formed, for example, with a N-hydroxynitrogen compound, such as N-hydroxy-succinimide) or mixed anhydrides (obtained, for example, with lower alkyl halogenoformates, such as ethyl chloroformate or isobutyl chloroformate) or with halogenoacetic acid halides, such as trichloroacetyl chloride) can be converted into an esterified carboxyl group by reaction with alcohols, optionally in the presence of a base, such as pyridine.

In a compound of the formula I having an esterified grouping of the formula —C(=O)—$R_2{}^A$, this grouping can be converted into another esterified carboxyl group of this formula, for example 2-chloroethoxycarbonyl or 2-bromoethoxycarbonyl can be converted into 2-iodoethoxycarbonyl by treatment with an iodine salt, such as sodium iodide, in the presence of a suitable solvent, such as acetone.

In a compound, obtainable according to the process, having a free carboxyl group of the formula —C(=O)—$R_2$, such a group can also be converted into an optionally substituted hydrazinocarbonyl group, for which preferably reactive functionally modified derivatives, such as the abovementioned acid halides, and generally esters, such as also the abovementioned activated esters, or mixed anhydrides of the appropriate acid are reacted with hydrazines.

A carboxyl group protected by an organic silyl or stannyl group can be formed in a manner which is in itself known, for example by treating compounds of the formula I in which $R_2$ represents hydroxyl, or salts, such as alkali metal salts, for example sodium salts, thereof, with a suitable silylating or stannylating agent, such as one of the abovementioned silylating or stannylating agents.

In the process according to the invention, and in additional measures which are optionally to be carried out or may require to be carried out, free functional groups which do not participate in the reaction are, if necessary, to be temporarily protected in a manner which is in itself known, such as free amino groups, for example, by acylation, tritylation or silylation, free hydroxyl groups, for example, by etherification or esterification and free carboxyl or sulpho groups, for example, by esterification, including silylation, and, after the reaction has taken place, these groups can, if desired, be liberated, individually or conjointly, in a manner which is in itself known. Thus, for example, amino, hydroxyl, carboxyl or sulpho groups present in an acyl radical $R_1{}^A$ or $R_1{}^b$ can be protected in the form of acylamino groups, such as those mentioned above, for example 2,2,2-trichloroethoxycarbonylamino, 2-bromoethoxycarbonylamino, 4-methoxybenzyloxycarbonylamino, diphenylmethoxycarbonylamino, p-nitrobenzyloxycarbonylamino or tert.-butoxycarbonylamino groups, of arylthioamino or aryl-lower alkylthioamino groups, for example 2-nitrophenylthioamino groups, or arylsulphonylamino groups, for example 4-methylphenylsulphonylamino groups, of 1-lower alkoxycarbonyl-2-propylideneamino groups or of o-nitrophenyloxyacetyl groups, or, respectively, of acyloxy groups, such as those mentioned above, for example tert.-butoxycarbonyloxy, 2,2,2-trichloroethoxycarbonyloxy or 2-bromoethoxycarbonyloxy groups, or, respectively, of esterified carboxyl groups, such as those mentioned above, for example diphenylmethoxycarbonyl or p-nitrobenzyloxycarbonyl groups, or, respectively, of substituted sulpho groups, such as the abovementioned lower alkylsulpho groups, for example methylsulpho groups, and subsequently liberated, if appropriate after conversion of the protective group; for example, it is possible, if desired, to split, for example partially, a 2,2,2-trichloroethoxycarbonylamino group or 2-iodoethoxycarbonylamino group or also a p-nitrobenzyloxycarbonylamino group by treatment with suitable reducing agents, such as zinc in the presence of aqueous acetic acid or hydrogen in the presence of a palladium catalyst, a diphenylmethoxycarbonylamino group or tert.-butoxycarbonylamino group by treatment with formic acid or trifluoroacetic acid, an arylthioamino group or aryl-lower alkylthioamino group by treatment with a nucleophilic reagent, such as sulphurous acid, an arylsulphonylamino group by means of electrolytic reduction, a 1-lower alkoxycarbonyl-2-propylideneamino group by treatment with an aqueous mineral acid, or, respectively, a tert.-butoxycarbonyloxy group by treatment with formic acid or trifluoroacetic acid, or a 2,2,2-trichloroethoxycarbonyloxy group or p-nitrobenzyloxycarbonyloxy group by treatment with a chemical reducing agent, such as zinc in the presence of aqueous acetic acid, or, respectively, a diphenylmethoxycarbonyl group by treatment with formic acid or trifluoroacetic acid or by hydrogenolysis, or, respectively, a substituted sulpho group by treatment with an alkali metal halide.

Furthermore, it is possible, in compounds of the formula I which contain, in the groups $R_1^A$, $R_1^b$, $R_2$ and/or $R_3$, the functional substituents, such as free amino, hydroxyl, carboxyl or sulpho groups, functionally to modify these substituents according to processes which are in themselves known, for example acylation or esterification or substitution. Thus, for example, an amino group can be converted into a sulphoamino group by treatment with sulphur trioxide, preferably in the form of a complex with an organic base, such as a tri-lower alkylamine, for example triethylamine. Furthermore, the reaction mixture obtained by reaction of an acid addition salt of a 4-guanyl semi-carbazide with sodium nitrite can be reacted with a compound of the formula I in which, for example, the amino protective group $R_1^A$ represents an optionally substituted glycyl group and the amino group can thus be converted into a 3-guanylureido group. Furthermore, compounds containing aliphatically bonded halogen, for example containing an optionally substituted α-bromoacetyl grouping, can be reacted with esters of phosphorous acid, such as tri-lower alkyl phosphite compounds and corresponding phosphono compounds can thus be obtained.

Furthermore, in obtainable compounds, functional substituents in radicals $R_1^A$, $R_1^b$, $R_2^A$ and/or $R_3$ can be converted into other functional groups and a nitro group can be converted into an amino group, for example, by treatment with hydrogen which has been activated catalytically, such as by means of a palladium catalyst.

Resulting 2-penem compounds of the formula I can be converted into their 1-oxides in a manner which is in itself known, by oxidation with suitable oxidising agents, such as hydrogen peroxide or per-acids, for example peracetic acid or 3-chloro-perbenzoic acid. Resulting 1-oxides of 2-penem compounds of the formula I can be reduced to the corresponding 2-penem compounds of the formula I in a manner which is in itself known, by reduction with suitable reducing agents, such as phosphorus trichloride. In these reactions care must be taken that, if necessary, free functional groups are protected, and, if desired, are subsequently liberated again.

Salts of compounds of the formula I can be manufactured in a manner which is in itself known. Thus, salts of those compounds which possess acid groups can be formed, for example, by treatment with metal compounds, such as alkali metal salts of suitable carboxylic acids, for example the sodium salt of α-ethylcaproic acid, or with ammonia or a suitable organic amine, preferably using stoichiometric amounts or only a small excess of the salt-forming agent. Acid addition salts of compounds of the formula I which possess basic groupings are obtained in the customary manner, for example by treatment with an acid or a suitable anion exchange reagent. Inner salts of compounds of the formula I, which contain, for example, a salt-forming amino group and a free carboxyl group, can be formed, for example, by neutralising salts, such as acid addition salts, to the isoelectric point, for example with weak bases, or by treatment with liquid ion exchangers. Salts of 1-oxides of compounds of the formula I which possess salt-forming groups can be manufactured in an analogous manner.

Salts can be converted into the free compounds in the customary manner, metal salts and ammonium salts, for example, by treatment with suitable acids and acid addition salts, for example, by treatment with a suitable basic agent.

Resulting mixtures of isomers can be separated into the individual isomers according to methods which are in themselves known, mixtures of diastereomeric isomers, for example, by fractional crystallisation, adsorption chromatography (column chromatography or thin layer chromatography) or other suitable separation methods. Resulting racemates can be resolved into the antipodes in the customary manner, if appropriate after introducing suitable salt-forming groupings, for example by forming a mixture of diastereomeric salts with optically active salt-forming agents, separating the mixture into the diastereomeric salts and converting the salts into the free compounds, or by fractional crystallisation from optically active solvents.

For all subsequent conversions of resulting compounds, the preferred reactions are those which take place under neutral or weakly basic conditions.

The process also comprises those embodiments according to which compounds arising as intermediate products are used as starting materials and the remaining process steps are carried out with these, or the process is discontinued at any stage; furthermore, starting materials can be used in the form of derivatives or can be formed during the reaction.

Preferably, the starting materials used and the reaction conditions chosen are such that the compounds mentioned initially as being particularly preferred are obtained.

The starting materials of the formula II, or IIA or IIB, which are used according to the invention, can be manufactured, for example, as follows and the following variant has proved particularly suitable for compounds in which $R_3$ differs from hydrogen:

A compound of the formula

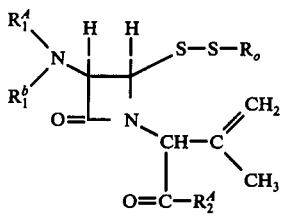

(III)

which can be obtained, for example, by converting a 6-amino-2,2-dimethyl-penam-3-carboxylic acid compound, in which the amino group and the carboxyl group are in a protected form, into the corresponding 1-oxide and reacting the latter with a suitable mercapto compound of the formula $R_o$-SH (IV), and in which $R_o$ represents a radical which is bonded via a carbon atom to the sulphur atom, especially a corresponding cyclic, and above all heterocyclic, radical, such as an azacyclic, diazacyclic, oxazacyclic or, preferably, thiazacyclic radical of aromatic character with 5 to 6 ring members, which optionally contains a fused benzene ring, for example 2-benzthiazolyl, is converted into the isomeric compound of the formula

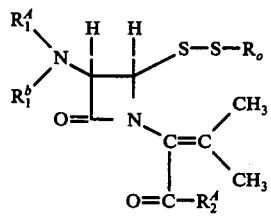

(V)

by treatment with a basic agent, such as an organic base, for example an amine, such as a tri-lower alkylamine, for example triethylamine, or an inorganic base.

The dithio compound of the formula V, which is thus obtainable, is treated with a reducing agent and, at the same time, or preferably subsequently, is reacted with a reactive acylation derivative of an acid of the formula $R_3$—C(=O)—OH (VI). Suitable reducing agents are, above all, hydride reducing agents, such as alkali metal borohydrides, for example sodium borohydride, and also phosphine compounds, such as a triarylphosphine, for example triphenylphosphine, and the hydride reducing agents are preferably used in the presence of suitable diluents, such as dimethylformamide, and in the absence of the acylating agent, which usually is employed subsequently, whilst the phosphine reducing agents are preferably used in the presence of the acylating agent and of suitable diluents, for example acetic acid. Suitable acylating agents are, in particular, anhyrides of the acid of the formula VI, such as symmetric anhydrides, for example anhydrides of lower alkanecarboxylic acids, such as acetic anhydride, or mixed anhydrides, preferably those with a hydrogen halide acid, that is to say the corresponding acid halides and above all acid chlorides or acid bromides.

In the acylthio compounds of the formula

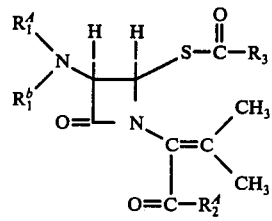

(VII)

which are thus obtainable, the 2-propylidene group is split off by treatment with ozone, followed by a reducing agent, and α-ketocarboxylic acid compounds of the formula $$\begin{array}{c} R_1^a \\ \diagdown \\ R_1^b \diagup N \end{array} \!\!\! \begin{array}{c} H \quad H \quad O \\ | \quad | \quad \| \\ \text{—C—C—S—C—}R_3 \\ | \quad | \\ O= \text{—N} \\ \diagdown \\ C=O \\ | \\ O=C-R_2^a \end{array}$$

(VIII)

are thus obtained. Usually, a ozone/oxygen mixture is used and the reaction is carried out in the presence of a solvent, such as a lower alkanol, for example methanol or ethanol, a lower alkanone, for example acetone, or an optionally halogenated aliphatic, cycloaliphatic or aromatic hydrocarbon, for example a halogeno-lower alkane, such as methylene chloride or carbon tetrachloride, or of a solvent mixture, including an aqueous mixture, and preferably with cooling, for example at temperatures of from about −90° C to about 0° C.

An ozonide, which is obtained as an intermediate product, is split, usually without being isolated, by reduction to give a compound of the formula VIII and for this reaction catalytically activated hydrogen, for example hydrogen in the presence of a heavy metal hydrogenation catalyst, such as a nickel catalyst and also a palladium catalyst, preferably on a suitable carrier, such as calcium carbonate or charcoal, or chemical reducing agents, such as reducing heavy metals, including heavy metal alloys or heavy metal amalgams, for example zinc, in the presence of a hydrogen donor, such as an acid, for example acetic acid, or of an alcohol, for example a lower alkanol, reducing inorganic salts, such as alkali metal iodides, for example sodium iodide, or alkali metal bisulphites, for example sodium bisulphite, in the presence of a hydrogen donor, such as an acid, for example acetic acid, or water, or reducing organic compounds, such as formic acid, are used. Compounds advantageously employed as reducing agents are those which are easily converted into corresponding epoxy compounds and the formation of the epoxide can take place as a result of a carbon-carbon double bond which is present or of an oxide-forming hetero-atom, such as a sulphur, phosphorus or nitrogen atom, which is present. Such compounds are, for example, suitably substituted ethene compounds (which during the reaction are converted into ethylene oxide compounds), such as tetracyanoethylene, then, in particular, suitable sulphide compounds (which during the reaction are converted into sulphoxide compounds), such as di-lower alkyl sulphides, above all dimethyl sulphide, suitable organic phosphorus compounds, such as a phosphine, which optionally can contain substituted aliphatic or aromatic hydrocarbon radicals as substituents (and which during the reaction is converted into a phosphine-oxide), such as tri-lower alkyl-phosphines, for example tri-n-butyl-phosphine, or triarylphosphines, for example triphenyl-phosphine, and also phosphites, which optionally contain substituted aliphatic hydrocarbon radicals as substituents (and during the reaction are converted into phosphoric acid triesters), such as tri-lower alkyl-phosphites, usually in the form of corresponding alcohol adduct compounds, such as trimethyl-phosphite, or phosphorous acid triamides which optionally contain substituted aliphatic hydrocarbon radicals as substituents, such as hexa-lower alkylphosphorous acid triamides, for example hexamethyl phosphorous acid triamide, the latter preferably in the form of a methanol adduct, and also suitable nitrogen bases (which during the reaction are converted into the corresponding N-oxides), such as heterocyclic nitrogen bases of aromatic character, for example bases of the pyridine type and in particular pyridine itself. Splitting of the ozonide, which is usually not isolated, normally takes place under the conditions which are employed for its manufacture, that is to say in the presence of a suitable solvent or solvent mixture and with cooling or slight warming, the reaction preferably being carried out at temperatures of from about −10° C to about +25° C and usually being brought to completion at room temperature.

A compound of the formula VIII can then be converted into a compound of the formula

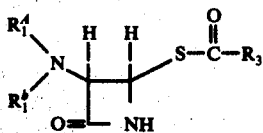 (IX)

by means of solvolysis. The solvolysis can be carried out as hydrolysis or, preferably, as alcoholysis and the reaction is usually carried out with a lower alkanol, for example methanol or ethanol and the alcoholysis is preferably carried out in the presence of water and of an organic solvent, such as a lower alkanecarboxylic acid lower alkyl ester, for example ethyl acetate, preferably at room temperature and, if necessary, with cooling or warming. The α-ketocarboxylic acid of the formula VIII does not necessarily need to be isolated. If, for example, splitting of the ozonide is carried out in the presence of a solvolysing agent such as, for example, water, a compound of the formula IX can be obtained direct.

A compound of the formula IX can also be obtained when a compound of the formula V is treated with a reducing agent, such as a suitable hydride reducing agent, especially an alkali metal borohydride, for example sodium borohydride, followed by a triarylmethyl halide, for example trityl bromide. In this way a compound of the formula

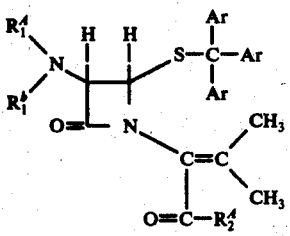 (X)

is obtained in which Ar represents an aryl radical, especially phenyl, and in which the 2-propylidene group is split off by oxidation, especially by treatment with ozone, followed by a suitable reducing agent, for example dimethyl sulphide. The solvolysis, especially alcoholysis, of a compound, manufactured in this way, of the formula

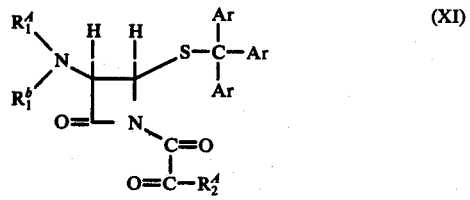 (XI)

for example by treatment of a compound of the formula XI with a lower alkanol, for example methanol, in the presence of water, gives a compound of the formula

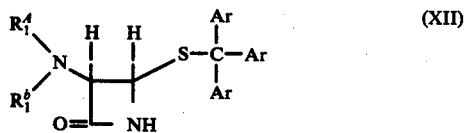 (XII)

in which the mercapto group is liberated, for example by treatment with a suitable heavy metal salt, for example silver-I nitrate, and conversion of the mercaptide which is thus obtainable, for example silver mercaptide, into the free mercapto compound in a manner which is in itself known, such as by forming a sparingly soluble heavy metal sulphide, for example silver-I sulphide, for example by treatment with hydrogen sulphide. In a compound of the formula

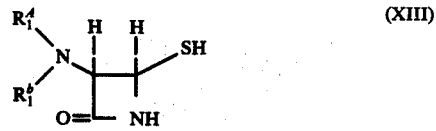 (XIII)

which is thus obtainable, the mercapto group is acylated by treatment with a suitable acylating agent, such as one of those mentioned above, for example an anhydride of an acid of the formula VI, and in this way a compound of the formula IX is obtained.

The acylation of a compound of the formula XIII is carried out by treatment with an acid HO—CO—R₃ or with a reactive functional derivative thereof, such as a halide, for example a chloride, an anhydride or an activated ester, for example a pentachlorophenyl ester or 4-nitrophenyl ester, if appropriate in the presence of a condensing agent, for example in the presence of a carbodiimide, such as N,N'-dicyclohexylcarbodiimide, when using an acid or in the presence of an acid-binding agent, for example an organic tertiary amine, such as triethylamine, diisopropylethylamine or pyridine when using an acid derivative, in a suitable solvent, such as a carboxylic acid amide, for example dimethylformamide, a halogenated hydrocarbon, for example methylene chloride, a ketone, for example acetone, an ester, for example ethyl acetate, or a nitrile, for example acetonitrile, or in an ether, for example tetrahydrofurane, at room temperature or, if necessary, at lowered or elevated temperature.

A compound of the formula XIII can also be obtained when the 2-propylidene group in a compound of the formula V is split off by oxidation, for example by treatment with ozone, followed by a reducing agent, for example dimethyl sulphide. In a compound of the formula

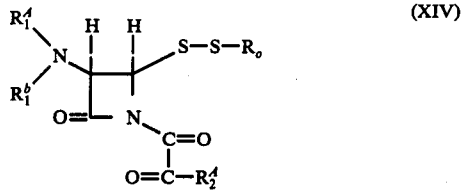

which is thus obtainable, the oxalyl grouping is removed by solvolysis, especially by alcoholysis, for example as described above, and in a compound of the formula

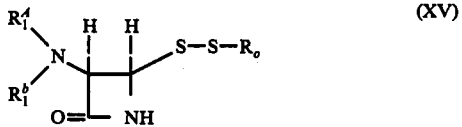

which is thus obtainable, the dithio grouping is split to the mercapto group by reduction, for example by treatment with a suitable hydride reducing agent, such as an alkali metal borohydride, for example sodium borohydride, followed by an acid reagent, for example trifluoroacetic acid or trimethylsilyl chloride, or alternatively by treatment with zinc in the presence of approximately 90% strength aqueous acetic acid.

A compound of the formula IX is reacted with a glyoxylic acid compound of the formula OHC—C(-=O)—$R_2^4$ (XVI) or a suitable deriative, such as a hydrate, hemi-hydrate or half-acetal, for example a half-acetal with a lower alkanol, for example methanol or ethanol, and this gives an α-hydroxycarboxylic acid compound of the formula

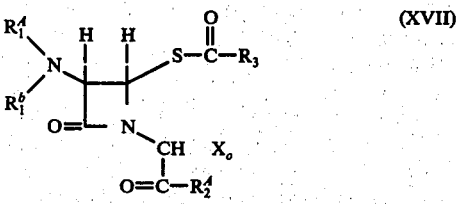

in which $X_o$ represents hydroxyl, which compound is usually obtained as a mixture of the two isomers but can also be isolated in the form of a pure isomer.

The addition reaction of the glyoxylic acid ester compound to the nitrogen atom of the lactam ring takes place at room temperature or, if necessary, with warming, for example up to about 100° C, and in particular takes place in the absence of an actual condensing agent and/or without the formation of a salt. When the hydrate of the glyoxylic acid compound is used, water is formed and, if necessary, this is removed by distillation, for example azeotropically, or by the use of a suitable dehydrating agent, such as a molecular sieve. Preferably, the reaction is carried out in the presence of a suitable solvent, such as, for example, dioxane, toluene or dimethylformamide, or of a solvent mixture, and, if desired or necessary, in an atmosphere of an inert gas, such as nitrogen.

A compound of the formula XVII, in which $X_o$ represents hydroxyl can also be obtained direct from a compound of the formula VIII, for example by reducing the oxo group by means of treatment of a compound of the formula VIII with a suitable reducing agent, such as a corresponding hydride reducing agent, especially with a borohydride, for example diborane, or an organic aluminium hydride, for example diisobutyl-aluminium hydride. The reduction is usually carried out in the presence of a solvent or diluent, for example tetrahydrofurane, and, if necessary, with cooling or warming and/or in an inert gas atmosphere.

In a compound of the formula XVII, the secondary hydroxyl group is converted into a reactive esterified hydroxyl group, especially into halogen, for example chlorine or bromine, or into an organic sulphonyloxy group, such as lower alkylsulphonyloxy, for example methylsulphonyloxy, or arylsulphonyloxy, for example 4-methylphenylsulphonyloxy; this gives compounds of the formula XVII in which $X_o$ represents a reactive esterified hydroxyl group, and in particular represents halogen or organic sulphonyloxy, and these compounds can be obtained in the form of mixtures of isomers or in the form of pure isomers.

The above reaction is carried out by treatment with a suitable esterifying agent by, for example, using a halogenating agent, such as a thionyl halide, for example thionyl chloride, a phosphorus oxyhalide, especially phosphorus oxychloride, or a halogenophosphonium halide, such as triphenylphosphine dibromide or triphenylphosphine diiodide, and also a suitable organic sulphonic acid halide, such as a sulphonic acid chloride, preferably in the presence of a basic agent, above all of an organic basic agent, such as an aliphatic tertiary amine, for example triethylamine, diisopropylethylamine or "polystyrene Hunig base", or a heterocyclic base of the pyridine type, for example pyridine or collodine. Preferably, the reaction is carried out in the presence of a suitable solvent, for example dioxane or tetrahydrofurane, or of a solvent mixture, and, if necessary, with cooling and/or in an atmosphere of an inert gas, such as nitrogen.

In a compound of the formula XVII which is thus obtainable, a reactive esterified hydroxyl group $X_o$ can be converted into another reactive esterified hydroxyl group in a manner which is in itself known. Thus, for example, a chlorine atom can be replaced by a bromine or iodine atom by treating the corresponding chlorine compound with a suitable bromine or iodine reagent, especially with an inorganic bromide or iodide salt, such as lithium bromide, preferably in the presence of a suitable solvent, such as ether.

A compound of the formula XVII in which $X_o$ represents a reactive esterified hydroxyl group is converted into the desired starting material of the formula II by treatment with a suitable phosphine compound, such as a tri-lower alkylphosphine, for example tri-n-butyl-phosphine, or a triaryl-phosphine, for example triphenylphosphine, or with a suitable phosphite compound, such as a tri-lower alkyl-phosphite, for example triethylphosphite, or an alkali metal dimethyl-phosphite, it being possible, depending on the choice of the reagent, to obtain a compound of the formula IIA or IIB.

The above reaction is preferably carried out in the presence of a suitable inert solvent, such as a hydrocarbon, for example hexane, cyclohexane, benzene or toluene, or an ether, for example dioxane, tetrahydrofurane or diethylene glycol dimethyl ether, or of a solvent mixture. If necessary, the reaction is carried out with cooling or at elevated temperature and/or in an atmosphere of an inert gas, such as nitrogen.

When a phosphine compound is used, the reaction is customarily carried out in the presence of a basic agent, such as an organic base, for example an amine, such as triethylamine, diisopropylethylamine or "polystyrene-Hunig base" and in this way the phosphoranylidene starting material of the formula IIA, which is formed from the corresponding phosphonium salt, is obtained direct.

The starting materials of the formula II in which $R_3$ represents hydrogen can be manufactured, for example, as follows:

A compound of the formula XV is reacted with a 3-phosphoranylidene-pyruvic acid ester of the formula $X_1=CH-C(=O)-C(=O)-R°$ (XVIII), in which $X_3$ can have the same meaning as $X_1$, such as a 3-triaryl-phosphoranylidene-pyruvic acid lower alkyl ester; a phosphoranylidene compound is thus obtained and this is present in the form of a 2-oxido-3-phosphonio-acrylic acid compound of the following formula:

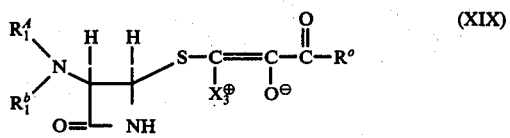

in which $X_3^{\oplus}$ represents a phosphonio group, espcially a triarylphosphonio group, and R° represents an etherified hydroxyl group, especially lower alkoxy. The reaction with the 3-phosphoranylidene-pyruvic acid ester is carried out in the presence of a suitable solvent, such as an ether, for example ethylene glycol dimethyl ether.

Reduction of a compound of the formula XIX, especially with a hydride reducing agent, such as an alkali metal borohydride, in an acid medium, for example in the presence of lower alkanecarboxylic acid or of mixtures of such acids, gives a compound of the formula

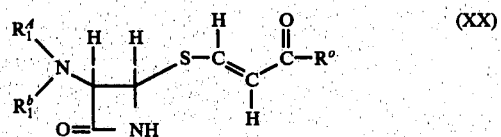

and this is reacted, for example as described above, with a glyoxylic acid ester of the formula XVI, or a derivative, such as a hydrate, thereof and a compound of the formula

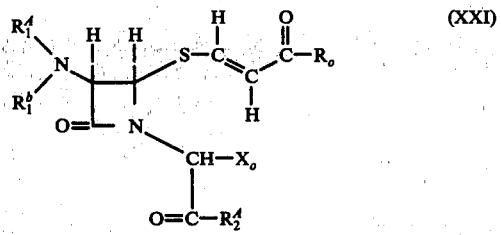

is thus obtained, in which $X_o$ represents hydroxyl. This hydroxyl can be converted, for example in the manner described above, into a reactive esterified hydroxyl group, such as a halogen atom or an organic sul-phonyloxy group, and in this way a compound of the formula XXI in which $X_o$ represents a reactive esterified hydroxyl group is obtained. On reaction with a phosphine, such as a triarylphosphine or tri-lower alkylphosphine, for example as described above, a compound of the formula

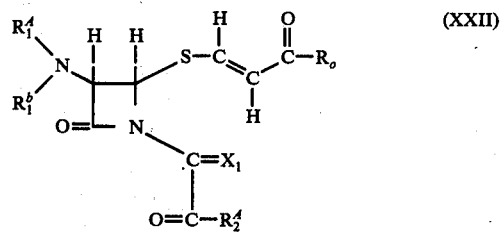

in which $X_1$ has the abovementioned meaning and above all represents a triaryl- or tri-lower alkyl-phosphoranylidene radical is obtained. A compound of the formula XXII is reacted, in the form of a phosphonium salt (which is manufactured by treating a compound of the formula XXII with an acid, for example an optionally substituted lower alkanecarboxylic acid, such as trifluoroacetic acid), in a manner analogous to the ozonisation of a compound of the formula VII to a compound of the formula VIII, with ozone in the presence of an acid, for example the acid with which the phosphonium salt has been produced, followed by a reducing agent, for example one of those mentioned above, and then with a basic agent, such as an inorganic base, for example an alkali metal bicarbonate, or with an organic base. This gives the starting material of the formula II, which is present in the form of the formula IIA and, under the reaction conditions necessary for manufacture, usually cyclises direct to give the desired compound of the formula I in which $R_3$ denotes hydrogen.

The invention also comprises the new intermediate products, such as those of the formulae XI, XII, XIV, XV, XVII, XIX, XX, XXI and XXII and especially of the formula IIA, VIII and IX, and also the processes for their manufacture.

The pharmacologically usable compounds of the present invention can, for example, be used for the manufacture of pharmaceutical formulations which contain an effective amount of the active substance together with, or mixed with, inorganic or organic, solid or liquid, pharmaceutically usable excipients which are suitable for enteral or parenteral administration. Thus, tablets or gelatine capsules are used which contain the active compund together with diluents, for example lactose, dextrose, sucrose, mannitol, sorbitol, cellulose and/or glycine, and lubricants, for example silica, talc, stearic acid or salts thereof, such as magnesium stearate or calcium stearate, and/or polyethylene glycol; tablets also contain binders, for example magnesium aluminium silicate, starches, such as corn starch, wheat starch, rice starch or arrowroot, gelatine, tragacanth, methylcellulose, sodium carboxymethylcellulose and/or polyvinylpyrrolidone, and, if desired, disintegrating agents, for example starches, agar, alginic acid or a salt thereof, such as sodium alginate, and/or effervescent mixtures, or adsorbents, dyestuffs, flavouring substances and sweeteners. Furthermore, the new pharmacologically active compounds can be used in the form of injectable formulations, for example formulations which can be administered intravenously, or of infusion solutions.

Such solutions are, preferably, isotonic aqueous solutions or suspensions and these can, for example, be manufactured before use from lyophilised formulations which contain the active substance by itself or together with an excipient, for example mannitol. The pharmaceutical formulations can be sterilised and/or contain auxiliaries, for example preservatives, stabilisers, wetting agents and/or emulsifiers, solubilising agents, salts for regulating the osmotic pressure and/or buffers. The present pharmaceutical formulations which can, if desired, contain further pharmacologically valuable substances, are manufactured in a manner which is in itself known, for example by means of conventional mixing, granulating, dragee-making, dissolving or lyophilising processes, and contain from about 0.1% to 100%, and especially from about 1% to about 50% of the active compound and lyophilised products contain up to 100% of the active compound.

In the context of the present description, the organic radicals described as "lower" contain, unless expressly defined, up to 7, and preferably up to 4, carbon atoms; acyl radicals contain up to 20, preferably up to 12 and above all up to 7, carbon atoms.

The examples which follow serve to illustrate the invention; temperature are given in degrees Centigrade.

EXAMPLE 1

A solution of 0.05 g of tert.-butyl 2-(4β-acetylthio2-oxo-3β-phenoxyacetylamino-1-azetinyl)-2-triphenylphosphoranylidene acetate in 50 ml of toluene is warmed at 70° for 10 hours and during this time argon is passed slowly through the solution. The solvent is evaporated under reduced pressure and the residue is subjected to preparative layer chromatography on silica gel (Merck, analytical grade; three plates 20 cm in length, 20 cm in breadth and 0.025 cm thick), for which a 1:1 mixture of benzene and ethyl acetate is used. This gives pure amorphous tert.-butyl 2-methyl-6β-phenoxyacetylamino-2-penem-3-carboxylate of the formula

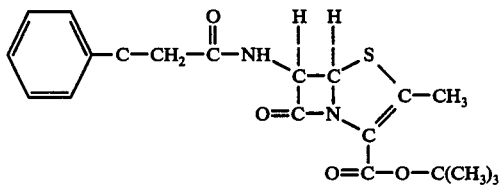

Rf = 0.53; ultraviolet absorption spectrum (in ethanol): $\lambda_{max}$ = 305 mμ, 275 mμ, 268 mμ and 263 mμ; infrared absorption spectrum (in methylene chloride): characteristic bands at 2.98μ, 3.32μ, 3.41μ, 3.45μ (shoulder), 5.57μ, 5.90μ, 6.27μ, 6.60μ, 6.71μ, 6.97–7.08μ and 7.33μ; $[\alpha]_D^{20}$ = +202° ± 1° (c = 0.567 in chloroform).

The starting material can be prepared as follows:

a. A solution of 36.6 g of the 1β-oxide of 6β-phenoxyacetylamino-penam-3-carboxylic acid, 11.1 ml of triethylamine and 23.8 g of 4-nitrobenzyl bromide in 200 ml of dimethylformamide is stirred for 4 hours at room temperature under nitrogen. The reaction solution is then introduced into 1,500 ml of ice water and the precipitate is filtered off, dried and twice recrystallised from a mixture of ethyl acetate and methylene chloride. The colourless, crystalline 1β-oxide of 4-nitrobenzyl 6β-phenoxyacetylamino-penam-3-carboxylate melts at 179°–180°.

b. A solution of 5.01 g of the 1β-oxide of 4-nitrobenzyl 6β-phenoxyactylamino-penam-3-carboxylate and 1.67 g of 2-mercapto-benzthiazole in 110 ml of dry toluene is boiled under reflux in a nitrogen atmosphere for 4 hours. The solution is concentrated to a volume of about 25 ml by distilling off and is diluted with about 100 ml of diethyl ether. The product which has separated out is recrystallised from a mixture of methylene chloride and diethyl ether and this gives 4-nitrobenzyl 2-[4β-(2-benzthiazolyl-dithio)-3β-phenoxyacetylamino-2-oxo-1-azetidinyl]-2-(1-propen-2-yl)-acetate, melting point 138°–141°.

c. 9.9 g of 4-nitrobenzyl 2-[4β-(2-benzthiazolyl-dithio)-3β-phenoxyacetylamino-2-oxo-1-azetidinyl]-2-(1-propen-2-yl)-acetate are dissolved in 200 ml of warm ethylene glycol dimethyl ether, 5 ml of triethylamine are added and the solution is stirred for 75 minutes at room temperature. The solvent is evaporated under reduced pressure; toluene is added and the mixture is again evaporated under reduced pressure. The crude product is chromatographed on hydrochloric acid-washed silica gel; solvent: toluene/ethyl acetate, 3:2. 4-Nitrobenzyl 2-[4β-(2-benzthiazolyl-dithio)-2-oxo-3β-phenoxyacetylamino-1-azetidinyl]-2-(2-propylidene)-acetate, which is obtained as a virtually white crystalline foam, is recrystallised from a mixture of methylene chloride and diethyl ether. Despite the melting point range of 105°–115°, the product is homogeneous according to thin layer chromatography (silica gel; toluene/ethyl acetate, 60:40); $[\alpha]_D^{20}$ = −15° ± 1° (c = 0.908% in chloroform); ultraviolet absorption spectrum (in ethanol): $\lambda_{max}$ = 268 mμ (ε = 24,200); infrared absorption spectrum (in methylene chloride): characteristic bands at 2.92μ, 5.61μ, 5.78μ and 5.90μ.

d. A solution of 0.897 g of 4-nitrobenzyl 2-[4β-(2-benzthiazolyl-dithio)-2-oxo-3β-phenoxyacetylamino-1-azetidinyl]-2-(2-propylidene)-acetate in 14 ml of dimethylformamide is added dropwise, over a period of 10 minutes, to a solution of 0.076 g of sodium borohydride in 10 ml of dimethylformamide, under a nitrogen atmosphere and whilst cooling in a methanol/ice bath. 7 ml of freshly distilled acetyl bromide are then added. The reaction mixture is stirred for 60 minutes at 0°, diluted with 350 ml of benzene and washed several times with, in each case, 100 ml of water. The mixture is dried over sodium sulphate and the solvent is evaporated under reduced pressure. The residue is chromatographed in a column containing 50 g of silica gel, benzene being used as the solvent. The fractions containing benzene and a 9:1 mixture of benzene and ethyl acetate are discarded; the desired 4-nitrobenzyl 2-(4β-acetylthio-2-oxo-3β-phenoxyacetylamino-1-azetidinyl)-2-(2-propylidene)-acetate is washed out with a 4:1 mixture of benzene and ethyl acetate and the crude product is subjected to preparative thin layer chromatography (silica gel) and a 2:1 mixture of benzene and ethyl acetate is used. The product is obtained in an amorphous form; thin layer chromatography (silica gel): Rf = 0.45 (benzene/ethyl acetate, 1:1); infrared absorption spectrum (in methylene chloride): characteristic bands at 2.95μ, 3.30μ, 3.35–3.55μ, 5.63μ, 5.80μ (shoulder), 5,89μ, 6.15μ, 6.25μ, 6.31μ, 6.45μ, 6.97μ, 7.08μ, 7.18μ, 7.32μ and 7.43μ.

di. The above product can also be obtained as follows: a solution of 0.0663 g of 4-nitrobenzyl 2-[4β-(2-benzthiazolyldithio)-2-oxo-3β-phenoxyacetylamino-1-azetidinyl]-2-(2-propylidene)-acetate and 0.027 g of triphenylphosphine in 1.5 ml of acetic anhydride and 0.5 ml of acetic acid is stirred for one hour at room temperature under a nitrogen atmosphere. The solvent is evaporated under reduced pressure and the residue is purified by means of preparative thin layer chromatography (silica gel; benzene/ethyl acetate, 3:1). This gives pure 4-nitrobenzyl 2-(4β-acetylthio-2-oxo-3β-phenoxyacetylamino-1-azetidinyl)-2-(2-propylidene)-acetate.

e. A solution of 0.24 g of 4-nitrobenzyl 2-(4β-acetylthio 3-oxo-3β-phenoxyacetylamino-1-azetidinyl)-2-(2-propylidene)-acetate in 20 ml of methyl acetate is cooled to −78° and a mixture of ozone and oxygen is passed through at such a rate that 0.1 mmol of ozone passes into the mixture per minute. After passing in 1.5 equivalents of ozone, the supply of the gas mixture is discontinued and the mixture is left to stand for 15 minutes at −78°. The excess ozone is driven off by passing in nitrogen and the reaction mixture is treated with 1 ml of dimethyl sulphide. The mixture is left to stand in a closed vessel for 16 hours at room temperature. The volatile constituents are evaporated under reduced pressure and the crystalline residue is recrystallised from a mixture of methylene chloride and diethyl ether. The virtually colourless 4-nitrobenzyl 2-(4β-acetylthio-2-oxo-3β-phenoxyacetylamino-1-azetidinyl)-2-oxo-acetate melts at 154°–156°; $[\alpha]_D^{20} = -13° \pm 1°$ ($c = 0.984\%$ in chloroform); infrared absorption spectrum (in methylene chloride): characteristic bands at 2.95μ, 3.20–3.45μ, 5.48μ, 5.69μ, 5.87μ, 6.25μ, 6.58μ, 6.71μ, 6.95–7.08μ, 7.25μ and 7.45μ.

f. A solution of 2.78 g of crude 4-nitrobenzyl 2-(4β-acetylthio-2-oxo-3β-phenoxyacetylamino-1-azetidinyl)-2-oxo-acetate in 55 ml of methyl acetate is diluted with 500 ml of methanol and 11 ml of water; it is left to stand for 18 hours at room temperature and evaporated under reduced pressure. The residue is chromatographed on 300 g of silica gel and monomethyl mono-4-nitrobenzyl oxalate and other impurities are washed out with a 4:1 mixture of benzene and ethyl acetate. 4β-Acetylthio-3β-phenoxyacetylamino-azetidin-2-one is eluted with a 1:1 mixture of benzene and ethyl acetate. The product is recrystallised from a mixture of methylene chloride and diethyl ether; melting point 137.5°–138.5°; thin layer chromatography (silica gel): Rf = 0.20 (benzene/ethyl acetate, 1:1); infrared absorption spectrum (in methylene chloride): characteristic bands at 2.96μ, 3.28–3.40μ, 5.61μ, 5.92μ, 6.27μ, 6.60μ, 6.71μ, 6.97μ and 7.08μ (shoulder).

g. A solution of 0.294 g of 4β-acetylthio-3β-phenoxyacetylamino-azetidin-2-one and 0.495 g of tert.-butyl glyoxylate hydrate in 10 ml of toluene and 2.5 ml of dimethylformamide is stirred for one hour at room temperature in the presence of sodium aluminium silicate molecular sieves (Union Carbide type A3; pore diameter 3A; activated at 250° and under a pressure of 0.01 mm Hg) and the mixture is then filtered. The filtrate is taken to dryness under reduced pressure. Toluene is added to the residue and the mixture is again evaporated under a high vacuum; this procedure is repeated several times. This gives a mixture of the two isomers of tert.-butyl 2-(4β-acetylthio-2-oxo-3β-phenoxyacetylamino-1-azetidinyl)-2-hydroxy-acetate, thin layer chromatogram (silica gel): Rf ∼ 0.25 (ethyl acetate/benzene, 1:1); infrared absorption spectrum (in methylene chloride): characteristic bands at 2.85–3.15μ, 2.97μ, 3.30–3.50μ, 5.61μ, 5.75μ, 5.90μ, 6.25μ, 6.60μ, 6.70μ, 6.98μ, 7.07μ (shoulder) and 7.32μ. The product is employed in the next step without purification.

h. 0.3 g of thionyl chloride and 1 g of "polystyrene Hunig base" (prepared by warming a mixture of 100 g of chloromethylpolystyrene (J. Am. Chem. Soc., volume 85, page 2,149 (1963)], 500 ml of benzene, 200 ml of methanol and 100 ml of diisopropylamine to 150°, whilst shaking, and filtering, washing the product with 1,000 ml of methanol, 1,000 ml of a 3:1 mixture of dioxane and triethylamine, 1,000 ml of methanol, 1,000 ml of dioxane and 1,000 ml of methanol and drying for 16 hours at 100°/10 mm Hg; the product neutralises 3.34 milliequivalents of hydrochloric acid per gram in a 2:1 mixture of dioxane and water and is suspended in dioxane for 30 minutes before use) are added to a mixture of 0.455 g of the crude tert.-butyl 2-(4β-acetylthio-2-oxo-3β-phenoxyacetylamino-1-azetidinyl)-2-hydroxy-acetate in 15 ml of dioxane and the reaction mixture is stirred for 3 hours at room temperature and then filtered. The filtrate is evaporated under reduced pressure. This gives amorphous, almost pure tert.-butyl 2-(4β-acetylthio-2-oxo-3β-phenoxyacetylamino-1-azetidinyl)-2-chloro-acetate, which probably is in the form of a mixture of the two isomers; thin layer chromatogram (silica gel): Rf = 0.52 (ethyl acetate/benzene, 1:1); infrared absorption spectrum (in methylene chloride): characteristic bands at 2.96μ, 3.25–3.50μ, 5.59μ, 5.74μ, 5.89μ, 6.25μ, 6.60μ, 6.71μ, 6.96μ, 7.32μ and 7.60μ. The product is further processed without further purification.

i. A solution of 0.452 g of tert.-butyl 2-(4β-acetylthio-2-oxo-3-phenoxyacetylamino-1-azetidinyl)-2-chloro-acetate and 0.393 g of triphenylphosphine in 15 ml of dioxane is warmed, in the presence of 1.0 of "polystyrene-Hunig base" (suspended in dioxane for 30 minutes before use), to 50° for 18 hours, under a nitrogen atmosphere, and then filtered and the filtrate is evaporated under reduced pressure. The residue is subjected to preparative thin layer chromatography (silica gel plates 20 cm in length, 20 cm in breadth and 0.15 cm thick) and a 1:1 mixture of benzene and ethyl acetate is used. This gives pure and amorphous tert.-butyl 2-(4β-acetylthio-2-oxo-3β-phenoxyacetylamino-1-azetidinyl)-2-triphenylphosphoranylidene acetate; thin layer chromatography (silica gel): Rf = 0.21 (benzene/ethyl acetate, 1:1); infrared absorption spectrum (in methylene chloride): characteristic bands at 2.98μ, 3.31μ, 3.40μ, 5.68μ, 5.92μ, 6.11μ, 6.20μ (shoulder), 6.28μ (shoulder), 6.34μ (shoulder), 6.60μ, 6.72μ, 6.98μ, 7.07μ (shoulder) and 7.35μ.

EXAMPLE 2

5 ml of a 10% strength solution of trifluoroacetic acid in methylene chloride are added to a solution of 0.0725 g of ethyl trans-3-[2-oxo-3β-phenoxyacetylamino-1-(tert.-butoxycarbonyl-triphenylphosphoranylidenemethyl)-4β-azetidinyl-thio]-acrylate in 4 ml of methylene chloride, whilst cooling in a solid carbon dioxide/carbon tetrachloride bath (about −20°). The resulting solution is treated, at −20°, with one equivalent of ozone (in the form of a mixture of ozone and oxygen) in the course of one minute. The mixture is left to stand at this temperature for 3 minutes and is then degassed with nitrogen. The reaction mixture is then treated with 0.5 ml of dimethyl sulphide. The mixture is left to stand for 5 minutes without cooling, then diluted with about 20 ml of methylene chloride and washed with an 8% strength aqueous solution of sodium bicarbonate, whereupon tert.-butyl 2-(4β-formylthio-2-oxo-3β-phenoxyacetylamino-1-azetidinyl)-2-triphenylphosphoranylideneacetate forms, and with a saturated aqueous solution of sodium chloride. The mixture is dried over sodium sulphate and the volatile constituents are evaporated under reduced pressure. The residue is filtered chromatographically through 10 g of silica gel (treated with 1:1 hydrochloric acid and washed with water), the solvent used being a 4:1 mixture of benzene and ethyl acetate. This gives pure, crystalline tert.-butyl 6β-phenoxyacetylamino-2-penem-3-carboxylate of the formula

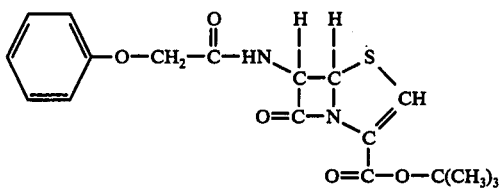

melting point 99°-102°; $[\alpha]_D^{20} = +206° \pm 1°$ ($c = 0.740\%$ in chloroform); thin layer chromatogram (silica gel): RF = 0.50 (benzene/ethyl acetate, 1:1); ultraviolet absorption spectrum (in ethanol): $\lambda_{max} = 308$ mμ, 275 mμ, 268 mμ and 262mμ; infrared absorption spectrum (in methylene chloride): characteristic bands at 2.98μ; 3.29–3.50μ, 5.54μ, 5.87μ, 6.25μ, 6.28μ (shoulder), 6.40μ, 6.61μ, 6.71μ, 6.97μ, 7.07μ (shoulder), 7.21μ, 7.32μ, 7.48μ and 7.62μ.

The starting material can be prepared as follows:

a. A solution of 1.95 g of 4-nitrobenzyl 2-[4β-(2-benzthiazolyl-dithio)-2-oxo-3β-phenoxyacetylamino-1-azetidinyl]-2-(2-propylidene)-acetate in 150 ml of methyl acetate is so treated with an ozone/oxygen mixture that 0.1 mmol of ozone is passed through per minute and during this treatment the mixture is cooled in a solid carbon dioxide/acetone bath. After 38 minutes, introduction of the ozone/oxygen mixture is discontinued and after a further 15 minutes at −78° the excess ozone is driven off by passing through nitrogen and the temperature is allowed to rise to about 0°. The cold reaction mixture is then washed with 45 ml of an ice-cold 10% strength aqueous solution of sodium bisulphite and with twice 50 ml of a saturated aqueous solution of sodium chloride; the wash solutions are back-washed with about 80 ml of methyl acetate. The combined organic solutions are dried over sodium sulphate and evaporated under reduced pressure. The crystalline residue is recrystallised from warm methylene chloride with partial evaporation of the solvent. 4-Nitrobenzyl 2-[4β-(2-benzthiazolyl-dithio)-2-oxo-3β-phenoxyacetylamino-1-azetidinyl]-2-oxo-acetate, which is thus obtainable, melts at 130°-131°; infrared absorption spectrum (in methylene chloride): characteristic bands at 2.98μ, 3.25–3.50μ, 5.49μ, 5.70μ, 5.87μ, 5.92μ (shoulder), 6.25μ, 6.57μ, 6.71μ, 6.87μ; 6.96μ (shoulder), 7.08μ, 7.25μ and 7.42μ.

b. A mixture of 1.8 g of the crude 4-nitrobenzyl 2-[4β-(2-benzthiazolyl-dithio)-2-oxo-3β-phenoxyacetylamino-1-azetidinyl]-2-oxo-acetate, 220 ml of methanol, 30 ml of methyl acetate and 4.4 ml of water is boiled under reflux for 20 minutes. The volatile constituents are evaporated under reduced pressure and the residue is chromatographed on 100 g of silica gel, a 4:1 mixture of benzene and ethyl acetate being used as the solvent. Monomethyl mono-4-nitrobenzyl oxalate is isolated in the first fractions. Using ethyl acetate, 4β-(2-benzthiazolyl-dithio)-3β-phenoxyacetylaminoazetidin-2-one is obtained and after recrystallisation from a mixture of methylene chloride and diethyl ether this melts, in the form of colourless crystals, at 143°-145°; thin layer chromatogram (silica gel): Rf = 0.26 (benzene/ethyl acetate, 1:1); infrared absorption spectrum (in methylene chloride): characteristic bands at 2.96μ, 5.59μ, 5.91μ, 6.25μ, 6.60μ, 6.70μ, 6.85μ, 6.97μ, 7.08μ, 8.12μ, 8.20 μ (shoulder), 8.28μ (shoulder), 9.26μ and 9.45μ.

c. A solution of 0.3156 g of 4β-(2-benzthiazolyl-dithio)-3β-phenoxyacetylamino-azetindin-2-one in 35 ml of ethylene glycol dimethyl ether is treated, at a temperature of −20°, with a solution of 0.3 g of the ethyl ester of 3-triphenylphosphoranylidene-pyruvic acid in 35 ml of ethylene glycol dimethyl ether; the reaction mixture is left to stand for 3 days at room temperature under a nitrogen atmosphere. The solvent is evaporated under reduced pressure and the residue is chromatographed on 20 g of silica gel. 2-Mercapto-benzthiazole is washed out in several fractions using a 3:1 mixture of benzene and ethyl acetate; ethyl 2-oxido-3-(2-oxo-3β-phenoxyacetylamino-4β-azetidinylthio)-3-triphenylphosphonioacrylate is eluted in three fractions using ethyl acetate and the pure product is obtained in the middle fraction. The first and third fraction are subjected to preparative thin layer chromatography, ethyl acetate being used as the solvent; this gives a further amount of the amorphous product; infrared absorption spectrum (in methylene chloride): characteristic bands at 2.96μ, 3.25–3.50μ, 5.63μ, 5.83μ (shoulder), 5.91μ, 6.27μ, 6.48μ, 6.60μ (shoulder), 6.72μ, 6.97μ, 7.07μ, 7.50μ, 8.36μ and 9.08μ.

d. The ethyl ester of 3-triphenylphosphoranylidenepyruvic acid, which is used in the above process step, can be obtained as follows: a solution of 10.5 g of triphenylphosphine in 75 ml of methylene chloride is treated, whilst stirring at a temperature of 0°, with a solution of 7.8 g of the ethyl ester of 3-bromopyruvic acid in 75 ml of methylene chloride. The mixture is stirred at room temperature for 90 minutes and the solvent is then evaporated under reduced pressure. The residue is partitioned between 150 ml of water, about 50 ml of tetrahydrofurane and 100 ml of pentane. The aqueous phase is washed twice with pentane, diluted with 50 ml of an 8% strength aqueous solution of sodium bicarbonate and extracted with methylene chloride. The methylene chloride extract solution is dried over sodium sulphate and evaporated under reduced pressure. The crystalline residue is recrystallised from acetone and gives the ethyl ester of 3-triphenylphosphoranylidene-pyruvic acid, melting point 187°; infrared absorption spectrum (in methylene chloride): characteristic bands at 3.32μ, 3.40μ, 5.78μ (shoulder), 5.85μ, 6.33μ (shoulder), 6.40μ, 6.75μ, 6.97μ, 8.20μ (broad) and 9.05μ.

e. 0.135 g of sodium borohydride is added, in small portions, in the course of 25 minutes to a solution of 0.117 g of ethyl 2-oxido-3-(2-oxo-3β-phenoxyacetylamino-4β-azetidinylthio)-3-triphenylphosphonio-acrylate in 2 ml of acetic acid, 1 ml of propionic acid and 0.2 ml of formic acid, whilst cooling in an ice/water bath, and during the addition the mixture is stirred vigorously. The reaction mixture is concentrated under reduced pressure at 20° to 30° and partitioned between methylene chloride and a 25% strength aqueous solution of ammonium chloride. The organic phase is dried and evaporated and the residue is subjected to preparative plate chromatography (silica gel), ethyl acetate being used as the solvent. This gives ethyl trans-3-(2-oxo-3β-phenoxyacetylamino-4β-azetidinyl-thio)- acrylate, which after recrystallisation from a mixture of methylene chloride and diethyl ether melts at 109°–112°; thin layer chromatogram (silica gel): Rf = 0.44 (ethyl acetate); ultraviolet absorption spectrum: $\lambda_{max}$ = 275 mµ, with an inflection at 272 mµ (in ethanol) and $\lambda_{max}$ = 315 mµ (in a solution of potassium hydroxide in ethanol); infrared absorption spectrum (in methylene chloride): characteristic bands at 2.95µ, 3.25–3.45µ, 5.60µ, 5.89µ, 6.29µ, 6.60µ, 6.71µ, 6.98µ, 7.09µ (shoulder), 7.35µ, 7.70µ, 7.84µ (shoulder), 8.11µ, 8.29µ, 8.55µ (broad), 9.25µ, 9.44µ and 9.70µ.

f. A solution of 0.24 g of ethyl trans-3-(2-oxo-3β-phenoxyacetylamino-4β-azetidinyl-thio)-acrylate and 0.34 g of the hydrate of tert.-butyl glyoxalate in 8 ml of toluene and 2 ml of dimethylformamide is stirred at room temperature in the presence of sodium aluminium silicate molecular sieves (Union Carbide type 3A, pore size 3A; activated at 250°/0.01 mm Hg) and after 3 hours the mixture is filtered. The filter residue is washed with toluene, the filtrate is evaporated under reduced presure and, after adding toluene, the residue is finally taken to dryness at about 40° and under the pressure of an oil vacuum pump. This gives amorphous ethyl trans-3-[2-oxo-3β-phenoxyacetylamino-1-(tert.-butoxycarbonyl-hydroxymethyl-4β-azetidinylthio]-acrylate which is in the form of a mixture of the two isomers and is processed without further purification; thin layer chromatogram (silica gel): Rf = 0.24 and 0.30 (benzene/ethyl acetate, 1:1); infrared absorption spectrum (in methylene chloride): characteristic bands at 2.90–3.10µ (with a strong maximum at 2.97µ), 3.40–3.55µ, 5.62µ, 5.77µ, 5.89µ, 6.30µ, 6.63µ, 6.72µ and 7.33µ.

g. A mixture of 0.3215 g of the crude ethyl trans-3-[2-oxo-3β-phenoxyacetylamino-1-(tert.-butoxycarbonyl-hydroxymethyl)-4β-acetidinylthio)-acrylate and 0.8 g of the polystyrene-"Hunig base" in 7 ml of dioxane is stirred at room temperature. After 30 minutes, 0.216 g of thionyl chloride in 2 ml of dioxane is added dropwise; the mixture is stirred for a further 3 hours at room temperature and filtered and the filter residue is washed with dioxane. The filtrate is evaporated under reduced pressure. The residue, which contains an amorphous mixture of the isomers of ethyl trans-3-[1-chloro-tert.-butoxycarbonyl-methyl)-2-oxo-3β-phenoxyacetylamino-4β-azetidinylthio]-acrylate, is further processed without further purification; thin layer chromatogram (silica gel): Rf = 0.51 and 0.55 (ethyl acetate/benzene, 1:1); infrared absorption spectrum (in methylene chloride): characteristic bands at 2.97µ, 3.32–3.52µ, 5.60µ, 5.76µ, 5.89µ, 6.30µ, 6.63µ, 6.71µ and 7.33µ.

h. 0.28 g of triphenylphosphine and 0.8 g of polystyrene-"Hunig base" are added to a mixture of 0.32 of crude ethyl trans-3-[1-(chloro-tert.-butoxycarbonyl-methyl)-2-oxo-3β-phenoxyacetylamino-4β-azetidinylthio]-acrylate in 14 ml of dioxane and the mixture is stirred at 50° and under a nitrogen atmosphere. After 20 hours at this temperature and 1 hour at 70°, the mixture is filtered and the filter residue is washed with dioxane. The filtrate is evaporated under reduced pressure and the residue is chromatographed on 30 g of silica gel. Impurities are removed using a 4:1 mixture of benzene and ethyl acetate and amorphous ethyl trans-3-[2-oxo-3β-phenoxyacetylamino-1-(triphenylphosphoranylidene-tert.-butoxycarbonyl-methyl)-4β-azetidinylthio]-acrylate is obtained in several fractions using a 1:1 mixture of benzene and ethyl acetate and it is possible to purify impure fractions by means of preparative plate chromatography (solvent: benzene/ethyl acetate, 1:1); thin layer chromatography (silica gel): Rf = 0.25 (benzene/ethyl acetate, 1:1); infrared absorption spectrum (in methylene chloride): characteristic bands at 2.97µ, 3.35–3.55µ, 5.66µ, 5.90µ, 6.14µ, 6.30µ, 6.62µ, 6.73µ, 6.99µ, 7.28µ and 7.36µ.

EXAMPLE 3

A solution of 0.587 g of methyl 2-(4β-acetylthio-2-oxo-3β-phenoxyacetylamino-1-azetidinyl)-2-triphenyl-phosphoranylidene-acetate in 250 ml of toluene is heated at 80° under an argon atmosphere for 46 hours. The solvent is evaporated; the residue is chromatographed on 140 g of silica gel (acid-treated), a 4:1 mixture of benzene and ethyl acetate being used. Amorphous methyl 2-methyl-6β-phenoxyacetylamino-2-penem-3-carboxylate is obtained in several fractions; ultraviolet absorption spectrum (in ethanol): $\lambda_{max}$ at 306 mµ, 275 mµ, 268 mµ and 262 mµ; infrared absorption spectrum (in methylene chloride): characteristic bands at 2.97µ, 3.32µ, 3.43µ, 5.56µ, 5.85–5.90µ, 6.27µ, 6.60µ, 6.70µ, 6.97µ and 7.08µ.

The starting material can be prepared as follows:

a. A solution of 0.588 g of 4β-acetylthio-3β-phenoxyacetylamino-azetidin-2-one and 0.636 g of the hydrate of methyl glyoxylate (boiling point 55°–62°/35 mm Hg; prepared by treating dimethyl tartrate in benzene with lead tertaacetate) in 20 ml of toluene and 5 ml of dimethylformamide is stirred in the presence of molecular sieves (see Example 1) for 90 minutes at room temperature and the mixture is then filtered. The material on the filter is rinsed with toluene and the filtrate is evaporated under reduced pressure. This gives amorphous methyl 2-(4β-acetylthio-2-oxo-3β-phenoxyacetylamino-1-azetidinyl)-2-hydroxy-acetate; infrared absorption spectrum (in methylene chloride: characteristic bands at 2.83µ, 2.95µ, 3.28–3.40µ, 5.60µ, 5.71µ, 5.88µ, 5.96µ (shoulder), 6.24µ, 6.27µ (shoulder), 6.58µ and 6.70µ. The product is further processed without purification.

b. A suspension of 2 g of "polystyrene-Hunig base" (see Example 1) in 20 ml of absolute dioxane is stirred under a nitrogen atmosphere for 30 minutes and then treated with 1.08 g of crude methyl 2-(4β-acetylthio-2-oxo-3β-phenoxyacetylamino-1-azetidinyl)-2-hydroxy-acetate, followed by about 0.6 g of thionyl chloride in 10 ml of dioxane. The mixture is stirred for 3 hours at room temperature and then filtered and the filter residue is washed with dioxane. The filtrate is evaporated under reduced pressure. This gives methyl 2-(4β-acetylthio-2-oxo-3β-phenoxyacetylamino-1-azetidinyl)-2-chloro-acetate; thin layer chromatogram (silica gel): Rf~ 0.4 and 0.44 (system: benzene/ethyl acetate, 1:1); infrared absorption spectrum (in methylene chloride): characteristic bands at 2.95µ, 3.30µ, 3.42µ, 5.59µ, 5.70µ, 5.89µ, 6.15µ, 6.19µ (shoulder), 6.61µ and 6.70µ. The product is further processed without purification.

c. A solution of 1.03 g of crude methyl 2-(4β-acetylthio-2-oxo-3β-phenoxyacetylamino-1-azetidinyl)-2-chloro-acetate and 0.786 g of triphenylphosphine in 30 ml of absolute dioxane is stirred in the presence of 2.0 of "polystyrene-Hunig base" at 50° for 18 hours under a nitrogen atmosphere and the mixture is then filtered. The filter residue is washed with dioxane and the filtrate is evaporated. The residue is chromatographed on 30 g of silica gel and at the start a 4:1 mixture of benzene and ethyl acetate is used as the mobile phase and 50 ml fractions are taken off. The excess triphenylphosphine and the impurities are washed out in the first fractions. Amorphous methyl 2-(4β-acetylthio-2-oxo-3β-phenoxyacetylamino-1-azetidinyl)-2-triphenylphosphoranylideneacetate is washed out with a 1:1 mixture of benzene and ethyl acetate; $[\alpha]_D^{20} = -29° \pm 1°$ ($c = 0.774$ in chloroform); infrared absorption spectrum (in methylene chloride): characteristic bands at 2.96μ, 3.31μ, 3.40μ, 5.67μ, 5.90μ, 6.09μ (shoulder), 6.19μ, 6.25μ (shoulder), 6.26μ (shoulder), 6.60μ, 6.71μ and 6.97μ.

Methyl 2-(4β-acetylthio-2-oxo-3β-phenoxyacetylamino-1-azetidinyl)-2-hydroxy-acetate can also be prepared as follows:

d. A solution of 18.5 g of the 1-oxide of penicillin V in tetrahydrofurane is cooled to 0° and 160 ml of a solution of diazomethane in diethyl ether is added dropwise until no further starting material can be detected by thin layer chromatography (system: acetic acid/toluene/water, 5:5:1). The reaction mixture is evaporated under reduced pressure and the residue is dissolved in hot ethyl acetate. Diethyl ether is added slowly, whilst stirring, and the mixture is left to stand at 0° for 3 days until all of the precipitate has settled out. This gives the crystalline 1-oxide of the methyl ester of penicillin V, melting point 135°–137°; ultraviolet absorption spectrum (in ethanol): $\lambda_{max}$ at 260 mμ; ($\epsilon = 1,000$), 267 mμ ($\epsilon = 1,300$) and 273 mμ ($\epsilon = 1,100$); infrared absorption spectrum (in methylene chloride): characteristic bands at 5.55μ, 5.7μ, 5.9μ and 8.25μ.

e. 37.5 ml of acetic anhydride and 12.5 ml of trimethyl phosphite are added to a solution of 9.5 g of the 1-oxide of the methyl ester of penicillin V in 300 ml of benzene and the mixture is heated at a bath temperature of 100° for 23 hours. After cooling, the solvent and the excess of the reagents are removed under reduced pressure and the residue is twice taken to dryness with toluene. The residue is chromatographed on 300 g of silica gel and for this a 7:1 mixture of toluene and ethyl acetate (10 fractions each of 300 ml) and a 4:1 mixture of toluene and ethyl acetate (10 fractions each of 300 ml) are used. First impurities and then methyl 2-(4β-acetylthio-2-oxo-3β-phenoxyacetylamino-1-azetidinyl)-2-(1-propen-2-yl)-acetate, as a colourless and solid but non-crystalline product, are washed out; thin layer chromatogram (silica gel): Rf 0.4 (system: toluene/ethyl acetate, 1:1); infrared absorption spectrum (in methylene chloride): characteristic bands at 5.55μ, 5.65μ, 5.85μ and 6.65μ.

0.8 ml of triethylamine is added to a solution of 4.04 g of methyl 2-(4β-acetylthio-2-oxo-4β-phenoxyacetylamino-1-azetidinyl)-2-(1-propen-2-yl)-acetate in 80 ml of dry methylene chloride at room temperature. The reaction mixture is stirred for 70 minutes and then washed with dilute hydrochloric acid and a dilute aqueous solution of sodium chloride. The organic phase is dried over sodium sulphate and evaporated under reduced pressure. This gives methyl 2-(4β-acetylthio-2-oxo-3β-phenoxyacetylamino-1-azetidinyl)-2-(2-propylidene)-acetate as a colourless amorphous product; infrared absorption spectrum (in methylene chloride): characteristic bands at 5.65μ, 5.75μ (shoulder), 5.85μ and 8.15μ.

g. A solution of 4 g of methyl 2-(4β-acetylthio-2-oxo-3β-phenoxyacetylamino-1-azetidinyl)-2-(2-propylidene)-acetate in 100 ml of methanol is cooled to −20° and an ozone/oxygen mixture is passed through the solution for 100 minutes (a total of 3-equivalents of ozone). The white crystalline precipitate is dissolved in 300 ml of methylene chloride and the solution is washed with 100 ml of a 10% strength aqueous solution of sodium bisulphite. The organic phase is dried over sodium sulphate and evaporated under reduced pressure. The residue is crystallised at 0° by adding methanol. This gives methyl 2-(4β-acetylthio-2-oxo-3β-phenoxyacetylamino-1-azetidinyl)-2-oxo-acetate, melting point 142°–145°; infrared absorption spectrum (in methylene chloride): characteristic bands at 5.45μ, 5.70μ and 5.85μ.

h. A solution of 0.380 g of methyl 2-(4β-acetylthio-2-oxo-3β-phenoxyacetylamino-1-azetidinyl)-2-oxo-acetate in 10 ml of dry tetrahydrofurane (distilled over lithium aluminium hydride) is cooled in an ice bath and treated with 1.5 ml of a 1 molar solution of diborane in tetrahydrofurane. The mixture is stirred for 60 minutes, whilst cooling to 0°, and then diluted with ice-cooled methylene chloride and the organic phase is separated off and washed with a 25% strength aqueous solution of ammonium chloride and with water. The organic phase is dried over sodium sulphate and evaporated under reduced pressure. This gives methyl 2-(4β-acetylthio-2-oxo-3β-phenoxyacetylamino-1-azetidinyl)-2-hydroxy-acetate.

EXAMPLE 4

A mixture of 0.022 g of methyl 2-methyl-6β-phenoxyacetylamino-2-penem-3-carboxylate and methylene chloride is treated at room temperature with 0.013 g of 3-chloro-perbenzoic acid (85% strength). After 90 minutes the reaction product is partitioned between methylene chloride and an 8% strength aqueous solution of sodium bicarbonate; the organic phase is separated off, dried and evaporated. This gives the amorphous 1-oxide of methyl 2-methyl-6β-phenoxyacetylamino-2-penem-3-carboxylate of the formula

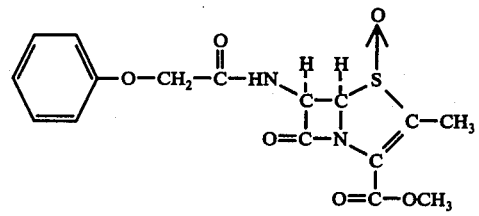

Infrared absorption spectrum (in methylene chloride): characteristic bands at 2.97μ, 3.42μ, 5.52μ, 5.78μ, 5.92μ, 6.25μ, 6.29μ (shoulder), 6.60μ, 6.70μ and 6.96μ.

EXAMPLE 5

A solution of 0.022 g of tert.-butyl 2-[4β-(4-nitrobenzoyl)-thio-2-oxo-3β-phenoxyacetylamino-1-azetidinyl]-2-triphenylphosphoranylidene-acetate in 3 ml of dry toluene is kept in a heating bath at 55° for 17 hours and during this time a stream of argon is passed through the solution. The solution is then taken to dryness under reduced pressure and the residue, in 10 ml of a 4:1 mixture of toluene and ethyl acetate, is filtered through 0.6 g of silica gel and the filtrate is then evaporated. Amorphous tert.-butyl 2-(4-nitro-phenyl)-6β-phenoxyacetylamino-2-penem-3carboxylate is thus obtained as the residue after the filtrate has been evaporated; infrared absorption spectrum (in methylene chloride): characteristic bands at 5.55μ, 5.9μ, 6.25μ, 6.6μ, 7.45μ and 8.7μ.

The starting material can be obtained as follows:

a. 18.8 g of 2-mercapto-benzthiazole are added to a solution of 38.5 g of the 1-oxide of the methyl ester of penicillin V in 1,000 ml of toluene and the reaction mixture is warmed at a bath temperature of 130° for 8 hours. After cooling, the solvent is removed under reduced pressure, the residue is dissolved in 600 ml of ethyl acetate at 60° and the solution is filtered through a warm glass filter. The filtrate is evaporated to a volume of 400 ml and kept at −20° for 2 days. Methyl 2-[4β-(2-benzthiazolyl-dithio)-2-oxo-3β-phenoxyacetylamino-1-azetidinyl]-2-(1-propen-2-yl)-acetate is obtained as a crystalline product; melting point 135°-137° after recrystallisation from ethyl acetate; ultraviolet absorption spectrum (in ethanol): $\lambda_{max}$ = 243 mμ (ε = 9,300), 268 mμ (ε = 13,700) and 275 mμ (ε = 13,000); infrared absorption spectrum (in methylene chloride): characteristic bands at 5.6μ, 5.75μ, 5.9μ, 8.15μ and 9.95μ.

b. 4 ml of triethylamine are added to a solution of 26.5 g of methyl 2-[4β-(2-benzthiazolyl-dithio)-2-oxo-3β-phenoxy-acetylamino-1-azetidinyl]-2-(1-propen-2-yl)-acetate in 400 ml of methylene chloride at room temperature and the mixture is stirred for 40 minutes at room temperature and then washed with 200 ml of 1 N hydrochloric acid and with a dilute aqueous solution of sodium chloride. The organic phase is dried over sodium sulphate and then evaporated under reduced pressure. The non-crystalline residue is chromatographed on 500 g of silica gel using a 3:1 mixture of toluene and ethyl acetate as the mobile phase; 14 fractions of 500 ml each are withdrawn. In this way methyl 2-[4β-(2-benzthiazolyl-dithio)-2-oxo-3β-phenoxyacetylamino-1-azetidinyl]-2-(2-propylidene)-acetate is obtained as a pale yellow non-crystalline product which can be crystallised from ethyl acetate, melting point 179°-182°; infrared absorption spectrum (in methylene chloride): characteristic bands at 5.6μ, 5.75μ, 5.9μ, 8.15μ and 9.9μ.

c. A solution of 0.106 g of methyl 2-[4β-(2-benzthiazolyl-dithio)-2-oxo-3β-phenoxyacetylamino-1-azetidinyl]-2-(2-propylidene)-acetate in 5 ml of dry dimethylformamide is cooled to −20° and a solution of 0.01 g of sodium borohydride in 1 ml of dimethylformamide is added; a solution is produced by stirring the mixture for 10 minutes at room temperature. The reaction mixture is stirred for 30 minutes at −20° and 0.207 g of 4-nitro-benzoyl chloride in 0.5 ml of dimethylformamide is then added. The mixture is washed with a further 0.5 ml of dimethylformamide and then stirred for 40 minutes at room temperature. It is diluted with 70 ml of benzene, filtered and washed with three times 10 ml of water. The organic phase is dried over sodium sulphate and evaporated under reduced pressure. The residue is taken up in 20 ml of a toluene/ethyl acetate mixture and kept at 0° for 1 hour. The insoluble material is filtered off and the filtrate is chromatographed on 5 g of silica gel, fractions being washed out with a 7:1 mixture and a 3:1 mixture of toluene and ethyl acetate. Methyl 2-[4β-(4-nitro-benzoyl)-thio-2-oxo-3β-phenoxyacetylamino-1-azetidinyl]-2-(2-propylidene)-acetate is obtained as a colourless foam which crystallises from methanol, melting point 132°-134°; infrared absorption spectrum (in methylene chloride): characteristic bands at 5.65μ, 5.8μ, 5.95μ, 6.55μ, 7.4μ and 11.8μ.

d. A solution of 1.8 g of methyl 2-[4β-(4-nitro-benzoyl)-thio-2-oxo-3β-phenoxyacetylamino-1-azetidinyl]-2-(2-propylidene)-acetate in 20 ml of ethyl acetate is filtered through a glass filter and the filtrate is treated, at −20°, with ozone (0.33 mmol/minute) for 45 minutes. It is then diluted with 100 ml of ethyl acetate and washed with 40 ml of a 10% strength aqueous solution of sodium bisulphite and with twice 25 ml of a dilute aqueous solution of sodium chloride and the organic phase is dried with sodium sulphate. The solvent is evaporated under reduced pressure and the residue is recrystallised from cold methanol. This gives methyl 2-[4β-(4-nitrobenzoyl)-thio-2-oxo-3β-phenoxyacetylamino-1-azetidinyl]-2-oxo-acetate, melting point 130°-133°; infrared absorption spectrum (in methylene chloride): characteristic bands at 5.5μ, 5.7μ, 5.9μ, 6.55μ, 7.45μ and 11.8μ.

e. A solution of 0.48 g of methyl 2-[4β-(4-nitro-benzoyl)-thio-2-oxo-3β-phenoxyacetylamino-1-azetidinyl]-2-oxo-acetate in 0.4 ml ethyl acetate is diluted with 20 ml of a 98:2 mixture of methanol and water and left to stand at room temperature for 16 hours. It is evaporated under reduced pressure and the residue is again taken to dryness with 5 ml of methanol and then crystallised from an ethyl acetate/benzene mixture. This gives 4β-(4-nitro-benzoyl)-thio-3β-phenoxyacetylaminoazetidin-2-one, melting point 152°-155°; infrared absorption spectrum (potassium bromide): characteristic bands at 5.65μ, 6.0μ, 6.55μ, 7.4μ and 11.8μ. A further amount of the desired product can be isolated from the mother liquor by means of chromatography on silica gel and using 4:1 and 3:1 mixtures of toluene and ethyl acetate as the mobile phases.

f. 2 g of a molecular sieve are added to a solution of 0.08 g of 4β-(4-nitro-benzoyl)-thio-3β-phenoxyacetylaminoacetidin-2-one and 0.2 g of tert.-butyl glyoxylate in 1 ml of dry dimethylformamide and 2 ml of toluene and the mixture is stirred for 3 hours at room temperature. After filtering and rinsing the material on the filter with dry tetrahydrofurane and toluene, the filtrate is evaporated under a high vacuum and the residue is taken to dryness several times with toluene. This gives tert.-butyl 2-hydroxy-2-[4β-(4-nitro-benzoyl)-thio-2-oxo-3β-phenoxyacetylamino-1-azetidinyl]-acetate as an amorphous foam; infrared absorption spectrum (in methylene chloride): characteristic bands at 5.6μ, 5.7μ, 5.9μ, 6.5μ, 7.4μ and 11.75μ.

g. The tert.-butyl 2-hydroxy-2-[4β-(4-nitro-benzoyl)-thio-2-oxo-3β-phenoxyacetylamino-1-azetidinyl]-acetate obtainable according to the above process is dissolved in 2 ml of dry tetrahydrofurane and the solution is stirred at 0° and 16 μl of thionyl chloride and 32 μl of triethylamine are then added. The reaction mixture is stirred at 0° for 30 minutes, then diluted with toluene and washed with dilute nitric acid and water. The organic phase is dried over sodium sulphate and evaporated under reduced pressure. This gives a mixture of the two isomers of tert.-butyl 2-chloro-2-[4β-(4-nitro-benzoyl)-thio-2-oxo-3β-phenoxyacetylamino-1-azetidinyl]-acetate which can purified by chromatography on 3.5 g of silica gel using 30 ml of a 4:1 mixture of toluene and ethyl acetate and which is obtained as an amorphous product.

A solution of 0.027 g of the mixture of the two isomers of tert.-butyl 2-chloro-2-[4β-(4-nitro-benzoyl)-thio-2-oxo-3β-phenoxyacetylamino-1-azetidinyl]-acetate and 0.026 g of triphenylphosphine in 0.5 ml of dry tetrahydrofurane is kept at room temperature under an argon atmosphere for 4 days. 20 ml of ethyl acetate are added, the mixture is washed with 20 ml of a dilute aqueous solution of sodium chloride and the organic phase is dried over sodium sulphate and evaporated under reduced pressure. An oily product is obtained in this way and this is chromatographed on 1 g of silica gel using 5 l ml fractions of a 5:1 mixture of ethyl acetate and toluene and 7 l ml fractions of a 2:1 mixture of ethyl acetate and toluene. This gives tert.-butyl 2-[4β-(4-nitro-benzoyl)-thio-2-oxo-3β-phenoxyacetylamino-1-azetidinyl]-2-triphenylphosphoranylideneacetate as a pure amorphous product; infrared absorption spectrum (in methylene chloride): characteristic bands at 5.65μ, 5.9μ, 5.95μ, 6.2μ, 6.55μ, 7.45μ and 11.8μ.

EXAMPLE 6:

0.05 g of a 5% strength palladium-on-charcoal catalyst is added to a solution of 0.02 g of tert.-butyl 2-(4-nitrophenyl)-6β-phenoxyacetylamino-2-penem-3-carboxylate in 2 ml of dry methanol and hydrogenation is carried out for 30 minutes at 0°. The reaction mixture is filtered and evaporated under reduced pressure. This gives tert.-butyl 2-(4-aminophenyl)-6β-phenoxyacetylamino-2-penem-3-carboxylate as a pale yellow amorphous product; infrared absorption spectrum (in methylene chloride): characteristic bands at 5.55μ, 5.9μ, 6.2μ, 6.6μ, 6.7μ and 8.65μ.

EXAMPLE 7:

A solution of 0.209 g of 4-nitrobenzyl 2-(4β-acetylthio-2-oxo-3β-phenoxyacetylamino-1-azetidinyl)-2-triphenyl-phosphoranylidene-acetate in 210 ml of toluene is kept at 80° for 4½ days, during which time a stream of argon is passed through the reaction mixture. This mixture is then evaporated under reduced pressure and the residue is chromatographed on 30 g of silica gel, a 4:1 mixture of benzene and ethyl acetate being used as the mobile phase and 50 ml fractions being withdrawn. After two fractions, which are discarded, amorphous 4-nitrobenzyl 2-methyl-6β-phenoxyacetylamino-2-penem-3-carboxylate is eluted with fractions 3 and 4; infrared absorption spectrum (in methylene chloride): characteristic bands at 2.97μ, 3.31μ, 3.45μ, 5.54μ, 5.86–5.91μ, 6.30μ, 6.58μ, 6.72μ, 6.95μ, 7.08μ (shoulder), 7.43μ and 7.66μ.

The starting material can be prepared as follows:

a. 8.64 g of 4-nitrobenzyl bromide in 20 ml of dimethylformamide are added dropwise to a solution of 3 g of L-(+)-tartaric acid and 5.6 ml of triethylamine in 20 ml of dimethylformamide, the mixture being stirred at room temperature and a precipitate forming shortly after the addition has ended. After 19 hours the mixture is diluted with 300 ml of benzene and 100 ml of water, whereupon the precipitate first dissolves and a new precipitate then settles out. The latter is filtered off and washed with benzene. This gives di-4-nitrobenzyl L-(+)-tartrate; melting point 163°–165°; infrared absorption spectrum (in potassium bromide): characteristic bands at 2.91μ, 3.29μ, 3.45–3.55μ, 5.86μ, 6.21μ, 6.51μ, 6.70μ, 6.96μ, 7.27μ, 7.40μ (shoulder), 7.45μ, 7.80μ, 7.85μ (shoulder), 8.0–8.07μ, 8.80μ, 9.25μ and 10.07μ.

b. A total of 3.16 g of lead tetraacetate are added, in small portions, in the course of 25 minutes to a solution of 3 g of di-4-nitrobenzyl L-(+)-tartrate in 60 ml of dioxane and 60 ml of benzene, whilst stirring and at room temperature. After stirring for a further 90 minutes at room temperature, the precipitate is filtered off and washed with benzene. The filtrate is evaporated under reduced pressure and the residue is partitioned between methylene chloride and an aqueous solution of sodium bicarbonate; the insoluble material is filtered off the discarded. The organic phase is dried and evaporated. This gives the hydrate of 4-nitrobenzyl glyoxylate; infrared absorption spectrum (in methylene chloride): characteristic bands at 2.90μ, 3.31μ, 3.44μ, 3.54μ, 5.71μ, 5.76μ (shoulder), 6.23μ, 6.55μ, 7.44μ, 7.61μ, 7.80–8.45μ (broad) and 8.80–9.30μ (broad).

c. In another batch using 2.8 g of di-4-nitrobenzyl L-(+)-tartrate no precipitate forms after the residue has been partitioned between methylene chloride and an aqueous solution of sodium bicarbonate; the organic phase is separated off and evaporated; in this way a product is obtained which, according to the NMR spectrum, in the main consists of the ethyl hemi-acetal of 4-nitrobenzyl glyoxylate. The ethanol required to form this product very probably originates from the ethanol-stabilised methylene chloride.

d. A mixture of 0.588 g of 4β-acetylthio-3β-phenoxyacetylamino-azetidin-2-one and 0.765 g of the ethyl hemi-acetal of 4-nitrobenzyl glyoxylate in 20 ml of toluene and 5 ml of dimethylformamide is stirred at room temperature in the presence of molecular sieves for 2 hours and the mixture is then filtered. The material on the filter is rinsed with toluene and the filtrate is evaporated under reduced pressure, finally under a high vacuum. The residue is amorphous 4-nitro benzyl 2-(4β-acetylthio-2-oxo-3β-phenoxyacetylamino-1-azetidinyl)-2-hydroxy-acetate; thin layer chromatography (silica gel): Rf = 0.25 (system: benzene/ethyl acetate, 1:1); infrared absorption spectrum (in methylene chloride): characteristic bands at 2.85μ (shoulder), 2.97μ, 3.33μ, 3.44μ (shoulder), 5.61μ, 5.72μ, 5.90μ, 6.26μ, 6.30μ (shoulder), 6.55μ, 6.70μ, 6.97μ, 7.09μ (shoulder), 7.44μ, 7.80μ (shoulder) and 8.0–8.34μ (broad); and is processed without purification.

e. A mixture of 1.39 g of 4-nitrobenzyl 2-(4β-acetylthio-2-oxo-3β-phenoxyacetylamino-1-azetidinyl)-2-hydroxy-acetate and 20 ml of dioxane is stirred at room temperature in the presence of 1.8 g of "polystyrene-Hunig base" for 30 minutes and then treated with a solution of 0.720 g of thionyl chloride in 12 ml of dioxane. The mixture is stirred for a further 5 ¼ hours and filtered; the filter residue is washed with dioxane and the filtrate is evaporated under reduced pressure. The residue gives amorphous 4-nitrobenzyl 2-(4β-acetylthio-2-oxo-3β-phenoxyacetylamino-1-azetidinyl)-2-chloro-acetate; infrared absorption spectrum (in methylene chloride): characteristic bands at 2.97μ, 3.32μ, 3.41μ, 5.60μ, 5.72μ, 5.90μ, 6.30μ, 6.35μ (shoulder), 6.55μ, 6.70μ, 6.95–7.10μ (broad) and 7.42μ; which is further processed without purification.

f. A mixture of 1.4 g of 4-nitrobenzyl 2-(4β-acetylthio-2-oxo-3β-phenoxyacetylamino-1-azetidinyl)-2-chloro-acetate, 0.785 g of triphenylphosphine and 1.8 g of "polystyrene-Hunig base" in 20 ml of dioxane is warmed at 50° under a nitrogen atmosphere for 17 hours and then filtered. The material on the filter is rinsed with dioxane, the filtrate is evaporated under reduced pressure and the residue is chromatographed on 30 g of silica gel. A fraction is first washed out with a mixture of benzene and ethyl acetate and 4-nitrobenzyl 2-(4β-acetylthio-2-oxo-3β-phenoxyacetylamino-1-azetidinyl)-2-triphenylphosphoranylidene-acetate is eluted with a 1:1 mixture of benzene and ethyl acetate and is obtained as an amorphous product; thin layer chromatogram (silica gel): Rf = 0.20 (system: benzene/ethyl acetate, 1:1); infrared absorption spectrum (in methylene chloride): characteristic bands at 2.98μ, 3.33μ, 3.42μ, 5.66μ, 5.90μ, 6.09μ (shoulder), 6.15μ, 6.24μ, 6.57μ, 6.71μ, 6.98μ, 7.08μ (shoulder), 7.17μ (shoulder) and 7.44μ.

EXAMPLE 8 a. A solution of 0.0415 g of 4-nitrobenzyl 2-methyl-6β-phenoxyacetylamino-2-penem-3-carboxylate in 2.5 ml of ethyl acetate is stirred at room temperature in a hydrogen atmosphere under normal pressure in the presence of 1.4 ml of a 0.2 molar aqueous solution of sodium bicarbonate and of 0.042 g of a 5% strength palladium-on-charcoal catalyst. The reaction mixture is filtered after 30 minutes; the catalyst is filtered off and washed with ethyl acetate. The organic phase of the filtrate is separated off and extracted with 1.5 ml of a dilute aqueous solution of sodium bicarbonate; the aqueous phase of the filtrate is washed with ethyl acetate. The organic phases are combined and evaporated; the residue contains no acid material and is discarded. The combined aqueous solutions are saturated with sodium chloride and extracted with methylene chloride. The organic extracts are dried over sodium sulphate and evaporated. This gives amorphous 2-methyl-6β-phenoxyacetylamino-2-penem-3-carboxylic acid of the formula

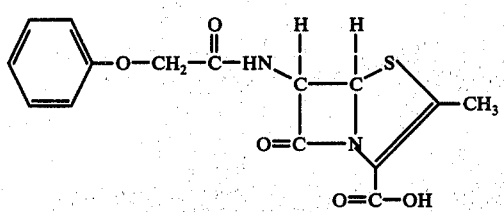

Ultraviolet absorption spectrum (in 96% strength aqueous ethanol): $\lambda_{max}$ = 300 mμ, 272 mμ, 266 mμ and 258 mμ; infrared absorption spectrum (in methylene chloride): characteristic bands at 2.97μ, 3.0–4.2μ (broad), 5.55μ, 5.91μ (broad), 6.25μ (shoulder), 6.31μ, 6.34μ (shoulder), 6.60μ and 6.70μ.

b. A solution of 51 mg of 4-nitrobenzyl 2-methyl-6β-phenoxyacetylamino-2-penem-3-carboxylate in 3 ml of ethyl acetate is stirred at room temperature in a hydrogen atmosphere under normal pressure in the presence of 0.2 molar aqueous sodium bicarbonate solution and of 100 mg of a 10% strength palladium-on-charcoal catalyst. After 30 minutes a further 50 mg of the catalyst are added, after which the mixture is stirred for a further 5 minutes. The resulting mixture is filtered and the catalyst on the filter is washed with 0.7 ml of 0.2 molar sodium bicarbonate solution and with a large amount of ethyl acetate. The two layers of the filtrate are separated. The aqueous phase is acidified by adding 5 ml of a 5% strength citric acid solution and repeatedly extracted with methylene chloride. The methylene chloride solution is dried with sodium sulphate and evaporated in vacuo. This gives amorphous 2-methyl-6β-phenoxyacetylamino-2-penem-3-carboxylic acid which has a UV spectrum identical to that of Example 8a); IR spectrum (in methylene chloride): characteristic absorption bands at 2.97; 2.80–4.20 (broad); 5.55; 5.83 (sh); 5.88 (sh); 5.92; 6.23 (sh); 6.27 (sh); 6.29; 6.59; 6.69; 6.95; and 7.06 (sh) μ.

c. The dicyclohexylammonium salt of the acid employed is obtained by adding a solution of 5.9 ml (1.1 equivalents) of dicyclohexylamine in 0.2 ml of methylene chloride to a solution of 10 mg of 2-methyl-6β-phenoxyacetylamino-2-penem-3-carboxylic acid in 1 ml of methylene chloride, evaporating the resulting solution and drying the residue under a high vacuum.

EXAMPLE 9:

A solution of 0.150 g of allyl 2-(4β-acetylthio-2-oxo-3β-phenoxyacetylamino-1-azetidinyl)-2-triphenylphosphoranylidene-acetate in 100 ml of toluene is warmed at 80° in an argon atmosphere for 2½ days and then evaporated under reduced pressure. The syrupy residue is chromatographed on 15 g of acid-washed silica gel, a 4:1 mixture of benzene and ethyl acetate being used as the mobile phase and 25 ml fractions being withdrawn. Allyl 2-methyl-6β-phenoxyacetylamino-2-penem-3-carboxylate is washed out in fractions 2 and 3 and obtained as a colourless amorphous foam; thin layer chromatogram (silica gel): Rf = 0.48 (system: ethyl acetate/benzene, 1:1); infrared absorption spectrum (in methylene chloride): characteristic bands at 2.96μ, 3.40μ, 5.55μ, 5.86μ (broad), 6.25μ, 6.59μ, 6.69μ, 7.35μ and 7.65μ.

The starting material can be prepared as follows:

a. 10.5 ml of allyl bromide are added dropwise to a solution of 9.0 g of L-(+)-tartaric acid and 16.8 ml of triethylamine in 50 ml of dimethylformamide and during the addition the reaction mixture is stirred and cooled from time to time with cold water. After the addition, which takes 15 minutes, the reaction mixture is stirred for 2½ hours at room temperature and then partitioned between benzene and water. The organic phase is dried over sodium sulphate and evaporated. The oily residue is distilled and diallyl L-(+)-tartrate is distilled at a bath temperature of 140°–150° and under a pressure of 0.3 mm Hg; infrared absorption spectrum (methylene chloride): characteristic bands at 2.86μ, 3.43μ, 5.75μ, 7.25μ, 7.38μ, 7.75μ (broad), 8.13μ (broad), 8.35μ, 8.93μ, 9.20μ, 10.17μ (broad) and 10.62μ (broad).

b. A solution of 5.05 g of diallyl L-(+)-tartrate in 10 ml of acetic acid and 25 ml of water is treated dropwise with 6.2 g of sodium periodate in 40 ml of water; the addition takes 30 minutes and during this time the mixture is stirred and cooled in a waterbath. After a further 30 minutes at room temperature, the reaction mixture is partitioned between ethyl acetate and water and the organic phase is washed with water and the aqueous phase is washed with ethyl acetate. The combined organic solutions are evaporated; the residue is again dissolved in ethyl acetate and the solution is filtered through a short column containing neutral aluminium oxide and the filtrate is then evaporated. The residue is distilled in the presence of a few crystals of hydroquinone; the dihydrate of allyl glyoxylate is distilled at a bath temperature of 110°–130° and under a pressure of 30–40 mm Hg; infrared absorption spectrum (in methylene chloride): characteristic bands at 2.86μ (broad), 3.43μ, 3.55μ, 5.73μ, 6.25μ, 7.72–8.00μ (broad), 8.24μ (broad), 9.13μ (broad), 9.67μ (broad), 10.15μ (broad) and 10.63μ (broad).

c. 0.400 g of the hydrate of allyl glyoxylate is added to a solution of 0.294 g of 4β-acetylthio-3β-phenoxyacetylamino-azetidin-2-one in 2.5 ml of dimethylformamide and 10 ml of toluene and the mixture is stirred at room temperature in the presence of molecular sieves and under a nitrogen atmosphere. After 2–2½ hours it is filtered; the filter residue is washed with toluene. The combined filtrates are evaporated under reduced pressure, finally under a high vaccum. In this way syrupy allyl 2-(4β-acetylthio-2-oxo-3-phenoxyacetylamino-1-azetidinyl)-2-hydroxy-acetate is obtained; thin layer chromatogram (silica gel): Rf = 0.26 (system: ethyl acetate/benzene, 1:1); infrared absorption spectrum (in methylene chloride): characteristic bands at 2.88μ, 2.97μ, 3.45μ, 5.60μ, 5.73μ, 5.90μ, 6.25μ, 6.30μ (shoulder), 6.60μ, 6.70μ, 6.98μ, 7.40μ (broad), 7.75–8.00μ (broad), 8.10–8.30μ (broad) and 8.55μ.

d. A suspension of 1 g "polystyrene-Hunig base" in 5 ml of dioxane is stirred at room temperature for 2 hours and a solution of 0.60 g of allyl 2-(4β-acetylthio-2-oxo-3-phenoxyacetylamino-1-azetidinyl)-2-hydroxy-acetate in 5 ml of dioxane is added and this is followed by 0.22 ml of thionyl chloride. The mixture is stirred under a nitrogen atmosphere for 3 hours and then filtered and the filter residue is washed with dioxane. The combined filtrates are evaporated under reduced pressure and give syrupy allyl 2-(4β-acetylthio-2-oxo-3β-phenoxyacetylamino-1-azetidinyl)-2-chloro-acetate; thin layer chromatogram (silica gel): Rf = 0.53 (system: ethyl acetate/benzene, 1:1); infrared absorption spectrum (in methylene chloride): characteristic bands at 2.97μ, 3.45μ, 5.58μ, 5.70μ, 5.90μ, 6.25μ, 6.30μ (shoulder), 6.60μ, 6.70μ, 6.96μ, 7.35μ (shoulder), 7.40μ, 7.60μ, 7.80–8.00μ (broad) and 8.10–8.30μ (broad).

e. A mixture of 0.57 g of allyl 2-(4β-acetylthio-2-oxo-3β-phenoxyacetylamino-1-azetidinyl)-2-chloro-acetate and 0.4 g of triphenylphosphine in 10 ml of dioxane is stirred in the presence of 1 g of "polystyrene-Hunig base" at 50° under a nitrogen atmosphere. After 17 hours it is filtered; the filter residue is washed with dioxane and the combined filtrates are evaporated. The syrupy residue is chromatographed on 20 g of silica gel; a 4:1 mixture of benzene and ethyl acetate is used as the mobile phase and 25 ml fractions are withdrawn. Impurities are washed out in the first eight fractions, whilst allyl 2-(4β-acetylthio-2-oxo-3β-phenoxyacetylamino-1-azetidinyl)-2-triphenylphosphoranylidene-acetate is eluted with fractions 9 to 20 in the form of a colourless foam; thin layer chromatogram (silica gel): Rf = 0.27 (system: benzene/ethyl acetate, 1:1); infrared absorption spectrum (in methylene chloride): characteristic bands at 2.97μ, 3.30–3.45μ, 5.66μ, 5.90μ, 6.08μ (shoulder), 6.15μ, 6.23μ (shoulder), 6.58μ, 6.69μ, 6.95μ, 7.16μ, 7.40μ, 7.75–8.00μ (broad), 8.10μ, 8.26μ, 8.50μ, 8.85μ, 9.05μ, 9.25μ and 9.40μ.

EXAMPLE 10

A solution of 0.081 g of tert.-butyl 2-(4β-isobutyrylthio-2-oxo-3β-phenoxyacetylamino-1-azetidinyl)-2-triphenylphosphoranylidene-acetate in 40 ml of toluene is heated under an argon atmosphere for 5½ hours at 70° and then for 6 days at 80° and for 2 days at 100°. The solvent is evaporated under reduced pressure and the residue is subjected to preparative chromatography (silica gel). This gives, in addition to a relatively large amount of starting material and a by-product, tert.-butyl 2-isopropyl-6β-phenoxyacetylamino-2-penem-3-carboxylate of the formula

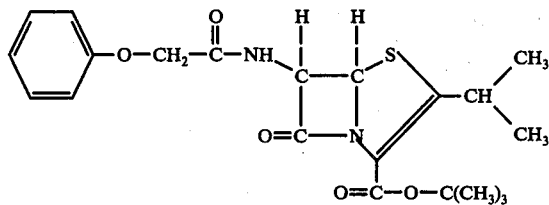

in the form of a colourless syrup; Rf = 0.57 (system: benzene/ethyl acetate, 1:1); infrared absorption spectrum (in methylene chloride): characteristic bands at 2.99μ, 3.40–3.50μ, 5.59μ, 5.91μ (broad), 6.26μ, 6.30μ (shoulder), 6.35μ (shoulder), 6.60μ, 6.70μ, 7.34μ, 8.10–8.20μ (broad), 8.30μ (shoulder) and 8.70μ.

The starting material can be obtained as follows:

a. A mixture of 3.8 g of the 1-oxide of the methyl ester of penicillin V in 120 ml of benzene, 20 ml of isobutyric anhydride and 5 ml of trimethyl phosphite is heated under reflux for 12 hours and then evaporated under reduced pressure. The syrupy residue is chromatographed on 120 g of silica gel (column). The column is pre-washed with a 7:1 mixture of benzene and ethyl acetate and tert.-butyl 2-(4β-isobutyrylthio-2-oxo-3β-phenoxyacetylamino-1-azetidinyl)-2-(1-propen-2-yl)-acetate is eluted with a 4:1 mixture of benzene and ethyl acetate; thin layer chromatogram (silica gel): Rf = 0.43 (system: benzene/ethyl acetate, 1:1); infrared absorption spectrum (in methylene chloride): characteristic bands at 2.97μ, 3.32μ, 3.41μ, 5.63μ, 5.74μ, 5.91μ, 6.24μ, 6.28μ, 6.60μ, 6.71μ, 6.97μ, 7.27μ, 7.35μ (shoulder), 7.53μ, 8.10μ (broad), 8.28μ (broad) and 8.50–8.60μ.

b. A solution of 0.100 g of tert.-butyl 2-(4β-isobutyrylthio-2-oxo-3β-phenoxyacetylamino-1-azetidinyl)-2-(1-propen-2-yl)-acetate in 2 ml of methylene chloride and 0.03 ml of triethylamine is left to stand at room temperature for 90 minutes under a nitrogen atmosphere and then diluted with additional methylene chloride. It is washed with 4 ml of 1 N hydrochloric acid and 4 ml of a 10% strength aqueous solution of sodium chloride; the organic solution is evaporated under reduced pressure and the residue is purified with the aid of preparative layer chromatography. This gives tert.-butyl 2-(4β-isobutyrylthio-2-oxo-3-phenoxyacetylamino-1-azetidinyl)-2-(2-propylidene)-acetate as a colourless foam, Rf = 0.38 (system: benzene/ethyl acetate, 1:1); infrared absorption spectrum (in methylene chloride): characteristic bands at 2.97μ, 3.32μ, 3.41μ, 5.64μ, 5.81μ (shoulder), 5.91μ, 6.15μ, 6.25μ, 6.29μ (shoulder), 6.60μ, 6.71μ, 6.97μ, 7.24μ, 7.34μ, 8.16μ (broad) and 8.12μ.

c. A solution of 1.41 g of tert.-butyl 2-(4β-isobutyrylthio-2-oxo-3-phenoxyacetylamino-1-azetidinyl)-2-(2-propylidene)-acetate in 32 ml of absolute methanol is cooled to −20° and treated, at this temperature, with a mixture of ozone and oxygen (0.33 mmol of ozone per minute) for 32 minutes. After a further 2 hours at −20°, the crystalline material is filtered off and washed with a mixture of methanol and diethyl ether. This gives tert.-butyl 2-(4β-isobutyrylthio-2-oxo-3β-phenoxyacetylamino-1-azetidinyl)-2-oxo-acetate, melting point 112°–114° after recrystallisation from methanol; [α]$_D^{20}$ = −51° ± 1° (c = 1.015 in chloroform); infrared absorption spectrum (in methylene chloride): characteristic bands at 2.97μ, 3.30μ, 3.40μ, 5.49μ, 5.70μ, 5.86μ (broad), 6.25μ, 6.29μ (shoulder), 6.60μ, 6.70μ, 6.95μ, 7.32μ (broad), 8.20μ (broad) and 8.50μ.

d. A solution of 0.650 g of tert.-butyl 2-(4β-isobutyrylthio-2-oxo-3β-phenoxyacetylamino-1-azetidinyl)-2-oxo-acetate in 13 ml methyl acetate, 100 ml of methanol and 13 ml of water is stirred at room temperature for 2½ hours and the reaction mixture is then evaporated to a smaller volume. It is partitioned between methylene chloride and water and the organic phase is separated off, dried and evaporated under reduced pressure. The residue is chromatographed on 30 ml of silica gel, the product being eluted with a 4:1 mixture of benzene and ethyl acetate. 4β-Isobutyrylthio-3β-phenoxyacetylaminoazetidin-2-one, which is still impure, is recrystallised from a mixture of methylene chloride and diethyl ether, melting point 109°–111°; thin layer chromatography (silica gel): Rf = 0.26 (system: ethyl acetate/benzene, 1:1); infrared absorption spectrum (in methylene chloride): characteristic bands at 2.97μ, 3.32μ, 3.40μ, 5.61μ, 5.92μ, 6.25μ, 6.29μ (shoulder), 6.60μ, 6.70μ, 6.97μ, 7.08μ (shoulder) and 8.10μ (broad).

e. A mixture of 0.295 g of 4β-isobutyrylthio-3β-phenoxyacetylamino-azetidin-2-one and 0.420 g of the hydrate of tert.-butyl glyoxylate in 10 ml of toluene and 2.5 ml of dimethylformamide is stirred at room temperature in the presence of molecular sieves. After 90 minutes it is filtered, the filter residue is washed with toluene and the combined filtrates are evaporated, finally under a high vacuum. This gives syrupy tert.-butyl 2-hydroxy-2-(4β-isobutyrylthio-2-oxo-3β-phenoxyacetylamino-1-azetidinyl)-acetate; thin layer chromatogram (silica gel): Rf = 0.32 (system: benzene/ethyl acetate, 1:1); infrared absorption spectrum (in methylene chloride): characteristic bands at 2.86μ, 2.97μ, 3.40μ, 3.45μ (shoulder), 5.61μ, 5.76μ, 5.91μ, 6.25μ, 6.29μ (shoulder), 6.60μ, 6.70μ, 6.97μ, 7.31μ, 7.75μ (braod), 8.15μ and 8.86μ (broad); which is further processed without purification.

f. A solution of 0.295 g of the crude tert.-butyl 2-hydroxy-2-(4β-isobutyrylthio-2-oxo-3β-phenoxyacetylamino-1-azetidinyl)-acetate in 11 ml of dioxane is stirred for 30 minutes in the presence of 1 g of "polystyrene-Hunig base" and a solution of 0.25 ml of thionyl chloride in 2.5 of dioxane is then added. The mixture is stirred for 2¼ hours at room temperature and filtered, the material on the filtrate is washed with dioxane and the combined filtrates are evaporated, finally under reduced pressure. This gives tert.-butyl 2-chloro-2-(4β-isobutyrylthio-2-oxo-3β-phenoxyacetylamino-1-azetidinyl)-acetate; thin layer chromatogram (silica gel); Rf = 0.56 (system: ethyl acetate/benzene, 1:1); infrared absorption spectrum (in methylene chloride): characteristic bands at 2.97μ, 3.40μ, 3.50μ, 5.58μ, 5.71μ, 5.89μ, 6.25μ, 6.29μ (shoulder), 6.60μ, 6.70μ, 6.89μ, 6.95μ, 7.32μ, 7.59μ, 7.75μ (broad), 8.15μ (broad) and 8.70μ; which is further processed without purification.

g. A solution of tert.-butyl 2-chloro-2-(4β-isobutyrylthio-2-oxo-3β-phenoxyacetylamino-1-azetidinyl)-acetate, which is obtainable by the above process from 0.295 g of tert.-butyl 2-hydroxy-2-(4β-isobutyrylthio-2-oxo-3β-phenoxyacetylamino-1-azetidinyl)-acetate, in 12 ml of dioxane is stirred in the presence of 1 g of "polystyrene-Hunig base" for 30 minutes, 0.4 g of triphenylphosphine is then added and the reaction mixture is stirred under a nitrogen atmosphere for 16 hours at 50°. It is filtered and the filtrate is evaporated; the syrupy residue is chromatographed on 30 g of silica gel (column). The excess triphenylphosphine and impurities are washed out with benzene. Amorphous tert.-butyl 2-(4β-isobutyrylthio-2-oxo-3β-phenoxyacetylamino-1-azetidinyl)-2-triphenylphosphoranylidene-acetate is eluted with a 1:1 mixture of benzene and ethyl acetate; thin layer chromatogram (silica gel): Rf = 0.25 (system: benzene/ethyl acetate, 1:1); infrared absorption spectrum (in methylene chloride); characteristic bands at 2.97μ, 3.40μ, 5.65μ, 5.90μ, 6.10μ, 6.18μ, 6.25μ (shoulder), 6.59μ, 6.70μ, 6.96μ, 7.33μ, 7.75–8.12μ (braod), 8.02–8.14μ (broad) and 9.07μ.

EXAMPLE 11

A solution of 0.026 g of diphenylmethyl 2-(4β-acetylthio-2-oxo-3β-phenoxyacetylamino-1-azetidinyl)-2-triphenylphosphoranylidene-acetate in 25 ml of toluene is heated at 80° for 48 hours. The solvent is then evaporated and the residue is subjected to preparative layer chromatography (silica gel). This gives diphenylmethyl 2-methyl-6β-phenoxyacetylamino-2-penem-3-carboxylate, Rf = 0.59 (system: toluene/ethyl acetate, 1:1); infrared absorption spectrum (in methylene chloride): characteristic bands at 3.0μ, 5.58μ, 5.9μ, 6.3μ, 6.65μ, 6.73μ, 8.2μ, 8.65μ and 9.3μ.

The starting material can be prepared as follows:

a. 4.2 g of L-(+)-tartaric acid are dissolved in 100 ml of warm absolute dioxane and a solution of 10.0 g of diphenyldiazomethane in 100 ml of diethyl ether is added to the solution at room temperature and whilst stirring. The mixture is left to stand for 16 hours at room temperature, the crystalline material is then filtered off and the filtrate is concentrated to a small volume. The precipitate and the residue are dissolved in methylene chloride and the solution is washed twice with sodium bicarbonate solution and once with water and evaporated. The residue is recrystallised from a mixture of methylene chloride and diethyl ether and gives bis-diphenylmethyl L-(−)-tartrate, melting point 115°–117°; $[\alpha]_D^{20}$ = −16° ± 1° ($c$ = 0.943 in chloroform); which is obtained in the form of the hydrate.

b. 1.0 g of lead tetraacetate in 25 ml of benzene is added in the course of 15 minutes to a solution of 0.965 g of the hydrate of bis-diphenylmethyl L-(−)-tartrate in 10 ml of absolute benzene. After 6 hours at room temperature the mixture is filtered; the filtrate is washed with an aqueous solution of sodium bicarbonate and a saturated solution of sodium chloride in water and evaporated. The residue is taken up in diethyl ether and the solution is filtered and evaporated; this gives impure, oily diphenylmethyl glyoxylate.

c. 0.402 g of diphenylmethyl glyoxylate is added to a solution of 0.147 g of 4β-acetylthio-3β-phenoxyacetylaminoazetidin-2-one in 5 ml of toluene and 1.5 ml of dimethylformamide and the reaction mixture is stirred in the presence of molecular sieves for 2½ hours at room temperature. It is filtered, the filtrate is evaporated and the residue is dried under a high vacuum. This gives diphenylmethyl 2-(4β-acetylthio-2-oxo-3β-phenoxyacetylamino-1-azetidinyl)-2-hydroxyacetate; thin layer chromatogram (silica gel): Rf = 0.33 (system: toluene/ethyl acetate, 1:1); which is further processed without purification.

d. 0.5 g of "polystyrene-Hunig base" and then 0.149 g of thionyl chloride are added to a solution of the diphenylmethyl 2-(4β-acetylthio-2-oxo-3β-phenoxyacetylamino-1-azetidinyl)-2-hydroxy-acetate prepared by the above process, in 5 ml of dioxane. The reaction mixture is stirred at room temperature for 3 hours and then filtered and the filtrate is evaporated. This gives crude diphenylmethyl 2-(4β-acetylthio-2-oxo-3β-phenoxyacetylamino-1-azetidinyl)-2-chloro-acetate; thin layer chromatogram (silica gel): Rf = 0.58 (system: toluene/ethyl acetate, 1:1); which is further processed without purification.

e. 0.5 g of "polystyrene-Hunig base" is added to a solution of the diphenylmethyl 2-(4β-acetylthio-2-oxo-3β-phenoxyacetylamino-1-azetidinyl)-2-chloro-acetate obtained by the above process, in 75 ml of dioxane, and the mixture is stirred at room temperature for 30 hours.

0.4 g of triphenylphosphine is added, the mixture is stirred for a further 20 hours at 50° and filtered and the filtrate is evaporated. The residue is chromatographed on silica gel (system: toluene/ethyl acetate, 1:1) and then purified by means of preparative layer chromatography. This gives oily diphenylmethyl 2-(4β-acetylthio-2-oxo-3β-phenoxyacetylamino-1-azetidinyl)-2-triphenylphosphoranylidene-acetate; thin layer chromatogram (silica gel): Rf = 0.28 (system: toluene/ethyl acetate, 1:1); infrared absorption spectrum (in methylene chloride): characteristic bands at 2.9μ, 3.45μ, 5.7μ, 5.95μ, 6.04μ, 6.2μ, 6.3μ, 6.65μ, 6.75μ, 7.0μ, 8.15μ, 8.35μ, 9.1μ, 9.34μ and 9.56μ.

EXAMPLE 12

A solution of 0.0446 g of ethyl trans-3-[1-(methoxycarbonyl-triphenylphosphoranylidene-methyl)-2-oxo-3β-phenoxyacetylamino-4β-azetidinyl-thio]-acrylate in 9.5 ml of methylene chloride and 0.5 ml of trifluoroacetic acid is treated, at −25°, with an ozone/oxygen mixture (0.1 mmol/minute), somewhat more than one equivalent of ozone being passed through in the course of 30 seconds. The reaction mixture is degassed with nitrogen and 0.5 ml of dimethyl sulphide is added. The mixture is reacted for a further 5 minutes a room temperature and then partitioned between methylene chloride and an excess of an 8% strength aqueous solution of sodium bicarbonate. The organic phase is washed with a saturated solution of sodium chloride and the aqueous phases are back-washed with methylene chloride. The combined organic solutions are dried over sodium sulphate and evaporated under reduced pressure at about 35°. According to the infrared absorption spectrum and the thin layer chromatogram, the reaction is not yet complete; the product is heated to 50° in 5 ml of toluene for 30 minutes and the mixture is evaporated. The residue is chromatographed on acid-washed silica gel (short column) and eluted with a 1:1 mixture of benzene and ethyl acetate. This gives methyl 6β-phenoxyacetylamino-2-penem-3-carboxylate as a colourless foam; thin layer chromatogram (silica gel): Rf = 0.58 (system: ethyl acetate); ultraviolet absorption spectrum (in ethanol): $\lambda_{max}$ = 310 mμ, 274 mμ, 268 mμ and 262 mμ; infrared absorption spectrum (in methylene chloride): characteristic bands at 2.97μ, 3.30μ, 3.42μ, 5.54μ, 5.81μ, 5.90μ, 6.25μ (shoulder), 6.39μ, 6.60μ, 6.70μ, 6.97μ, 7.41μ, 7.60μ, 8.08μ (shoulder) and 8.25μ (broad).

The starting material can be prepared as follows:

a. A solution of 0.0445 g of ethyl trans-3-(2-oxo-3β-phenoxyacetylamino-4β-azetidinyl-thio]-acrylate and 0.05 g of the hydrate of methyl glyoxylate in 1.5 ml of toluene and 0.4 ml of dimethylformamide is stirred at room temperature in the presence of molecular sieves for 3 hours. The mixture is filtered; the filter residue is washed with toluene and the combined filtrates are completely evaporated, finally under a high vacuum. The foam-like residue contains ethyl trans-3-[1-(hydroxymethoxycarbonyl-methyl)-2-oxo-3-phenoxyacetylamino-4β-azetidinyl-thio]-acrylate; thin layer chromatogram (silica gel): Rf = 0.40 (system: ethyl acetate); infrared absorption spection (in methylene chloride): characteristic bands at 2.89μ, 2.97μ, 3.43μ, 5.60μ, 5.73μ, 5.88μ, 6.28μ, 6.60μ, 6.70μ, 6.97μ, 7.43μ, 7.70–8.00μ (broad) and 8.50–8.60μ; and is further processed without purification.

b. The ethyl trans-3-[1-(hydroxymethoxycarbonyl-methyl)-2-oxo-3-phenoxyacetylamino-4β-azetidinyl-thio]-acrylate obtainable according to the above process is stirred in 1 ml of dioxane in the presence of 0.16 g of "polystyrene-Hunig base" for 30 minutes and 0.048 g of thionyl chloride in 0.35 ml of methylene chloride and 0.5 ml of dioxane are then added. The reaction mixture is stirred for a further 4 hours at room temperature and under a nitrogen atmosphere and is then filtered and the filter residue is washed with dioxane. The combined filtrates are evaporated, finally under a high vacuum and this gives amorphous ethyl trans-3-[1-(chloromethoxycarbonyl-methyl)-2-oxo-3-phenoxyacetylamino-4β-azetidinyl-thio]-acrylate; infrared absorption spectrum (in methylene chloride): characteristic bands at 2.97μ, 3.40–3.50μ, 5.57μ, 5.71μ, 5.87μ, 6.25μ, 6.60μ, 6.70μ, 6.96μ, 7.32μ, 7.58μ (shoulder), 7.68μ, 8.10μ (broad) and 8.57μ (broad).

c. The ethyl trans-3-[1-(chloromethoxycarbonyl-methyl)-2-oxo-3-phenoxyacetylamino-4β-azetidinyl-thio]-acrylate obtainable according to the above process is stirred in 2 ml of dioxane at 50° with 0.05 g of triphenylphosphine and 0.16 g of "polystyrene-Hunig base" for 20 hours. The reaction mixture is filtered, the filter residue is washed with dioxane and the combined filtrates are evaporated. The residue is purified by means of preparative layer chromatography (silica gel; system: ethyl acetate) and ethyl trans-3-[1-(methoxycarbonyl-triphenylphosphoranylidene-methyl)-2-oxo-3β-phenoxyacetylamino-4β-azetidinyl-thio]-acrylate is obtained as a colourless foam; thin layer chromatogram (silica gel): Rf = 0.26 (system: ethyl acetate); infrared absorption spectrum (in methylene chloride): characteristic bands at 2.97μ, 3.40–3.50μ, 5.67μ, 5.80μ (broad), 6.10μ (shoulder), 6.15μ, 6.27μ, 6.60μ, 6.70μ, 6.97μ, 7.24μ, 7.35μ, 7.70–8.15μ (broad), 8.50–8.62μ (broad) and 9.04μ.

EXAMPLE 13

4β-Acetylthio-3β-phenoxyacetylamino-azetidin-2-one, which has been described in Example 1, can also be prepared as follows:

a. A solution of 5.30 g of methyl 2-[4β-(2-benzthiazolyldithio)-2-oxo-3β-phenoxyacetylamino-1-azetidinyl]-2-(2-propylidene)-acetate (Example 5c) in 250 ml of dry dimethylformamide is cooled to −20° and treated, in the course of 5 minutes, with a solution of 0.50 g of sodium borohydride in 50 ml of dimethylformamide. The reaction mixture is kept at −20° for 30 minutes, 19 g of trityl bromide in 100 ml of dimethylformamide are then added at this temperature and the mixture is then brought to room temperature. It is stirred for 1 hour, diluted with 2,000 ml of toluene and washed three times with a total of 1,500 ml of water. The organic solution is dried over sodium sulphate and evaporated under reduced pressure. The residue is chromatographed on 250 g of silica gel and, using a 7:1 mixture of toluene and ethyl acetate (7 250 ml fractions) and a 2:1 mixture of toluene and ethyl acetate (7 250 ml fractions), methyl 2-(2-oxo-3β-phenylacetylamino-4β-tritylthio-1-azetidinyl)-2-(1-propen-2-ylidene)-acetate is eluted in the form of a non-crystalline material which crystallises spontaneously on the addition of ethyl acetate; melting point 177°–180° after recrystallisation from ethyl acetate; infrared absorption spectrum (in methylene chloride): characteristic bands at 5.65μ, 5.8μ, 5.9μ, 8.2μ and 9.3μ.

b. A solution of 0.627 g of methyl 2-(2-oxo-3β-phenylacetylamino-4β-tritylthio-1-azetidinyl)-2-(1-propen-2-ylidene)-acetate in 10 ml of methylene chloride is treated with an excess of ozone at −20° until no further starting material is present according to the thin layer chromatogram (system: toluene/ethyl acetate, 1:1). The mixture is then diluted with 50 ml of methylene chloride, washed with 20 ml of a 10% strength aqueous solution of sodium bisulphite and 20 ml of a dilute solution of sodium chloride in water, dried over sodium sulphate and evaporated under reduced pressure. This gives amorphous methyl 2-oxo-2-(2-oxo-3β-phenoxyacetylamino-4β-tritylthio-1-azetidinyl)-acetate; infrared absorption spectrum (in methylene chloride): characteristic bands at 5.5μ, 5.7μ, 5.9μ and 8.1μ; which is used without further purification.

c. A solution of 0.580 g of methyl 2-oxo-2-(2-oxo-3β-phenoxyacetylamino-4β-tritylthio-1-azetidinyl)-acetate in 2 ml of acetone is diluted with 100 ml of a 98:2 mixture of methanol and water and stirred at room temperature for 20 hours, and then evaporated under reduced pressure. The residue is taken to dryness again with 20 ml of methanol and the oily product is chromatographed on 18 g of silica gel, white crystalline 3β-phenoxyacetylamino-4β-tritylthio-azetidin-2-one being eluted with a 3:1 mixture of toluene and ethyl acetate; melting point 186°–187° after recrystallisation from a mixture of ethyl acetate and diethyl ether at 0°; infrared absorption spectrum (in methylene chloride): characteristic bands at 2.95μ, 5.65μ, 5.9μ, 6.25μ, 6.6μ, 6.7μ and 6.95μ.

d. A solution of 0.051 g of 3β-phenoxyacetylamino-4β-tritylthio-azetidin-2-one in 2 ml of methanol, prepared warm, is cooled, in a centrifuge vessel, so rapidly to 0° that no crystallisation occurs and a 0.1 N solution of silver nitrate in methanol is added, with shaking. A white colloidal precipitate forms immediately; the mixture is kept at 0° for a further 15 minutes and then centrifuged. The solution is discarded; the solid residue is washed with 2 ml of cold methanol and dissolved in 2 ml of dry dimethylformamide. A stream of hydrogen sulphide is allowed to pass through the solution at 0° until no further formation of silver sulphide can be detected. The mixture is filterd through cottonwool and the filtrate is evaporated under reduced pressure. The residue is taken to dryness again with toluene and gives crystalline 4β-mercapto-3β-phenoxyacetylamino-azetidin-2-one; melting point 116°–118° after recrystallisation from acetone; infrared absorption spectrum (in methylene chloride): characteristic bands at 5.65μ, 6.0μ, 6.25μ, 6.50μ, 6.7μ, 7.25μ and 8.05μ.

4β-Mercapto-3β-phenoxyacetylamino-azetidin-2-one can also be obtained as follows:

e. A solution of 5.30 g of methyl 2-[4β-(2-benzthiazolyldithio)-2-oxo-3β-phenoxyacetylamino-1-azetidinyl]-2-(1-propen-2-ylidene)-acetate (Example 5) in 100 ml of methanol is cooled to −20° and treated, at this temperature, with an ozone/oxygen mixture (0.33 mmol/minute) for 90 minutes. The resulting precipitate is filtered off and washed with 50 ml of cold methanol; this gives methyl 2-[4β-(2-benzthiazolyl-dithio)-2-oxo-3β-phenoxyacetylamino-1-azetidinyl]-2-oxo-acetate, which after recrystallisation from methanol melts at 135° to 139°. A further amount can be obtained by diluting the combined filtrates and wash solutions with 750 ml of methylene chloride, washing with 250 ml of a 10% strength aqueous solution of sodium bisulphite, drying over sodium sulphate and evaporating under reduced pressure.

f. A solution of 2.51 g of methyl 2-[4β-(2-benzthiazolyldithio)-2-oxo-3β-phenoxyacetylamino-1-azetidinyl]-2-oxo-acetate in 10 ml of tetrahydrofurane is diluted with 250 ml of a 98:2 mixture of methanol and water and stirred at room temperature for 20 hours and then evaporated under reduced pressure and the residue is again taken to dryness with 50 ml of methanol. The crystalline residue is stirred with 30 ml of ethyl acetate and the mixture is filtered. The filtrate is kept at 0° for 16 hours. The crystalline residue and the product crystallised from the filtrate give 4β-(2-benzthiazolyl-dithio)-3β-phenoxyacetylamino-azetidin-2-one; melting point 156°–158° after recrystallisation from a mixture of methylene chloride and methanol.

g. A solution of 0.082 g of 4β-(2-benzthiazolyl-dithio)-3β-phenoxyacetylamino-azetidin-2-one in 4 ml of dry dimethylformamide is stirred at −20° and a solution of 0.025 g of sodium borohydride in 1 ml of dimethylformamide is added and the reaction mixture is stirred at −20° for 30 minutes. 0.2 ml of trifluoroacetic acid is added in the course of 5 minutes and the mixture is stirred at −20° for a further 5 minutes and then diluted with 50 ml of ethyl acetate, washed with an ice-cold dilute solution of sodium chloride in water and dried over sodium sulphate. The solvent is removed under a high vacuum; the residue is taken to dryness with 5 ml of toluene and chromatographed on 3.5 g of silica gel, the product being eluted with 15 1.5 ml fractions of ethyl acetate. After 2-mercapto-benzthiazole, 4β-mercapto-3β-phenoxyacetylaminoazetidin-2-one is eluted; melting point 123°–124° after recrystallisation from ethyl acetate.

h. 0.5 ml of acetic anhydride is added to a solution of 0.0125 g of 4β-mercapto-3β-phenoxyacetylamino-azetidin-2-one in one drop of tetrahydrofurane and the mixture is left to stand at 0° for 16 hours. The reaction mixture is evaporated under a high vacuum, the residue is taken to dryness again with 1 ml of toluene and the residue is chromatographed on 0.5 g of silica gel, the product being eluted with a 2:1 mixture of toluene and ethyl acetate. This gives crystalline 4β-acetylthio-3β-phenoxyacetylamino-azetidin-2-one; melting point 137.5°–138.5° after recrystallisation from a mixture of methylene chloride and diethyl ether; which is identical with the product of Example 1.

EXAMPLE 14

A solution of 100 mg of tert.-butyl 2-(4β-acetylthio-2-oxo-3β-phthalimido-1-azetidinyl)-2-triphenylphosphoranylideneacetate in 50 ml of absolute dioxane is heated under reflux, in the presence of 500 mg of "polystyrene-Hunig base", for 48 hours. The reaction mixture is concentrated in vacuo and the residue is purified by chromatography on 10 g of acid-washed silica gel (stir 2 kg of silica gel with 3 times 2 l of concentrated hydrochloric acid for 10 minutes, decant off the acid, wash the silica gel with distilled water until neutral, rinse with methanol and activate for 60 hours at 120°), which is de-activated with 10% of water, using benzene as the eluant. The resulting tert.-butyl 2-methyl-6β-phthalimido-2-penem-3-carboxylate crystallises in the form of colourless needles from methylene chloride/diethyl ether; melting point 179°–181° C; UV spectrum (in 96% strength ethanol): $\lambda_{max}$ = 303 mμ (ε - 6,370); IR spectrum (in methylene chloride): characteristic absorption bands at 3.30; 3.40; 5.55; 5.63; 5.74; 5.80; 6.25; 7.24; 7.33; 7.50–7.58; 7.80–8.05; 8.33 and 8.70μ.

b. A $O_3/O_2$ mixture (0.33 mmol of $O_3$/minutes) is passed through a solution of 2.5 g of methyl 2-(4β-acetylthio-3β-phthalimido-2-oxo-1-azetidinyl)-2-(1-propen-2-yl)-acetate (R. Latrel, Liebigs Ann. 1974, 1937) in 60 ml of methylene chloride and 60 ml of methanol at −20° C for 2 hours and 5 minutes. The reaction mixture is left to stand at −20° C for 1 hour, diluted with methylene chloride and shaken with 100 ml of 10% strength aqueous sodium bisulphite solution. The organic phase is washed with aqueous sodium chloride solution, dried over sodium sulphate and freed from the solvent under reduced pressure. The amorphous residue, which contains amorphous methyl 2-(4$\beta$-acetylthio-2-oxo-3$\beta$-phthalimido-1-azetidinyl)-2-oxo-acetate, is employed in the next stage without further purification.

c. A solution of 7.5 g of amorphous methyl 2-(4$\beta$-acetylthio-2-oxo-3$\beta$-phthalimido-1-azetidinyl)-2-oxo-acetate in a mixture of 85 ml of methyl acetate, 750 ml of methanol and 16 ml of water is left to stand for 18 hours at room temperature. The resulting reaction mixture is concentrated under reduced pressure, 250 ml of methylene chloride are added to the residue, the aqueous phase is separated off and the organic phase is dried over sodium sulphate. After evaporating off the solvent in vacuo and crystallising the residue from methylene chloride/diethyl ether, 4$\beta$-acetylthio-3$\beta$-phthalimido-azetidin-2-one is obtained; melting point 164°–170° C; IR spectrum (methylene chloride): characteristic absorption bands at 2.97; 3.34; 3.41; 5.57; 5.65; 5.80; 5.90; 7.23; 7.85–8.05; 8.30; 8.95 and 9.05$\mu$.

d. Freshly activated molecular sieves (see Example 1f) are added to a solution of 1.45 g of 4$\beta$-acetylthio-3$\beta$-phthalimidoazetidin-2-one and 2.475 g of the hydrate of tert.-butyl glyoxylate in 50 ml of toluene and 12 ml of dimethylformamide and the mixture is stirred under nitrogen for 90 minutes at room temperature. The molecular sieve is filtered off and washed with toluene and the filtrates and washing liquid are evaporated in vacuo. The residue is chromatographed on silica gel using 9:1 and 4:1 benzene/ethyl acetate and gives a mixture of the two epimers of tert.-butyl 2-(4$\beta$-acetylthio-2-oxo-3$\beta$-phthalimido-1-azetidinyl)-2-hydroxy-acetate. By means of crystallisation from methylene chloride/diethyl ether, it is possible to obtain, from this mixture, one of the epimers in a crystalline form with a melting point of 155°–157° C. IR spectrum (in methylene chloride): characteristic absorption bands at 2.95–3.55 (broad); 5.60; 5.63 (sh); 5.79; 5.88 (sh); 7.23; 7.32; 7.80–8.05 (broad) $\mu$.

e. A solution of 640 g of crystalline tert.-butyl 2-(4$\beta$-acetylthio-2-oxo-3$\beta$-phthalimido-1-azetidinyl)-2-hydroxy-acetate in 13 ml of absolute dioxane is stirred at room temperature for 30 minutes with 1.28 g of "polystyrene-Hunig base" (see Example 1h; neutralises 3.68 milliequivalents of hydrochloric acid per gram) and a solution of 533 mg of thionyl chloride in 9 ml of dioxane is then added dropwise. The mixture is stirred under nitrogen for a further 4½ hours at room temperature. The "polystyrene-Hunig base" is filtered off and washed with dioxane and the filtrate and wash liquid are evaporated together under reduced pressure. The residue contains a mixture of the two epimers of tert.-butyl 2-(4$\beta$-acetylthio-2-oxo-3$\beta$-phthalimido-1-azetidinyl)-2-chloro-acetate; thin layer chromatogram: Rf value 0.56 (Merck silica gel; benzene:ethyl acetate, 1:1); IR spectrum (in methylene chloride)-characteristic absorption bands at 3.30; 3.40; 5.57; 5.63 (sh); 5.72 (sh); 5.78; 5.87 (sh); 7.20; 7.35; 7.58; 7.80–8.05 and 8.70$\mu$.

A similar mixture of epimers is obtained when the noncrystalline mixture of epimers is used as the starting material.

f. A solution of 756 mg of tert.-butyl 2-(4$\beta$-acetylthio-2-oxo-3$\beta$-phthalimido-1-azetidinyl)-2-chloro-acetate in 21 ml of dioxane is stirred for 30 minutes at room temperature with 1.68 g of "polystyrene-Hunig base" (neutralises 3.68 milliequivalents of hydrochloric acid per gram). After adding 766 mg of triphenylphosphine, the mixture is stirred under nitrogen at 70° C. After 68 hours, the "polystyrene-Hunig base" is filtered off and washed with dioxane and the filtrate and wash liquid are evaporated together in vacuo. The residue is chromatographed on 50 g of Merck silica gel using 9:1 benzene/ethyl acetate, unconverted triphenylphosphine being eluted first. 4:1 benzene/ethyl acetate then elutes amorphous tert.-butyl 2-(4$\beta$-acetylthio-2-oxo-3$\beta$-phthalimido-1-azetidinyl)-2-triphenylphosphoranylidene-acetate; thin layer chromatogram: Rf value = 0.32 (silica gel; benzene/ethyl acetate, 1:1); IR spectrum (in methylene chloride): characteristic absorption bands at 3.30; 3.40; 5.59; 5.65; 5.79; 5.90; 6.04–6.10; 6.13–6.20; 6.47; 7.22; 7.35; 7.80–8.05; 8.10 (broad) and 8.85–9.05 (broad) $\mu$.

EXAMPLE 15 a. A solution of 85 mg of p-methoxybenzyl 2-(4$\beta$-acetylthio-2-oxo-3$\beta$-phenoxyacetylamino-1-azetidinyl)-2-triphenylphosphoranylidene-acetate in 85 ml of toluene is warmed at 80° C under argon for 48 hours. The solvent is evaporated under reduced pressure and the residue is chromatographed on 15 g of silica gel using 4:1 benzene/ethyl acetate. p-Methoxybenzyl 2-methyl-6$\beta$-phenoxyacetylamino-2-penem-3-carboxylate is obtained; thin layer chromatogram: Rf value: 0.52 (silica gel; benzene/ethyl acetate, 1:1); UV spectrum (in 96% strength ethanol): $\lambda_{max}$ = 305 m$\mu$; 272 m$\mu$; 267 m$\mu$; 260 m$\mu$; IR spectrum (in methylene chloride): characteristic absorption bands at 2.97; 3.30; 3.42; 3.57; 5.56; 5.85 (sh); 5.88; 6.20; 6.27; 6.60; 6.70; 6.96; 7.07 (sh); 7.30; 7.70; 8.07; 8.27; 8.51–8.60 (broad); 9.26 and 9.69 $\mu$.

The starting material can be obtained as follows:

b. A solution of 8.04 g of p-methoxybenzyl bromide in 20 ml of dimethylformamide is added dropwise to a solution of 3 g of L-(+)-tartaric acid in 20 ml of dimethylformamide and 5.6 ml of triethylamine and the reaction mixture is stirred for 3 hours at room temperature and partitioned between 300 ml of benzene and 100 ml of water. The organic phase is washed with twice 100 ml of water, dried over sodium sulphate and freed from the solvent in vacuo. The resulting crude, but crystalline, di-p-methoxybenzyl ester of L-(+)-tartaric acid has a melting point of 98°–100° C. Rf value = 0.34 (silica gel; ethyl acetate/benzene, 1:1); IR spectrum (in methylene chloride): absorption bands at 2.88; 3.30; 3.43; 3.58; 5.75; 6.21; 6.60; 6.85–7.10 (broad); 8.08; 8.52; 8.95; 9.25 and 9.69$\mu$.

c. 5.2 g of lead tetraacetate are added, in several portions, in the course of 20 minutes to a solution of 4.6 g of the resulting crude di-p-methoxybenzyl L-(+)-tartrate in 150 ml of benzene and the reaction mixture is stirred for 5 hours at room temperature. The precipitate is filtered off and washed with benzene and the filtrate and the wash liquid are evaporated together in vacuo. The residue is dissolved in methylene chloride (rendered alcohol-free by filtering through aluminium oxide) and the solution is washed with 4% strength aqueous sodium bicarbonate solution. The organic phase is evaporated under reduced pressure and gives a mixture of hydrated, hemi-hydrated and non-hydrated p-methoxybenzyl glyoxylate. Rf value = 0.25 (silica gel;

ethyl acetate/benzene, 1:1); IR spectrum (in methylene chloride): absorption bands at 2.90; 3.30; 3.40; 3.57; 5.74 (broad); 6.20; 6.30; 6.60; 8.05; 8.50; 8.98–9.05 (sh); 9.14 (broad) and 9.68 μ.

d. Activated molecular sieves are added to a solution of 588 mg of 4β-acetylthio-3β-phenoxyacetylamino-2-oxo-azetidine and 900 mg of the resulting crude p-methoxybenzyl glyoxylate in 30 ml of toluene and 5 ml of dimethylformamide and the mixture is stirred for 3 hours at room temperature. The molecular sieves are filtered off and washed with toluene and the filtrate and the wash liquid are evaporated together in vacuo. This gives amorphous, crude p-methoxybenzyl 2-(4β-acetylthio-3β-phenoxyacetylamino-2-oxo-1-azetidinyl)-2-hydroxy-acetate; Rf value = 0.20, elongated spots, silica gel; benzene/ethyl acetate, 1:1).

e. 1.8 g of "polystyrene-Hunig base" (neutralises 3.45 milliequivalents of hydrochloric acid per gram) are added to a solution of 1.49 g of the resulting crude p-methoxybenzyl 2-(4β-acetylthio-3β-phenoxyacetylamino-2-oxo-1-azetidinyl)-2-hydroxy-acetate in 20 ml of dioxane and the mixture is stirred for 30 minutes at room temperature. A solution of 720 ml of thionyl chloride in 12 ml of dioxane is added dropwise and the reaction mixture is stirred under nitrogen for 2.5 hours at room temperature. The "polystyrene-Hunig base" is filtered off and washed with dioxane. When the filtrate and wash liquid are evaporated together in vacuo this gives crude p-methoxybenzyl 2-(4β-acetylthio-3β-phenoxyacetylamino-2-oxo-1-azetidinyl)-2-chloro-acetate; Rf value = 0.50 (silica gel; ethyl acetate/benzene, 1:1).

f. A solution of 1.5 g of crude p-methoxybenzyl 2-(4β-acetylthio-3β-phenoxyacetylamino-2-oxo-1-azetidinyl)-2-chloroacetate and 786 mg of triphenylphosphine in 20 ml of dioxane is stirred for 16 hours at 50° C under nitrogen in the presence of 1.8 g of "polystyrene-Hunig base" (neutralises 3.45 milliequivalents of hydrochloric acid per gram), which has been pretreated in the same solvent for 30 minutes. The "polystyrene-Hunig base" is filtered off and washed with dioxane and the filtrate and wash liquid are evaporated together under reduced pressure. The syrupy residue is chromatographed on 30 g of silica gel. Using 4:1 benzene/ethyl acetate, fast-flowing by-products are first eluted. 1:1 benzene/ethyl acetate then elutes p-methoxybenzyl 2-(4β-acetylthio-2-oxo-3-phthalimido-1-azetidinyl)-2-triphenylphosphoranylidene-acetate, which, for further purification, can be chromatographed on 6 preparative silica gel thick layer plates using 1:1 benzene/ethyl acetate as the running agent. Rf value = 0.24 (silica gel; benzene/ethyl acetate, 1:1); IR spectrum (in methylene chloride): characteristic absorption bands at 2.95; 3.30; 3.40; 3.55; 5.65; 5.90; 6.08 (sh); 6.13 (sh); 6.19; 6.21 (sh); 6.25 (sh); 6.60; 6.70; 6.95; 7.85–8.00 (broad); 8.06; 8.53 and 9.05μ.

EXAMPLE 16

The compounds which follow can be obtained in an analogous manner and using the suitable intermediate products and, if necessary, liberating functional groups: 6-phenoxyacetyl-amino-2-penem-4-carboxylic acid, 2-ethyl-6-phenoxyacetylamino-2-penem-4-carboxylic acid, 2-isopropyl-6-phenoxyacetylamino-2-penem-4-carboxylic acid, 2-phenyl-6-phenoxyacetylamino-2-penem-4-carboxylic acid, 2-benzyl-6-phenoxyacetylamino-2-penem-4-carboxylic acid, 2-acetyloxymethyl-6-phenoxyacetylamino-2-penem-4-carboxylic acid, 6-(D-2-amino-2-phenyl-acetylamino)-2-methyl-2-penem-4-carboxylic acid, 6-(2-carboxy-2-phenylacetylamino)-2-methyl-2-penem-4-carboxylic acid and 6-(2,2-dimethyl-5-oxo-4-phenyl-1-imidazolidinyl)-2-methyl-2-penem-4-carboxylic acid, or salts of such compounds, in which the free carboxyl and/or amino groups are liberated, for example as described above, from suitably protected carboxyl and/or amino groups.

EXAMPLE 17

Dry ampoules or phials, containing 0.5 g of the dicyclohexylamine salt of 6β-phenoxyacetylamino-2-methyl-2-penem-3-carboxylic acid, are manufactured as follows:

| Composition (for 1 ampoule or phial) | |
|---|---|
| Dicyclohexylamine salt of 6β-phenoxyacetylamino-2-methyl-2-penem-3-carboxylic acid | 0.5 g |
| Mannitol | 0.05 g |

A sterile aqueous solution of the dicyclohexylamine salt of 6β-phenoxyacetylamino-2-methyl-2-penem-3-carboxylic acid and of mannitol is subjected to freeze-drying under aseptic conditions in 5 ml ampoules or 5 ml phials and the ampoules or phials are sealed and tested.

EXAMPLE 18

Capsules, containing 0.25 g of 6β-phenoxyacetylamino-2-methyl-2-penem-3-carboxylic acid, are manufactured as follows:

| Composition (for 1,000 capsules): | |
|---|---|
| 6β-Phenoxyacetylamino-2-methyl-2-penem-carboxylic acid | 250,000 g |
| Maize starch | 50,000 g |
| Polyvinylpyrrolidone | 15,000 g |
| Magnesium stearate | 5,000 g |
| Ethanol | q.s. |

The 6β-phenoxyacetylamino-2-methyl-2-penem-3-carboxylic acid and the maize starch are mixed and moistened with a solution of the polyvinylpyrrolidone in 50 g of ethanol. The moist mass is pressed through a sieve with a mesh width of 3 mm and dried at 45°. The dry granules are forced through a sieve with a mesh width of 1 mm and mixed with 5 g of magnesium stearate. The mixture is filled in portions of 0.320 g into size O push-fit capsules.

What is claimed is:

1. A 6-amino-2-penem-3-carboxylic acid compound of the formula

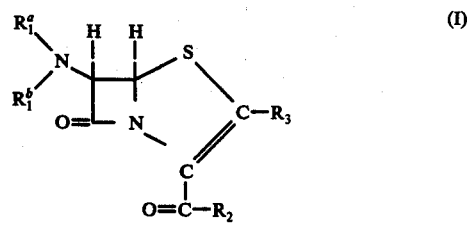

(I)

in which $R_1^a$ is hydrogen or a group $R_1^A$ which denotes a conventional acyl radical of an organic carboxylic acid having up to 18 carbon atoms, a conventional triarylmethyl group or a conventional organic silyl or stannyl group, $R_1^b$ is hydrogen or a conventional acyl radical or an organic carboxylic acid having up to 18 carbon atoms, $R_1^a$ and $R_1^b$ together is a conventional bivalent acyl radical of an organic dicarboxylic acid having up to 18 carbon atoms or the conventional acyl radical of an α-aminoacetic acid, which is substituted in α-position by an aromatic or heterocyclic group, and in which the amino group is bonded to the nitrogen atom via a methylene radical which is substituted by two lower alkyl groups, or $R_1^a$ and $R_1^b$ together represent a conventional aliphatic, cycloaliphatic, cycloaliphatic-aliphatic or araliphatic ylidene radical having up to 18 carbon atoms, $R_2$ denotes hydroxyl or a radical $R_1^A$ which, together with the carbonyl grouping —C(=O)—, forms a conventional protected carboxyl group, and $R_3$ is hydrogen lower alkyl with up to 7 carbon atoms, cycloalkyl with 3 to 7 carbon atoms, cycloalkyl-lower alkyl with 4 to 7 carbon atoms, phenyl, naphthyl or phenyl-lower alkyl or such group substituted by hydroxyl, mercapto, lower alkoxy, lower alkanoyloxy, halogen, lower alkylmercapto, carboxyl, lower alkoxycarbonyl, carbamoyl, cyano, nitro, amino, lower alkylamino, di-lower alkylamino or lower alkylene-amino, or $R_3$ is pyridyl, thienyl, furyl, pyridyl-lower alkyl, thienyl-lower alkyl or furyl-lower alkyl, the 1-oxide thereof and pharmaceutically acceptable salts thereof.

2. A 6-amino-2-penem-3-carboxylic acid compound of the formula I, according to claim 1, in which $R_1^a$ represents hydrogen or an acyl group of the formula

in which (1) $R_a$ denotes phenyl, hydroxyphenyl, lower alkylsulphonylaminophenyl, aminomethylphenyl, thienyl, aminomethylthienyl, furyl, aminomethylfuryl, 1,4-cyclohexadienyl, aminomethyl-1,4-cyclohexadienyl, 1-cyclohexenyl or aminomethyl-1-cyclohexenyl, and, in the above radicals, hydroxyl and/or amino can be protected with conventional protecting groups, $R_b$ represents hydrogen and $R_c$ represents hydrogen, amino, protected amino, conventionally hydroxyl, conventionally protected hydroxyl, carboxyl or sulpho, or carboxyl or sulpho esterified with lower alkyl, or in which (2) $R_2$ represents cyano, 1-tetrazolyl, phenoxy or 4-pyridylthio and $R_b$ and $R_c$ represent hydrogen, or in which (3) $R_a$ represents phenyl, 2-thienyl or 2-furyl and $R_b$ and $R_c$ together denote syn-lower alkoxyimino, $R_1^b$ denotes hydrogen, $R_2$ represents hydroxyl, methoxy, α-poly-branched lower alkoxy, 2-halogeno-lower alkoxy, lower alkenyloxy, diphenylmethoxy which is unsubstituted or substituted by lower alkoxy, 4-nitrobenzyloxy, pentachlorophenoxy or tri-lower alkylsilyloxy and $R_3$ denotes hydrogen, lower alkyl with up to 4 carbon atoms, lower alkoxy-lower alkyl with up to 4 carbon atoms, or lower alkanoyloxy-lower alkyl with up to 4 carbon atoms, phenyl which is unsubstituted or substituted by nitro or amino, or benzyl, and pharmaceutically acceptable salts thereof.

3. Tert.-butyl 6β-phenoxyacetylamino-2-penem-3-carboxylate according to claim 1.

4. Tert.-butyl 2-methyl-6β-phenoxyacetylamino-2-penem-3-carboxylate, according to claim 1.

5. Tert.-butyl 2-(4-aminophenyl)-6β-phenoxyacetylamino-2-penem-3-carboxylate, according to claim 1.

6. 4-Nitrobenzyl 2-methyl-6β-phenoxyacetylamino-2-penem-3-carboxylate, according to claim 1.

7. 2-Methyl-6β-phenoxyacetylamino-2-penem-3-carboxylic acid, or salts thereof, according to claim 1.

8. Tert.-butyl 2-isopropyl-6β-phenoxyacetylamino-2-penem-3-carboxylate, according to claim 1.

9. Diphenylmethyl 2-methyl-6β-phenoxyacetylamino-2-penem-3-carboxylate, according to claim 1.

10. p-Methoxybenzyl-2-methyl-6β-phenoxyacetylamino-2-penem-3-carboxylate, according to claim 1.

11. An antibacterial pharmaceutical preparation comprising a therapeutically effective amount of a compound according to claim 1 together with a pharmaceutically usable excipient.

12. A method for the treatment of bacterial infections which comprise administering to a host a therapeutically effective amount of a compound according to claim 1.

* * * * *